United States Patent
Kondabatni et al.

(10) Patent No.: US 9,468,750 B2
(45) Date of Patent: Oct. 18, 2016

(54) MULTILAYER PLANAR SPIRAL INDUCTOR FILTER FOR MEDICAL THERAPEUTIC OR DIAGNOSTIC APPLICATIONS

(71) Applicant: Greatbatch Ltd., Clarence, NY (US)

(72) Inventors: Kishore K. Kondabatni, Arcadia, CA (US); Christine A. Frysz, Orchard Park, NY (US)

(73) Assignee: Greatbatch Ltd., Clarence, NY (US)

(*) Notice: Subject to any disclaimer, the term of this patent is extended or adjusted under 35 U.S.C. 154(b) by 514 days.

(21) Appl. No.: 13/958,604

(22) Filed: Aug. 4, 2013

(65) Prior Publication Data

US 2013/0338747 A1    Dec. 19, 2013

(51) Int. Cl.
| | | |
|---|---|---|
| A61N 1/00 | (2006.01) |
| A61N 1/05 | (2006.01) |
| A61N 1/37 | (2006.01) |
| H01F 17/02 | (2006.01) |
| H03H 1/00 | (2006.01) |
| A61N 1/08 | (2006.01) |

(52) U.S. Cl.
CPC ............ *A61N 1/05* (2013.01); *A61N 1/3718* (2013.01); *A61N 2001/086* (2013.01); *H01F 17/02* (2013.01); *H03H 1/0007* (2013.01)

(58) Field of Classification Search
CPC ............. A61N 2001/086; A61N 1/3718; A61N 1/05; H03H 1/0007; H01G 17/02
See application file for complete search history.

(56) References Cited

U.S. PATENT DOCUMENTS

| | | |
|---|---|---|
| 3,871,382 A | 3/1975 | Mann |
| 3,968,802 A | 7/1976 | Ballis |
| 3,980,975 A | 9/1976 | Maxon, Jr. et al. |
| 4,236,127 A | 11/1980 | Scherba |
| 4,633,181 A | 12/1986 | Murphy-Boesch et al. |
| 4,654,880 A | 3/1987 | Sontag |

(Continued)

FOREIGN PATENT DOCUMENTS

| | | |
|---|---|---|
| EP | 0243573 A2 | 11/1987 |
| EP | 0145430 B1 | 5/1991 |

(Continued)

OTHER PUBLICATIONS

"EP Search", Application No. 14172182.9, Oct. 10, 2014.

(Continued)

*Primary Examiner* — Niketa Patel
*Assistant Examiner* — Lindsey G Hankins
(74) *Attorney, Agent, or Firm* — Michael F. Scalise; Marc G. Martino

(57) ABSTRACT

A multilayer helical wave filter having a primary resonance at a selected RF diagnostic or therapeutic frequency or frequency range, includes an elongated conductor forming at least a portion of an implantable medical lead. The elongated conductor includes a first helically wound segment having at least one planar surface, a first end and a second end, which forms a first inductive component, and a second helically wound segment having at least one planar surface, a first end and a second end, which forms a second inductive element. The first and second helically wound segments are wound in the same longitudinal direction and share a common longitudinal axis. Planar surfaces of the helically wound segments face one another, and a dielectric material is disposed between the facing planar surfaces of the helically wound segments and between adjacent coils of the helically wound segments, thereby forming a capacitance.

31 Claims, 44 Drawing Sheets

(56) References Cited

U.S. PATENT DOCUMENTS

| | | |
|---|---|---|
| 4,689,621 A | 8/1987 | Kleinberg |
| 4,799,499 A | 1/1989 | Bisping |
| 4,858,623 A | 8/1989 | Bradshaw et al. |
| 5,082,888 A * | 1/1992 | Abe .................. C08K 3/34 524/449 |
| 5,209,233 A | 5/1993 | Holland et al. |
| 5,217,010 A | 6/1993 | Tsitlik et al. |
| 5,246,438 A | 9/1993 | Langberg |
| 5,291,180 A * | 3/1994 | Reeb ................ G08B 13/2417 257/E27.114 |
| 5,300,108 A | 4/1994 | Rebell et al. |
| 5,333,095 A | 7/1994 | Stevenson et al. |
| 5,363,845 A | 11/1994 | Chowdhury et al. |
| 5,398,683 A | 3/1995 | Edwards et al. |
| 5,428,337 A | 6/1995 | Vinclarelli et al. |
| 5,514,173 A | 5/1996 | Rebell et al. |
| 5,545,201 A | 8/1996 | Helland et al. |
| 5,629,622 A | 5/1997 | Scampini |
| 5,697,958 A | 12/1997 | Paul et al. |
| 5,716,390 A | 2/1998 | Li |
| 5,722,998 A | 3/1998 | Prutchi et al. |
| 5,741,321 A | 4/1998 | Brennen |
| 5,751,539 A | 5/1998 | Stevenson et al. |
| 5,759,202 A | 6/1998 | Schroeppel |
| 5,874,745 A * | 2/1999 | Kuo ................ H01L 21/28008 257/324 |
| 5,905,627 A | 5/1999 | Brendel et al. |
| 5,959,829 A | 9/1999 | Stevenson et al. |
| 5,964,705 A | 10/1999 | Truwit et al. |
| 5,973,906 A | 10/1999 | Stevenson et al. |
| 5,978,204 A | 11/1999 | Stevenson |
| 6,008,980 A | 12/1999 | Stevenson et al. |
| 6,055,457 A | 4/2000 | Bonner |
| 6,101,417 A | 8/2000 | Vogel et al. |
| 6,141,594 A | 10/2000 | Flynn et al. |
| 6,159,560 A | 12/2000 | Stevenson et al. |
| 6,236,205 B1 | 5/2001 | Ludeke et al. |
| 6,275,369 B1 | 8/2001 | Stevenson et al. |
| 6,280,385 B1 | 8/2001 | Melzer et al. |
| 6,424,234 B1 | 7/2002 | Stevenson |
| 6,456,481 B1 | 9/2002 | Stevenson |
| 6,473,291 B1 | 10/2002 | Stevenson |
| 6,493,591 B1 | 12/2002 | Stokes |
| 6,529,103 B1 | 3/2003 | Brendel et al. |
| 6,535,766 B1 | 3/2003 | Thompson et al. |
| 6,539,253 B2 | 3/2003 | Thompson et al. |
| 6,566,978 B2 | 5/2003 | Stevenson et al. |
| 6,567,259 B2 | 5/2003 | Stevenson et al. |
| 6,567,703 B1 | 5/2003 | Thompson et al. |
| 6,606,513 B2 | 8/2003 | Lardo et al. |
| 6,643,903 B2 | 11/2003 | Stevenson et al. |
| 6,675,033 B1 | 1/2004 | Lardo et al. |
| 6,675,779 B2 | 1/2004 | King et al. |
| 6,687,550 B1 | 2/2004 | Doan |
| 6,701,176 B1 | 3/2004 | Halperin et al. |
| 6,765,780 B2 | 7/2004 | Brendel et al. |
| 6,847,837 B1 | 1/2005 | Melzer et al. |
| 6,868,288 B2 | 3/2005 | Thompson |
| 6,876,885 B2 | 4/2005 | Swoyer et al. |
| 6,882,248 B2 | 4/2005 | Stevenson et al. |
| 6,898,454 B2 | 5/2005 | Atalar et al. |
| 6,925,328 B2 | 8/2005 | Foster et al. |
| 6,931,286 B2 | 8/2005 | Sigg et al. |
| 6,949,929 B2 | 9/2005 | Gray et al. |
| 6,952,613 B2 | 10/2005 | Swoyer et al. |
| 6,971,391 B1 | 12/2005 | Wang et al. |
| 6,985,347 B2 | 1/2006 | Stevenson et al. |
| 6,999,818 B2 | 2/2006 | Stevenson et al. |
| 7,013,180 B2 | 3/2006 | Dougherty et al. |
| 7,038,900 B2 | 5/2006 | Stevenson et al. |
| 7,092,766 B1 | 8/2006 | Salys et al. |
| 7,113,387 B2 | 9/2006 | Stevenson et al. |
| 7,123,013 B2 | 10/2006 | Gray |
| 7,148,783 B2 | 12/2006 | Parsche et al. |
| 7,155,271 B2 | 12/2006 | Halperin et al. |
| 7,363,090 B2 | 4/2008 | Halperin et al. |
| 7,511,921 B2 | 3/2009 | Mallary et al. |
| 7,561,906 B2 | 7/2009 | Atalar et al. |
| 7,702,387 B2 | 4/2010 | Stevenson et al. |
| 7,751,903 B2 | 7/2010 | Stevenson et al. |
| 7,853,324 B2 | 12/2010 | Stevenson et al. |
| 7,853,325 B2 | 12/2010 | Dabney et al. |
| 7,899,551 B2 | 3/2011 | Westlund et al. |
| 7,917,213 B2 | 3/2011 | Bulkes et al. |
| 7,945,322 B2 | 5/2011 | Stevenson et al. |
| 2003/0028094 A1 | 2/2003 | Kumar et al. |
| 2003/0050557 A1 | 3/2003 | Susil et al. |
| 2003/0144720 A1 | 7/2003 | Villaseca et al. |
| 2004/0167392 A1 | 8/2004 | Halperin et al. |
| 2004/0263174 A1 | 12/2004 | Gray et al. |
| 2005/0077984 A1 | 4/2005 | Lee et al. |
| 2005/0197677 A1 | 9/2005 | Stevenson |
| 2006/0009819 A1 | 1/2006 | Przybyszewski |
| 2006/0041294 A1 | 2/2006 | Gray |
| 2006/0100506 A1 | 5/2006 | Halperin et al. |
| 2008/0049376 A1 | 2/2008 | Stevenson et al. |
| 2008/0051854 A1 | 2/2008 | Bulkes et al. |
| 2008/0243218 A1 | 10/2008 | Bottomley et al. |
| 2008/0262584 A1 * | 10/2008 | Bottomley .............. A61N 1/05 607/119 |
| 2009/0179716 A1 | 7/2009 | Gay |
| 2009/0281592 A1 | 11/2009 | Vase |
| 2010/0010602 A1 | 1/2010 | Wedan et al. |
| 2010/0076538 A1 | 3/2010 | Desai et al. |
| 2010/0114277 A1 | 5/2010 | Zhao et al. |
| 2010/0160997 A1 | 6/2010 | Johnson et al. |
| 2010/0174348 A1 | 7/2010 | Bulkes et al. |
| 2010/0174349 A1 | 7/2010 | Stevenson et al. |
| 2010/0217262 A1 | 8/2010 | Stevenson et al. |
| 2010/0318164 A1 | 12/2010 | Chen et al. |
| 2011/0004283 A1 | 1/2011 | Stevenson et al. |
| 2011/0015713 A1 | 1/2011 | Min |
| 2011/0144734 A1 | 6/2011 | Westlund et al. |
| 2011/0196462 A1 | 8/2011 | Weiss et al. |
| 2011/0230943 A1 | 9/2011 | Johnson et al. |
| 2012/0029342 A1 | 2/2012 | Kondabatni et al. |

FOREIGN PATENT DOCUMENTS

| | | | |
|---|---|---|---|
| EP | 0 498 996 B1 | 3/1997 | |
| EP | 0930509 B1 | 12/1998 | |
| EP | 1021730 B1 | 4/1999 | |
| JP | 60141034 | 7/1985 | |
| JP | 61181925 | 8/1986 | |
| JP | 62233905 | 10/1987 | |
| JP | 4071536 | 3/1992 | |
| JP | 6054823 | 3/1994 | |
| JP | 11239572 | 9/1999 | |
| JP | 2005-117606 | 4/2005 | |
| NL | WO 2009045102 A2 * | 4/2009 | .......... H01L 27/283 |
| WO | WO 99/19739 | 4/1999 | |
| WO | WO 02/083016 A1 | 10/2000 | |

OTHER PUBLICATIONS

Ariel Roguin, et al., Modern Pacemaker and Implantable Cardioverter/Defibrillator Systems Can Be Magnetic Resonance Imaging Safe, Circulation—Journal of the American Heart Association, Aug. 4, 2004 (originally published online Jul. 26, 2004), pp. 475-482, American Heart Association, Dallas, Texas, USA.

Robert C. Susil, Christopher J. Yeung, Henry R. Halperin, Albert C. Lardo, Ergin Atalar, Multifunctional Interventional Devices for MRI: A Combined Electrophysiology/MRI Catheter, Magnetic Resonance in Medicine, 2002, pp. 594-600, Wiley-Liss, Inc., Departments of Biomedical Engineering, Radiology & Medicine, Johns Hopkins University School of Medicine, Baltimore, Maryland.

Robert C. Susil, Ergin Atalar, Albert Lardo, Multifunctional Interventional Devices for Use in MRI, U.S. Appl. No. 60/283,725, filed Apr. 13, 2001.

* cited by examiner

UNIPOLAR

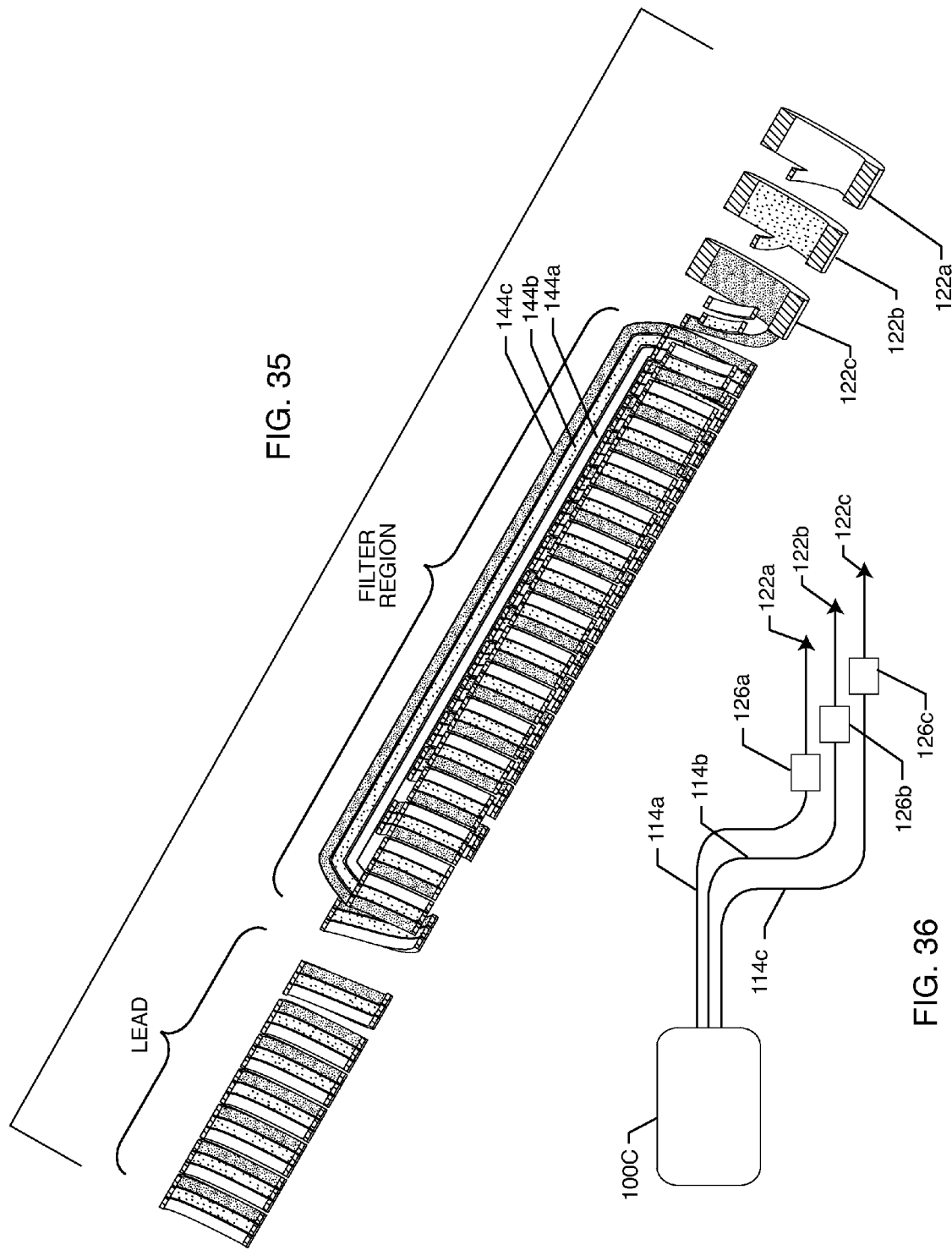

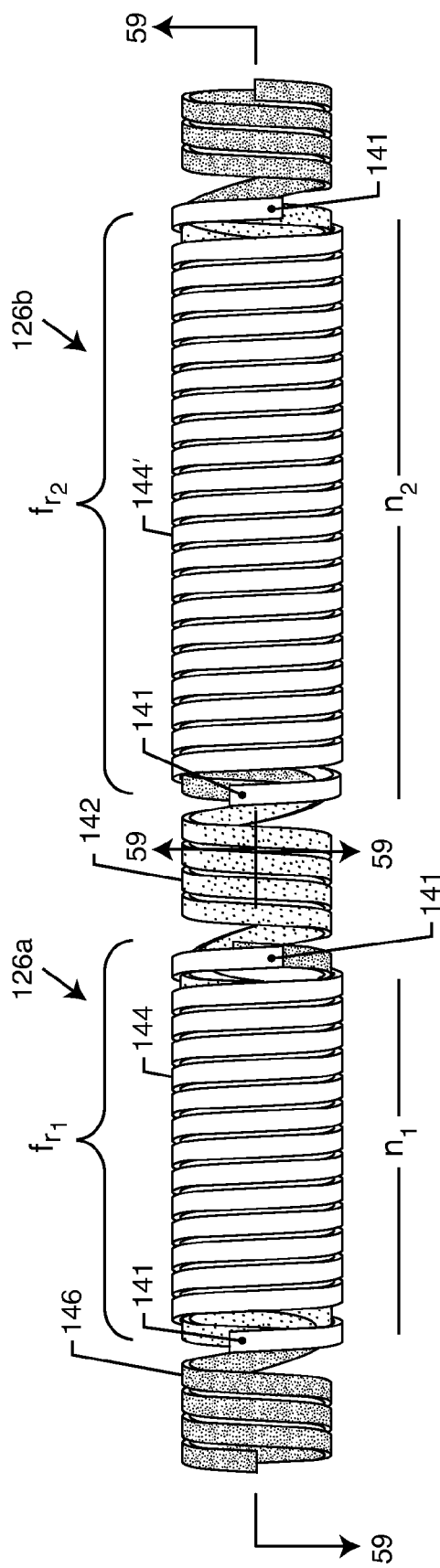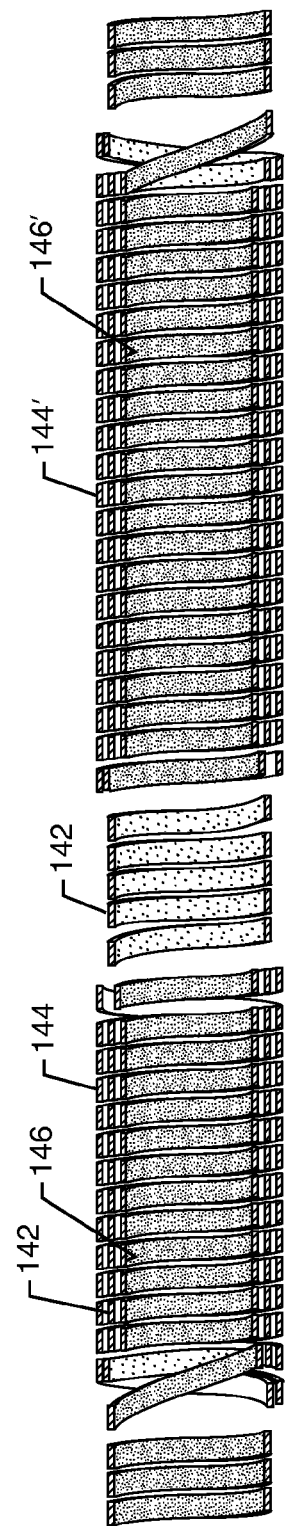
FIG. 58
FIG. 59

FIRST WHEELER LOOP

SECOND WHEELER LOOP

MULTILAYER PLANAR SPIRAL INDUCTOR FILTER FOR MEDICAL THERAPEUTIC OR DIAGNOSTIC APPLICATIONS

FIELD OF THE INVENTION

This invention generally relates to the problem of high frequency energy induced onto implanted leads during medical diagnostic procedures such as magnetic resonant imaging (MRI). More specifically, the present invention relates to an implantable medical system comprised of an active medical device (AMD) and at least one lead extending exteriorly from a proximal end at or adjacent to the AMD, to a biological sensing or stimulating electrode at a distal end. The lead has at least one multilayer helical wave filter which is designed resonate at one or more MRI RF pulsed frequencies. At resonance, the multilayer helical wave filter presents a very high impedance in the lead system which impedes RF current flow thereby preventing overheating of the lead and/or its distal electrodes during exposure to high power radio frequency (RF) fields of a particular frequency and/or frequency range.

BACKGROUND OF THE INVENTION

The radio frequency (RF) pulsed field of an MRI scanner can couple to an implanted lead in such a way that electromagnetic forces (EMFs) are induced in the lead. The amount of energy that is induced is related to a number of complex factors, but in general is dependent upon the local electric field that is tangent to the lead and the integral of the electric field strength along the lead. In certain situations, these EMFs can cause RF currents to flow into distal electrodes or in the electrode interface with body tissue. It has been documented that when this current becomes excessive, overheating of said lead or its associated electrode(s) or overheating of the associated interface with body tissue can occur. There have been cases of damage to such body tissue which has resulted in loss of capture of cardiac pacemaking pulses or tissue damage severe enough to result in brain damage or multiple amputations, and the like.

Magnetic resonance imaging (MRI) is one of medicine's most valuable diagnostic tools. MRI is, of course, extensively used for imaging, but is also used for interventional medicine (surgery). In addition, MRI is used in real time to guide ablation catheters, neurostimulator tips, deep brain probes and the like. An absolute contra-indication for pacemaker or neurostimulator patients means that these patients are excluded from MRI. This is particularly true of scans of the thorax and abdominal areas. Because of MRI's incredible value as a diagnostic tool for imaging organs and other body tissues, many physicians simply take the risk and go ahead and perform MRI on a pacemaker patient. The literature indicates a number of precautions that physicians should take in this case, including limiting the power of the MRI RF pulsed field (Specific Absorption Rate—SAR level), programming the pacemaker to fixed or asynchronous pacing mode, and then careful reprogramming and evaluation of the pacemaker and patient after the procedure is complete. There have been reports of latent problems with cardiac pacemakers or other AMDs after an MRI procedure, sometimes occurring many days later. Moreover, there are a number of papers that indicate that the SAR level is not entirely predictive of the heating that would be found in implanted leads or devices. For example, for magnetic resonance imaging devices operating at the same magnetic field strength and also at the same SAR level, considerable variations have been found relative to heating of implanted leads. It is speculated that SAR level alone is not a good predictor of whether or not an implanted device or its associated lead system will overheat.

There has been some progress in the design of active medical devices for specific use in an MRI environment under specified conditions. For example, Medtronic has received FDA approval for their REVO pacemaker, which is indicated at use for up to 2 watts per kilogram (Thorax scans excluded). St. Jude Medical and Biotronik have also received conditional approval for MRI pacemakers in Europe.

There are three types of electromagnetic fields used in an MRI unit. The first type is the main static magnetic field designated $B_0$ which is used to align protons in body tissue. The field strength varies from 0.5 to 3.0 Tesla in most of the commonly available MRI units in clinical use. Some of the newer research MRI system fields can go as high as 11.7 Tesla.

The second type of field produced by magnetic resonance imaging is the pulsed RF field which is generated by the body coil or head coil. This is used to change the energy state of the protons and elicit MRI signals from tissue. The RF field is homogeneous in the central region and has two main components: (1) the electric field which is circularly polarized in the actual plane; and (2) the H field, sometimes generally referred to as the net magnetic field in matter, which is related to the electric field by Maxwell's equations and is relatively uniform. In general, the RF field is switched on and off during measurements and usually has a frequency of 21 MHz to 64 MHz to 128 MHz depending upon the static magnetic field strength. The frequency of the RF pulse for hydrogen scans varies by the Lamour equation with the field strength of the main static field where: RF PULSED FREQUENCY in MHz=(42.56) (STATIC FIELD STRENGTH IN TESLA). There are also phosphorous and other types of scanners wherein the Lamour equation would be different. One also has to be concerned about harmonics that are produced by the MRI RF amplifier and birdcage coil of a typical MRI system. In addition to the main RF pulsed frequency, harmonics can also be deposited onto implanted leads.

The third type of electromagnetic field is the time-varying magnetic gradient fields designated $B_X$, $B_Y$, $B_Z$, which are used for spatial localization. These change their strength along different orientations and operating frequencies on the order of 1 kHz. The vectors of the magnetic field gradients in the X, Y and Z directions are produced by three sets of orthogonally positioned coils and are switched on only during the measurements.

At the frequencies of interest in MRI, RF energy can be absorbed by body tissues (or elongated conductors) and converted to heat. The power deposited by RF pulses during MRI is complex and is dependent upon the power (Specific Absorption Rate (SAR) Level) and duration of the RF pulse, the transmitted frequency, the number of RF pulses applied per unit time, and the type of configuration of the RF transmitter coil used. The amount of heating also depends upon the volume of tissue imaged, the electrical resistivity of tissue and the configuration of the anatomical region imaged. There are also a number of other variables that depend on the placement in the human body of the AMD and the length and trajectory of its associated lead(s). For example, it will make a difference how much EMF is induced into a pacemaker lead system as to whether it is a left or right pectoral implant. In addition, the routing of the lead and the lead length are also very critical as to the amount of induced current and heating that would occur.

The cause of heating in an MRI environment is twofold: (a) RF field coupling to the lead can occur which induces significant local heating; and (b) currents induced between the distal tip and tissue during MRI RF pulse transmission sequences can cause local Ohms Law heating in tissue next to the distal tip electrode of the implanted lead. The RF field of an MRI scanner can produce enough energy to induce RF voltages in an implanted lead and resulting currents sufficient to damage some of the adjacent myocardial tissue. Tissue ablation (destruction resulting in scars) has also been observed. The effects of this heating are not readily detectable by monitoring during the MRI. Indications that heating has occurred would include an increase in pacing capture threshold (PCT), venous ablation, Larynx or esophageal ablation, myocardial perforation and lead penetration, or even arrhythmias caused by scar tissue. Such long term heating effects of MRI have not been well studied yet for all types of AMD lead geometries. There can also be localized heating problems associated with various types of electrodes in addition to tip electrodes. This includes ring electrodes or pad electrodes. Ring electrodes are commonly used with a wide variety of implanted device leads including cardiac pacemakers, and neurostimulators, and the like. Pad electrodes are very common in neurostimulator applications. For example, spinal cord stimulators or deep brain stimulators can include a plurality of pad electrodes (for example, 8. 16 or 24 electrodes) to make contact with nerve tissue. A good example of this also occurs in a cochlear implant. In a typical cochlear implant there would be sixteen pad electrodes placed up into the cochlea. Several of these pad electrodes make contact with auditory nerves.

Variations in the pacemaker lead length and implant trajectory can significantly affect how much heat is generated. A paper entitled, HEATING AROUND INTRAVASCULAR GUIDEWIRES BY RESONATING RF WAVES by Konings, et al., Journal of Magnetic Resonance Imaging, Issue 12:79-85 (2000), does an excellent job of explaining how the RF fields from MRI scanners can couple into implanted leads. The paper includes both a theoretical approach and actual temperature measurements. In a worst-case, they measured temperature rises of up to 74 degrees C. after 30 seconds of scanning exposure. The contents of this paper are incorporated herein by reference.

The effect of an MRI system on the leads of pacemakers, ICDs, neurostimulators and the like, depends on various factors, including the strength of the static magnetic field, the pulse sequence, the strength of RF field, the anatomic region being imaged, and many other factors. Further complicating this is the fact that each patient's condition and physiology is different and each lead implant has a different length and/or implant trajectory in body tissues. Most experts still conclude that MRI for the pacemaker patient should not be considered safe.

It is well known that many of the undesirable effects in an implanted lead system from MRI and other medical diagnostic procedures are related to undesirable induced EMFs in the lead system and/or RF currents in its distal tip (or ring) electrodes. This can lead to overheating of body tissue at or adjacent to the distal tip.

Distal tip electrodes can be unipolar, bipolar, multipolar and the like. It is very important that excessive RF current not flow at the interface between the lead distal tip electrode or electrodes and body tissue. In a typical cardiac pacemaker, for example, the distal tip electrode can be passive or of a screw-in helix type as will be more fully described. In any event, it is very important that excessive RF current not flow at this junction between the distal tip electrode and, for example, into surrounding cardiac or nerve tissue. Excessive current at the distal electrode to tissue interface can cause excessive heating to the point where tissue ablation or even perforation can occur. This can be life-threatening for cardiac patients. For neurostimulator patients, such as deep brain stimulator patients, thermal injury can cause permanent disability or even be life threatening. Similar issues exist for spinal cord stimulator patients, cochlear implant patients and the like.

A very important and possibly life-saving solution is to be able to control overheating of implanted leads during an MRI procedure. A novel and very effective approach to this is to first install parallel resonant inductor and capacitor bandstop filters at or near the distal electrode of implanted leads. For cardiac pacemaker, these are typically known as the tip and ring electrodes. One is referred to U.S. Pat. No. 7,363,090; U.S. Pat. No. 7,945,322; U.S. Pat. No. 7,853,324; US 2008/0049376 A1; U.S. Pat. No. 7,511,921; U.S. Pat. No. 7,899,551; and U.S. Pat. No. 7,853,325A1, the contents of all of which are incorporated herein. U.S. Pat. No. 7,945,322 relates generally to L-C bandstop filter assemblies, particularly of the type used in active implantable medical devices (AIMDs) such as cardiac pacemakers, cardioverter defibrillators, neurostimulators and the like, which raise the impedance of internal electronic or related wiring components of the medical device at selected frequencies in order to reduce or eliminate currents induced from undesirable electromagnetic interference (EMI) signals.

Other types of component networks may also be used in implantable leads to raise their impedance at MRI frequencies. For example, a series inductor may be used as a single element low pass filter. The inductance will tend to look like a high impedance at high frequencies, such as the RF pulsed frequencies of a typical MRI scanner. For more information on this refer to U.S. Pat. No. 5,217,010 (Tsitlik et al.), the contents of which are incorporated herein by reference.

U.S. Pat. No. 7,363,090 and U.S. Pat. No. 7,945,322 show resonant L-C bandstop filters placed at the distal tip and/or at various locations along the medical device leads or circuits. These L-C bandstop filters inhibit or prevent current from circulating at selected frequencies of the medical therapeutic device. For example, for an MRI system operating at 1.5 Tesla, the pulsed RF frequency is 63.84 MHz, as described by the Lamour Equation for hydrogen. The L-C bandstop filter can be designed to resonate at or near 63.84 MHz and thus create a high impedance (ideally an open circuit) in the lead system at that selected frequency. For example, the L-C bandstop filter when placed at the distal tip electrode of a pacemaker lead will significantly reduce RF currents from flowing through the distal tip electrode and into body tissue. The L-C bandstop filter also reduces EMI from flowing in the leads of a pacemaker thereby providing added EMI protection to sensitive electronic circuits. In general, the problem associated with implanted leads is minimized when there is a bandstop filter placed at or adjacent to or within its distal tip electrodes.

At high RF frequencies, an implanted lead acts very much like an antenna and a transmission line. An inductance element disposed in the lead will change its transmission line characteristics. The inductance can act as its own antenna pick-up mechanism in the lead and therefore, ideally, should be shielded. When one creates a very high impedance at the distal electrode to tissue interface by installation of a resonant bandstop filter as described in U.S. Pat. No. 7,038,900 and as further described in U.S. Pat. No.

7,945,322, there is created an almost open circuit which is the equivalent of an unterminated transmission line. This causes a reflection of MRI induced RF energy back towards the proximal end where the AIMD (for example, a pacemaker) is connected. In order to completely control the induced energy in an implanted lead, one must take a system approach. In particular, a methodology is needed whereby energy can be dissipated from the lead system at the proximal end in a way that does not cause overheating either at the distal electrode interface or at the proximal end cap. Maximizing energy transfer from an implanted lead is more thoroughly described in US 2010/0160997 A1, the contents of which are incorporated herein by reference.

In order to work reliably, leads need to be stably located adjacent to the tissue to be stimulated or monitored. One common mechanism for accomplishing this has been the use of a fixation helix, which exits the distal end of the lead and is screwed directly into the body tissue. The helix itself may serve as an electrode or it may serve as an anchoring mechanism to fix the position of an electrode mounted to, or forming a portion of the lead itself.

A problem associated with implanted leads is that they act as an antenna and tend to pick up stray electromagnetic signals from the surrounding environment. This is particularly problematic in an MRI environment, where the currents which are imposed on the leads can cause the leads to heat to the point where tissue damage is likely. Moreover, the currents developed in the leads during an MRI procedure can damage the sensitive electronics within the implantable medical device. Bandstop filters, such as those described in U.S. Pat. No. 7,363,090 and US 2011/0144734 A1, reduce or eliminate the transmission of damaging frequencies along the leads while allowing the desired frequencies to pass efficiently through. Referring to U.S. Pat. No. 7,363,090, one can see that a simple L-C bandstop filter can be realized using discrete passive electronic components. This involves installing a capacitor in parallel with an inductor. As stated in U.S. Pat. No. 7,363,090 column 19, lines 59-65, "It is also possible to use a single inductive component that has significant parasitic capacitance between its adjacent turns. A careful designer using multiple turns could create enough parasitic capacitance such that the coil becomes self-resonant at a predetermined frequency. In this case, the predetermined frequency would be the MRI pulsed frequency."

Several patents describe methods of constructing leads either with inductance or with inductance that has parasitic capacitance that forms bandstop filters. These include U.S. Pat. No. 5,217,010 and U.S. Pat. No. 7,561,906. Other publications that describe inductive structures wherein parasitic capacitors form bandstop filters are US 2006/0041294, US 2008/0243218, U.S. Pat. No. 7,917,213, US 2010/0174348, US 2010/0318164, US 2011/0015713, US 2009/0281592, and US 2003/0144720.

Accordingly, there is a need for attenuating the RF energy that can be induced onto or into an implanted lead system. Moreover, there is a need for an implantable medical lead where the novel multilayer helical wave filter design presents a high impedance at MRI RF pulsed frequencies and thereby prevents dangerous overheating of the leads and/or its distal electrodes that are in contact with body tissue. The present invention fulfills these needs and provides other related advantages.

SUMMARY OF THE INVENTION

The multilayer helical wave filter of the present invention has a primary resonance at a selected RF therapeutic or diagnostic frequency or frequency range and comprises an elongated conductor which may form at least a portion of an implantable medical lead. At resonance, the multilayer helical wave filter provides a very high impedance at its resonance frequency or frequencies. In this regard, even though its equivalent circuit is more complex, the multilayer helical wave filter of the present invention performs in a similar manner to that of a simple bandstop filter consisting of a capacitor in parallel with an inductor. The elongated conductor that forms the multilayer helical wave filter has at least one planar surface and includes a first helically wound segment having a first end and a second end which forms a first inductive component, a second helically wound segment having a first end and a second end which forms a second inductive component, and a third return connecting segment which extends substantially the length of the first and second helically wound segments to connect the second end of the first helically wound segment to the first end of the second helically wound segment. The first and second helically wound segments are wound in the same longitudinal direction and share a common longitudinal axis. The at least one planar surface of the first helically wound segment faces the at least one planar surface of the second helically wound segment, and a dielectric material is disposed between the facing planar surfaces of the first and second helically wound segments and between adjacent coils of the first and second helically wound segments. Importantly, the direction of RF current flow will be the same in both the first and second helically wound segments.

In preferred embodiments, the multilayer helical wave filters, which consist of first and second helically wound segments, are disposed at or adjacent to or within one or more distal electrodes. The electrode may comprise the electrodes of cardiac pacemakers, such as a tip or a ring electrode, and may be active (helix screw-in) or passive. Furthermore, the electrodes could be neurostimulator electrodes, including electrode probe bundles, pad electrodes, ring electrodes, nerve cuff electrodes, or the like.

Inductances created by the inductive components are electrically disposed in parallel with parasitic capacitance between the first and the second helically wound segments. Further, inductance formed by the inductive components is electrically disposed in parallel with parasitic capacitance between facing planar surfaces of the first and second helically wound segments.

The elongated conductor may comprise a rectangular or a square cross-sectional configuration. The dielectric material may comprise a polyimide, a liquid crystal polymer, PTFE, PEEK, ETFE, PFA, FEP, parylene, a dielectric polymer material, or titanium oxide. It is not necessary to use only one dielectric type. In fact, an advantage of the present invention is that different dielectric materials may be used in different areas of the multilayer helical wave filter. For example, one could use one type of dielectric with a specific dielectric constant, for a portion between the first and second helically wound segments, a second dielectric with a different dielectric constant in another portion and even a third dielectric in different portion. This would change the parasitic capacitance and the resonant characteristics of the various sections of the multilayer helical wave filter. In other words, the multilayer helical wave filter could be designed to be resonant at a number of frequencies corresponding to various MRI RF pulsed frequencies and/or their harmonics.

The return connecting segment may extend inside of both the first and second helically wound segments, or the return connecting segment may extend exteriorly of both the first helically wound and second helically wound segments.

Further, the connecting segment may be coiled and again routed either exteriorly of the first and second helically wound segments, or inside of both the first and second helically wound segments. The return connecting segment may be straight or curvilinear. Since the induced RF current is reversed in the return segment, it is important that the return connecting segment not be extended between the first helically wound segment and the second helically wound segment.

In various embodiments, one of the helically wound segments is disposed radially inside the other, or the first and second helically wound segments are co-radially disposed about the common longitudinal axis in a side-by-side relationship.

In another embodiment, a third helically wound segment has a first end and a second end and forms a third inductive component. The first, second and third helically wound segments are wound in the same longitudinal direction, wherein a planar surface of the third helically wound segment faces a planar surface of the second helically wound segment. The elongated conductor includes a second connecting segment extending substantially the length of the second and third helically wound segments to connect the second end of the second helically wound segment to the first end of the third helically wound segment. A dielectric material is disposed between facing planar surfaces of the second and third helically wound segments.

In yet another embodiment of the multilayer helical wave filter of the present invention, a second elongated conductor is provided, which has at least one planar surface and comprises (1) a first helically wound segment having a first end and a second end and forming a first inductive component, (2) a second helically wound segment having a first end and a second end and forming a second inductive component, and (3) a return connecting segment extending substantially the length of the first and second helically wound segments to connect the second end of the first helically wound segment to the first end of the second helically wound segment. The first and second helically wound segments are wound in the same longitudinal direction and share a common longitudinal axis, wherein the at least one planar surface of the first helically wound segment faces the at least one planar surface of the second helically wound segment. The return connecting segment provides that current paths in first and second helically wound segments will be in the same direction. One or more dielectric materials are disposed between the facing planar surfaces of the first and second helically wound segments, and between adjacent coils of the first and second helically wound segments. This second elongated conductor provides that the wave filter has both a first and a secondary primary resonance at selected MRI pulsed frequencies or frequency ranges.

The inductance created by the inductive components of the second elongated conductor is electrically disposed in parallel with parasitic capacitance between the first and the second helically wound segments. Moreover, the inductance formed by the inductive components of the second elongated conductor is electrically disposed in parallel with parasitic capacitance between facing planar surfaces of the first and second helically wound segments.

The elongated conductors are wound in the same longitudinal direction and share the same longitudinal axis, which means that the RF current paths in the elongated conductors of all helically wound segments are in the same direction. The second elongated conductor further comprises a rectangular or a square cross-sectional configuration.

The return connecting segment of the second elongated conductor extends within or exteriorly of both the first helically wound segment and the second helically wound segment. The return connecting segment of the second elongated conductor may further be coiled exteriorly or interiorly of both the first and second helically wound segments.

In various configurations, one of the helically wound segments of the second elongated conductor may be disposed radially inside the other, or the first and second helically wound segments of the second elongated conductor may be co-radially disposed about the common longitudinal axis in a side-by-side relationship. One may also vary the pitch of the helical winding of the first segment and/or the pitch of the second segment in order to vary the inductance and parasitic capacitance. By varying the pitch along the length of the multilayer helical wave filter, one can create multiple resonances. For example, one could create a resonance at the RF pulsed frequency of a 1.5 Tesla MRI scanner and also a second or even third resonance at its harmonics at 128 and 192 MHz.

Preferably, the multilayer helical wave filter has a Q at resonance wherein the resultant 10 dB bandwidth is at least 10 KHz. In various embodiments, the Q at resonance may be at least 100 KHz and in other embodiments at least 0.5 MHz. By controlling the dielectric type, the dielectric constant of the dielectric material may be varied from 2 to 50.

The primary resonance of the wave filter may comprise a plurality of selective MRI RF pulsed frequencies or frequency ranges, and the wave filter may resonate at the selected RF frequency or frequency range and also at one or more of its harmonic frequencies.

The first helically wound segment may have a different cross-sectional area than the second helically wound segment. Moreover, the first helically wound segment may have a different number of turns than the second helically wound segment.

Electric insulation is typically provided for attenuating RF currents and body fluids or tissues from degrading the impedance of the wave filter at resonance. The insulation is typically continuous with an overall insulation of the implantable medical lead, and may include an insulative sleeve disposed about the elongated conductor.

Other features and advantages of the present invention will become apparent from the following more detailed description, taken in conjunction with the accompanying drawings which illustrate, by way of example, the principles of the invention.

An exemplary embodiment of the present invention (best shown in FIGS. 75-91) discloses a multilayer and multihelical Wheeler spiral bandstop filter configured to be connectable in series with an implantable lead of an active implantable medical device, probe or catheter. A first conductive circuit trace is configured to form a first Wheeler spiral inductor with a first multi-turn loop current loop current. A second conductive circuit trace is configured to form a second Wheeler spiral inductor with a second multi-turn loop current. The second conductive circuit trace is configured to be substantially similar in pattern to the first conductive circuit trace. The first and second Wheeler spiral inductors are in a stacked relationship with a dielectric substrate there between. A center of each first and second Wheeler spiral inductors are electrically coupled. The first multi-turn loop current of the first Wheeler spiral inductor is in the same direction as the second multi-turn loop current of the second Wheeler spiral inductor.

In other exemplary embodiments, a bandstop filter inductance is configured to be formed by the first and second Wheeler spiral inductors. A bandstop filter capacitance including parasitic capacitance is configured to be formed between adjacent turns of each Wheeler spiral inductor or between adjacent turns of the first and second Wheeler spirals inductors. The bandstop filter inductance and bandstop filter capacitance may include an equivalent circuit bandstop filter. The equivalent circuit bandstop filter is configured to attenuate an MRI RF pulsed frequency at or near an RF resonant selected center frequency. The RF resonant selected center frequency may be 64 MHz or 128 MHz.

The first and second conductive circuit traces may be circular, rectangular, square, oval, pentagon, hexagon or irregular shaped.

The dielectric substrate and first and second conductive circuit traces may be flexible. The dielectric substrate may be configured to form into a roll.

An insulative covering may be disposed over an outside of the first and second conductive circuit traces.

A third conductive circuit trace may be configured to form a third Wheeler spiral inductor configured to be substantially similar in pattern to the first and second Wheeler spiral inductors. The second and third Wheeler spiral inductors may be in a stacked relationship with a second dielectric there between. An outside end of each second and third Wheeler spiral inductors may be electrically coupled. The first multi-turn loop current of the first Wheeler spiral inductor, the second multi-turn loop current of the second Wheeler spiral inductor and a third multi-turn loop current of the third Wheeler spiral inductor may be in the same direction.

A fourth conductive circuit trace may be configured to form a fourth Wheeler spiral inductor configured to be substantially similar in pattern to the first, second and third Wheeler spiral inductors. The third and fourth Wheeler spiral inductors may be in a stacked relationship with a third dielectric there between. A center of each third and fourth Wheeler spiral inductors may be electrically coupled. The first multi-turn loop current of the first Wheeler spiral inductor, the second multi-turn loop current of the second Wheeler spiral inductor, the third multi-turn loop current of the third Wheeler spiral inductor and a fourth multi-turn loop current of the fourth Wheeler spiral inductor may be in the same direction.

An embodiment may include an n number of conductive circuit traces configured to form an n number of Wheeler spiral inductors configured to be substantially similar in pattern to the first, second, third and fourth Wheeler spiral inductors.

The first and second conductive circuit traces may be first formed on a same side of the dielectric substrate and subsequently folded to be in the stacked relationship.

A first contact pad may be electrically coupled to an outside end of the first conductive circuit trace. A second contact pad may be electrically coupled to an outside end of the second conductive circuit trace.

The first and second contact pads may be configured to be connectable to the implantable lead.

The first Wheeler spiral inductor may attenuate a first MRI RF pulsed frequency at or near a first RF resonant selected center frequency or range of frequencies. The second Wheeler spiral inductor may attenuate a second MRI RF pulsed frequency at or near a second RF resonant selected center frequency or range of frequencies. The first and second RF resonant selected center frequencies may be substantially different frequencies. The first RF resonant selected frequency may be 64 MHz and the second RF resonant selected center frequency may be 128 MHz.

The dielectric substrate may include a tape-based flexible base. The first and second conductive circuit traces may be manufactured using a spin coating, a conventional sputter process, an evaporation technique, a photoresist process, an etching process, a photoresist removal process, a silk-screening process or an electrically deposited process.

An exemplary embodiment of the present invention (best shown in FIGS. 47-49) discloses a multilayer helical bandstop filter configured to be connectable in series with an implantable lead of an active implantable medical device, probe or catheter. An insulated electrical conductor is configured to form a first helically wound inductor segment, a return helically wound inductor segment and a second helically wound inductor segment wherein the segments overlap each other along a common length and wherein the second helically wound inductor segment is disposed between the first and return helically wound inductor segments. The first and second helically wound inductor segments include a self-resonant inductor where a bandstop filter inductance is configured to be formed by the helically wound inductor segments and where a bandstop filter capacitance including parasitic capacitance is configured to be formed between adjacent turns of each segment or between adjacent turns of different segments. The first and second helically wound inductor segments are wound in the same longitudinal direction and same rotation and wherein the return helically wound inductor segment is wound in an opposite direction and same rotation as compared to the first and second helically wound inductor segments.

The multilayer helical bandstop filter may attenuate an MRI RF pulsed frequency. The MRI RF pulsed frequency may include 64 MHz or 128 MHz.

The first helically wound inductor segment, the return helically wound inductor segment and the second helically wound inductor segment may include a hollow center portion configured for convenient guidewire insertion.

The bandstop filter inductance or capacitance may be configured to be tuned by changing the number of turns of the return helically wound inductor segment.

As shown best in FIG. 54, the first and second helically wound inductor segments each include a D-shaped wire, wherein a flat side of each D-shaped wire abuts the other flat side.

As shown best in FIGS. 60-61, a first crimp structure may electrically connect the first helically wound inductor segment to the return helically wound inductor segment. A second crimp structure may electrically connect the second helically wound inductor segment to the return helically wound inductor segment. A third crimp structure may electrically connect either the first or second helically wound inductor segment to a lead conductor.

As best shown in FIGS. 62-66, the first and second helically wound inductor segments may include a double insulated wire. The return helically wound inductor segment may include a single insulated wire electrically coupled at one end to the first helically wound inductor segment and coupled at the other end to the second helically wound inductor segment. The double insulated wire may include two circular shaped wires, two D-shaped wires, two rectangular wires, two square wires or two oval wires. The first and second helically wound inductor segments may be co-radial where the first helically wound inductor segment is disposed adjacent to the second helically wound inductor segment.

An exemplary embodiment of the present invention (best shown in FIGS. 55-56) discloses a multilayer and multisection helical bandstop filter configured to be connectable in series with an implantable lead of an active implantable medical device, probe or catheter. An insulated electrical conductor is configured to form at least a first and second discrete bandstop filter including a common inner helically wound inductor segment. The first discrete bandstop filter includes a first set of turns of the common inner helically wound inductor segment, a first return helically wound inductor segment and a first outer helically wound inductor segment each overlapping along a first common length. The second discrete bandstop filter includes a second set of turns of the common inner helically wound inductor segment, a second return helically wound inductor segment and a second outer helically wound inductor segment each overlapping along a second common length. The common inner helically wound inductor segment is continuous along the first and second common lengths.

In other embodiments, the first outer helically wound inductor segment may be disposed between the first set of turns of the common inner helically wound inductor segment and the first return helically wound inductor segment.

The second outer helically wound inductor segment may be disposed between the second set of turns of the common inner helically wound inductor segment and the second return helically wound inductor segment.

The first discrete bandstop filter may include a second self-resonant inductor where a second bandstop filter inductance is configured to be formed by the helically wound inductor segments along the first common length and where a second bandstop filter capacitance including parasitic capacitance is configured to be formed between adjacent turns of each segment or between adjacent turns of different segments along the first common length.

The second discrete bandstop filter may include a second self-resonant inductor where a second bandstop filter inductance is configured to be formed by the helically wound inductor segments along the second common length and where a second bandstop filter capacitance including parasitic capacitance is configured to be formed between adjacent turns of each segment or between adjacent turns of different segments along the second common length.

The common inner helically wound inductor segment, the first outer helically wound inductor segment and the second outer helically wound inductor segments may be wound in the same longitudinal direction and rotation.

The first and second return helically wound inductor segments may be wound in an opposite direction and same rotation as compared to the common inner helically wound inductor segment.

The first discrete bandstop filter may attenuate a first MRI RF pulsed frequency at or near a first RF resonant selected center frequency or range of frequencies. The second discrete bandstop filter may attenuate a second MRI RF pulsed frequency at or near a second RF resonant selected center frequency or range of frequencies. The first and second RF resonant selected center frequencies may be substantially different frequencies. The first RF resonant selected frequency may be 64 MHz and the second RF resonant selected center frequency may be 128 MHz.

An exemplary embodiment of the present invention (best shown in FIGS. 58-59) discloses a multilayer and multisection helical bandstop filter configured to be connectable in series with an implantable lead of an active implantable medical device, probe or catheter. An insulated electrical conductor is configured to form at least a first and second discrete bandstop filter including a common outer helically wound inductor segment. The first discrete bandstop filter includes a first set of turns of the common outer helically wound inductor segment, a first return helically wound inductor segment and a first inner helically wound inductor segment overlapping along a first common length. The second discrete bandstop filter includes a second set of turns of the common outer helically wound inductor segment, a second return helically wound inductor segment and a second inner helically wound inductor segment overlapping along a second common length. The common outer helically wound inductor segment is continuous along the first and second common lengths.

In other embodiments, the first set of turns of the common outer helically wound inductor segment may be disposed between the first inner helically wound inductor segment and the first return helically wound inductor segment.

The second set of turns of the common outer helically wound inductor segment may be disposed between the inner helically wound inductor segment and the second return helically wound inductor segment.

The first discrete bandstop filter may include a self-resonant inductor where a bandstop filter inductance is configured to be formed by the helically wound inductor segments along the first common length and where a bandstop filter capacitance including parasitic capacitance is configured to be formed between adjacent turns of each segment or between adjacent turns of different segments along the first common length.

The second discrete bandstop filter includes a second self-resonant inductor where a second bandstop filter inductance is configured to be formed by the helically wound inductor segments along the second common length and where a second bandstop filter capacitance including parasitic capacitance is configured to be formed between adjacent turns of each segment or between adjacent turns of different segments along the second common length.

The common outer helically wound inductor segment, the first inner helically wound inductor segment and the second inner helically wound inductor segments may be wound in the same longitudinal direction and rotation.

The first and second return helically wound inductor segments may be wound in an opposite direction and same rotation as compared to the common outer helically wound inductor segment.

The first discrete bandstop filter may attenuate a first MRI RF pulsed frequency at or near a first RF resonant selected center frequency or range of frequencies. The second discrete bandstop filter may attenuate a second MRI RF pulsed frequency at or near a second RF resonant selected center frequency or range of frequencies. The first and second RF resonant selected center frequencies may be substantially different frequencies. The first RF resonant selected frequency may include 64 MHz and the second RF resonant selected center frequency may include 128 MHz.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 35 is a sectional view taken generally along line 35-35 from FIG. 34;

FIG. 36 is an electrical schematic illustration of the structure shown in FIGS. 34 and 35;

FIG. 58 is a multi-section and multilayer helical bandstop with a continuous outer coil;

FIG. 59 is a sectional view of the structure of FIG. 58 taken along lines 59-59;

DETAILED DESCRIPTION OF THE PREFERRED EMBODIMENTS

Figure 1:
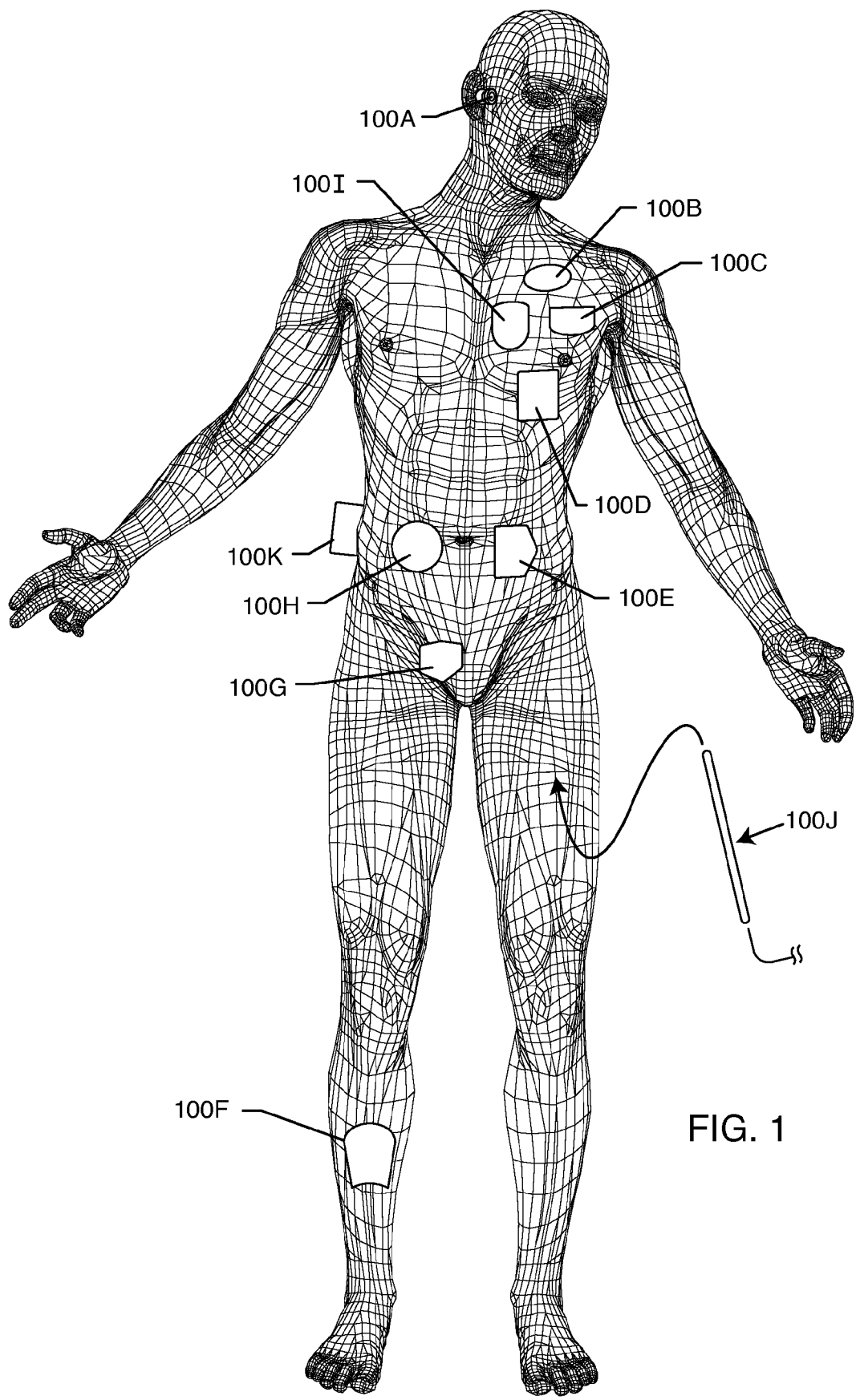
FIG. 1 is a wire-formed diagram of a generic human body showing a number of exemplary active medical devices (AMDs)

As shown in the drawings for purposes of illustration, the present invention relates to multilayer helical wave filters placed between proximal and distal ends of an implantable lead of an active medical device (AMD). One or more multilayer helical wave filters may be implanted anywhere along the length of implanted leads or electrodes of AMDs. In particular, the multilayer helical wave filter of the present invention presents a very high impedance (which impedes RF current flow) at one or more MRI RF pulsed frequencies. The present invention is particularly important to protect implanted leads from overheating in the presence of high power electromagnetic field environments, such as the RF pulsed fields produced by a clinical MRI scanner. In a broad sense, the present invention comprises a multilayer helical wave filter which is installed in one or more locations along the length of the conductors of an implanted lead. As will be shown, it is also very important that the multilayer helical wave filter be insulated along its entire length with insulation integral to the implanted lead so that RF leakage paths do not occur around the filter through ionic body fluids.

The multilayer helical wave filter of the present invention acts as an impeding circuit. The operation of impeding circuits and diversion circuits is more thoroughly described in U.S. Pat. No. 7,751,903 and US 2010/0160997 A1, which are incorporated herein by reference. In a particularly preferred embodiment, the multilayer helical wave filter has a Q and 3-dB bandwidth such that, at resonance, it offers attenuation of at least 10-dB over a range of MRI RF pulsed frequencies at least 10 kHz wide, and more preferably at least 100 kHz or even on the order of MHz. The novel multilayer helical wave filter of the present invention can be used in combination with any of the diversion circuits as described in U.S. Pat. No. 7,751,903 and US 2010/0160997 A1.

In the case where a multilayer helical wave filter is installed at or near the distal electrode of an implanted lead, the RF energy induced by the MRI pulse field is inhibited from flowing into body tissues. However, even when a distal electrode multilayer helical wave filter is used, the induced RF energy still resides in the lead system. In other words, by preventing this induced energy from flowing to sensitive tissues at distal electrode interfaces, a great deal has been accomplished; however, it is still important to carefully dissipate the remaining energy that is trapped in the lead system. Dissipation of the RF energy that's reflected off of a distal tip electrode filter is more thoroughly described in US 2010/0217262 A1 which is incorporated herein by reference. US 2010/0217262 reference teaches how to dissipate energy to the relatively large surface area of the AIMD housing thereby safely removing it from the lead system.

FIG. 1 is a wire formed diagram of a generic human body showing a number of exemplary implantable medical devices. 100A is a family of implantable hearing devices which can include the group of cochlear implants, piezoelectric sound bridge transducers and the like. 100B includes an entire variety of neurostimulators and brain stimulators. 100C shows a cardiac pacemaker. 100D includes the family of left ventricular assist devices (LVAD's) and artificial hearts. 100E includes an entire family of drug pumps which can be used for dispensing of insulin, chemotherapy drugs, pain medications and the like. 100F includes a variety of implantable bone growth stimulators for rapid healing of fractures. 100G includes urinary incontinence devices. 100H includes the family of pain relief spinal cord stimulators and anti-tremor stimulators. 100I includes a family of implantable cardioverter defibrillator (ICD) devices, congestive heart failure devices (CHF), and cardio resynchronization therapy devices, otherwise known as CRT devices. 100J illustrates a family of probes or catheters that can be transvenously inserted during catheter lab procedures. These are normally considered short-term implants in that they are inserted within the human body for at most a few hours. 100K is an externally worn active medical device, such as a neurostimulator. It can be worn on a belt, placed in a pocket or the like. Typically, it has one or more implanted leads. 100K also represents an externally worn drug pump or the like.

The various types of active medical devices (AMDs) illustrated in FIG. 1 generally represent any type of AMD that is either a "long-term" or "short-term" implant. "Short-term" implants include AMDs like probes or catheters or surgical devices that are "short-term" body insertions used either for diagnostic or therapy delivery purposes. For example, a probe or catheter is typically used in a cath-lab situation wherein it is temporarily inserted through a femoral (or other) artery where the entire procedure lasts minutes or at most a few hours. On the other hand, a long-term implant, such as a cardiac pacemaker, is generally designed to be implanted in the human body for many years. There are significant differences in the art between a short-term and a long-term implant. For example, for a long-term implant, one has to worry greatly about the long-term biocompatibility, toxicity and even the hermeticity of the implant. In contrast, a probe, catheter or temporary loop recorder need only operate or be reliable for a matter of minutes or even hours. In general, a short-term implant is often considered to be a disposable device. In addition, the FDA regulatory approval processes for long-term implants is significantly different and involves much more rigorous testing and product safety and reliability criteria. The FDA Center for Devices and Radiological Health (FDA-CDRH) is the responsible regulatory agency for long-term cardiac implants. As used herein, the term active medical device (AMD) or active implantable medical device (AIMD) is construed to include long-term implants and also short-term body insertions, such as probes or catheters. The term AMD is inclusive of active implantable medical devices (AIMDs) and also externally worn medical devices that are associated with an implanted lead.

Throughout, the term lead generally refers to implantable leads and their conductors that are external to the housing of the active medical device. These leads tend to have a proximal end, which is at or adjacent to the AMD, and a distal end, which typically includes one or more electrodes which are in contact with body tissue.

Figure 2:
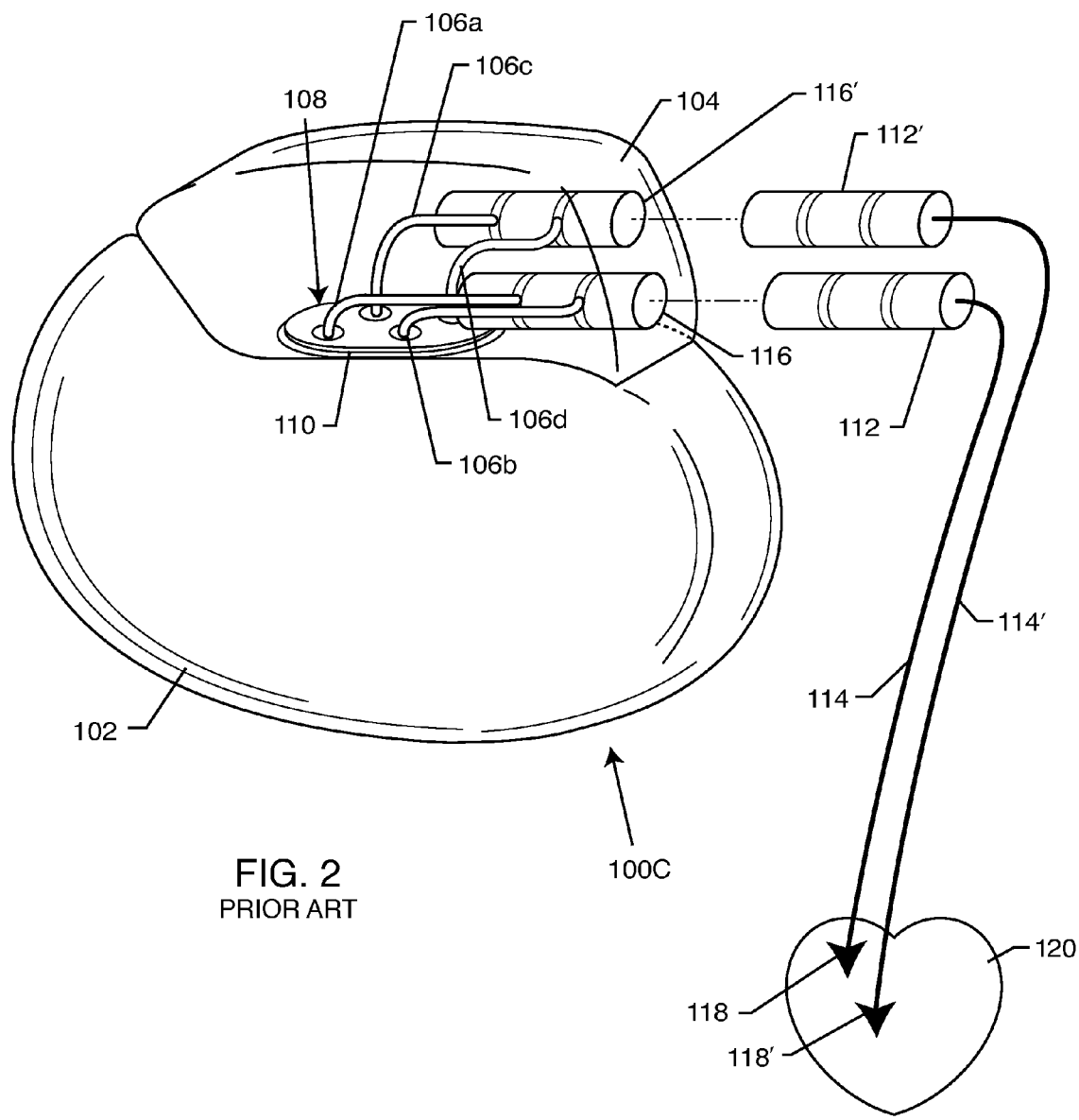
FIG. 2 illustrates an exemplary prior art cardiac pacemaker with the leads schematically shown extending to a patient's heart.

FIG. 2 is a drawing of a typical cardiac pacemaker 100C showing a titanium case or housing 102 and an IS-1 header connector block 104. The titanium case or housing 102 is hermetically sealed, however there is a point where leadwires 106a-106d must ingress and egress a hermetic seal. This is accomplished by providing a hermetic terminal assembly 108 that generally consists of a ferrule 110 which is laser welded to the titanium housing 102 of the pacemaker 100C.

Four leadwires are shown consisting of leadwire pair 106a and 106b and leadwire pair 106c and 106d. This is typical of what is known as a dual chamber bipolar cardiac pacemaker. The IS-1 connectors 112 and 112' of leads 114 and 114' are designed to plug into receptacles 116 and 116' in the header block 104. The receptacles 116 and 116' are low voltage (pacemaker) connectors covered by an ANSI/AAMI ISO standard IS-1. Higher voltage devices, such as implantable cardioverter defibrillators (ICDs), are covered by ANSI/AAMI ISO standard DF-1. A new standard which will integrate both high voltage and low voltage connectors into a miniature in-line quadripolar connector is known as the IS-4 series. The implanted leads 114 and 114' are typically routed transvenously in a pacemaker application down into the right atrium 118 and the right ventricle 118' of the heart 120. New generation biventricular or CRT-P devices may introduce leads to the outside of the left ventricle, which devices have proven to be very effective in cardiac resynchronization and treating congestive heart failure (CHF).

Although the present invention will be described herein in the context and environment of a cardiac pacemaker 100C and its associated leads 114 and 114', the present invention may also be advantageously utilized in many other types of AMDs as briefly outlined above and shown in FIG. 1, as well as in other commercial electronic, military, aerospace and other applications. In the following discussion, to the extent practicable, functionally equivalent components will retain the same or a similar reference number, irrespective of the particular embodiment being described.

Figure 3:
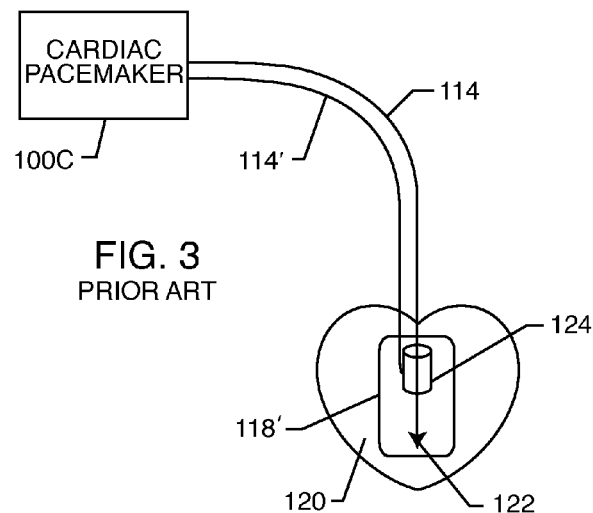
FIG. 3 is a schematic illustration of a prior art AMD with a bipolar lead.

FIG. 3 illustrates a prior art single chamber bipolar AMD 100C and lead system 114 and 114' with a distal tip electrode 122 and a ring electrode 124 typically as used with a cardiac pacemaker 100C. Should the patient be exposed to the fields of an MRI scanner or other powerful emitter used during a medical diagnostic procedure, currents that are directly induced in the lead system 114, 114' can cause heating by $I^2R$ losses in the lead system or by heating caused by RF current flowing from the tip and ring electrodes 122, 124 into body tissue. If these induced RF currents become excessive, the associated heating can cause damage or even destructive ablation to body tissue.

Figure 4:
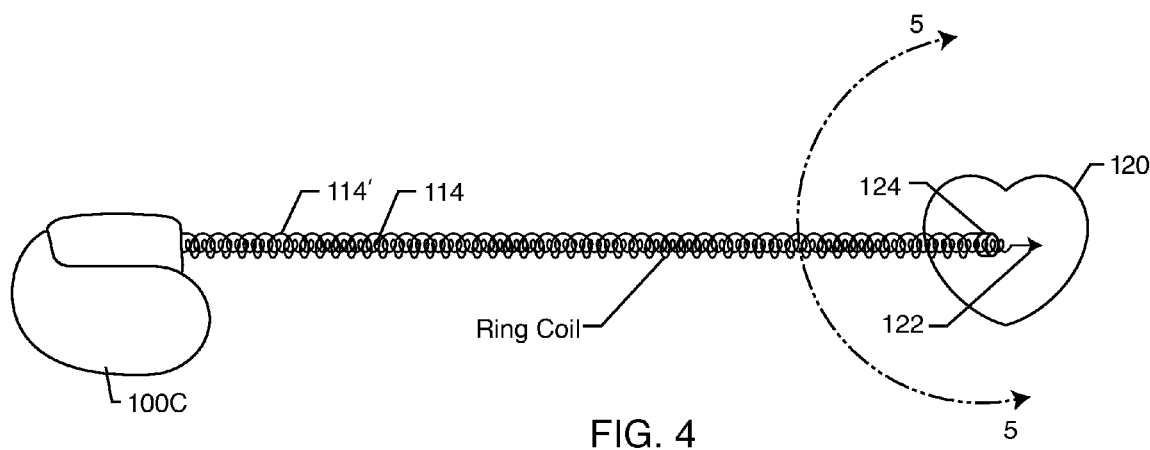
FIG. 4 is similar to FIG. 3, except that the bipolar lead wires are coaxially wound around one another.

FIG. 4 illustrates a single chamber bipolar cardiac pacemaker 100C, and leads 114 and 114' having distal tip 122 and distal ring 124 electrodes. This is a spiral wound (coaxial) system where the ring coil 114' is wrapped around the tip coil 114. There are other types of pacemaker leadwire systems in which these two leads lay parallel to one another (known as a bifilar lead system), which are not shown.

Figure 5:
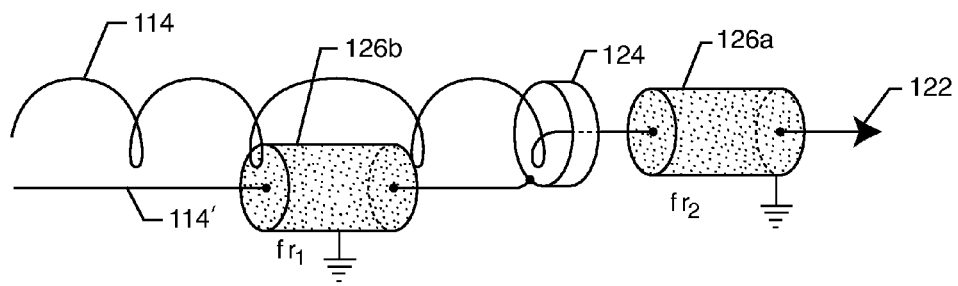
FIG. 5 is an enlarged view of the area indicated by line 5-5 from FIG. 4, illustrating wave filters associated with both the tip and ring electrodes.

FIG. 5 is taken from section 5-5 of FIG. 4, and shows multilayer helical wave filters 126a and 126b. As illustrated, there is a multilayer helical wave filter 126a of the present invention at or adjacent to the tip electrode 122 also a multilayer helical wave filter 126b at the ring electrode 124. In general, the multilayer helical wave filters 126, would be tuned to be resonant at a center frequency in a range of MRI RF pulsed frequencies. The operation of simple L-C bandstop filters in implanted leads is more thoroughly described by U.S. Pat. No. 7,363,090 and U.S. Pat. No. 7,945,322. The performance of the multilayer helical wave filter 126 of the present invention is similar to that of a simple L-C bandstop filter, except that its equivalent circuit diagram is much more complicated. In addition, unlike a simple L-C bandstop filter, the multilayer helical wave filter can be designed with multiple resonances as described herein. It is useful to think of these multiple resonances as equivalent to multiple bandstop filters of varying resonant frequencies that are disposed in series with the implanted lead.

Figure 6:
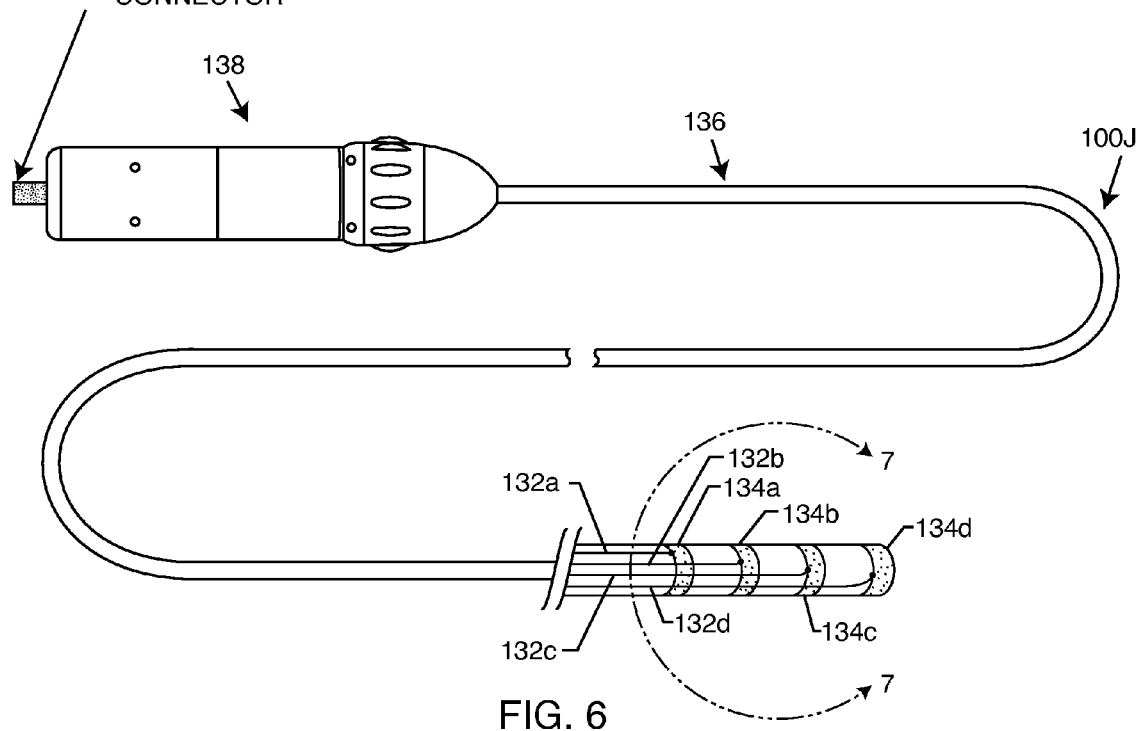
FIG. 6 illustrates a probe or catheter which has four distal electrodes.

FIG. 6 illustrates a probe or a catheter 100J which has four internal conductors 132a-132d which are directed to four different distal electrodes 134a-134d at its distal end. In the art, electrode 134d would be known as an ablation electrode wherein the other electrodes could be used for cardiac electrical mapping and the like. The probe or catheter 100J encompasses multilayer helical wave filters 126a-126d of the present invention in series with each of the conductors that are directed to the electrodes 134a-134d. The probe or catheter 100J consists of a flexible and steerable probe or catheter section 136 which may be bent as shown and generally terminates in the distal electrodes 134a-134d. There is generally a catheter handle or body 138 which is used for steering the probe or catheter into the body transvenously. These handles can take the form of a pistol grip or many other shapes.

Figure 7:
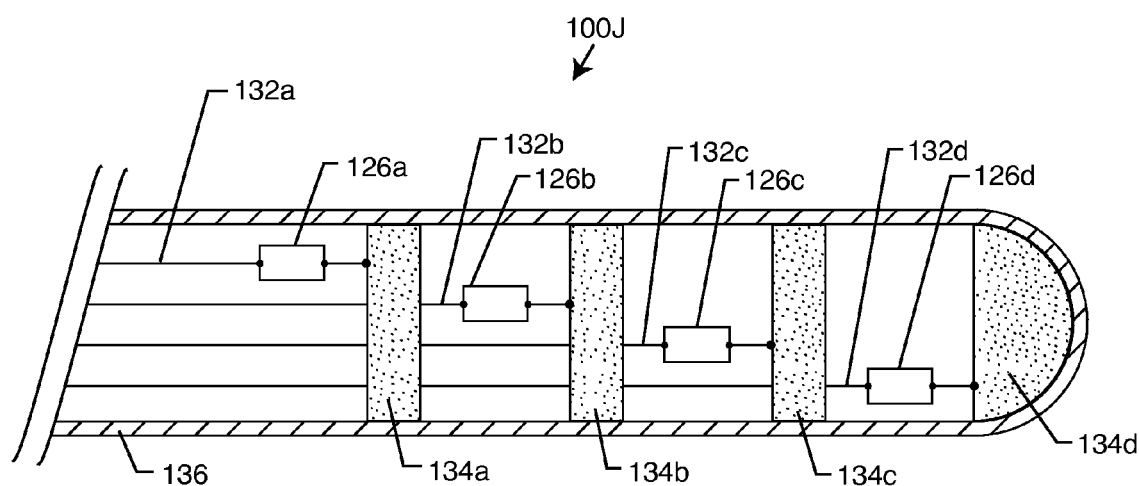
FIG. 7 is an enlarged view of the distal tip section of the probe or catheter of FIG. 6.

FIG. 7 is a sectional view taken generally along section 7-7 from FIG. 6. Shown are the four conductors 132a-132d which are housed inside the probe or catheter steerable body 136. There are four multilayer helical wave filter 126a-126d in accordance with the present invention. Each of these multilayer helical wave filters 126 is in series with one of the distal electrodes 134. These multilayer helical wave filters 126 impede MRI RF induced currents from flowing into the electrodes 134 and thereby inadvertently overheating and damaging adjacent living tissues.

Figure 8:
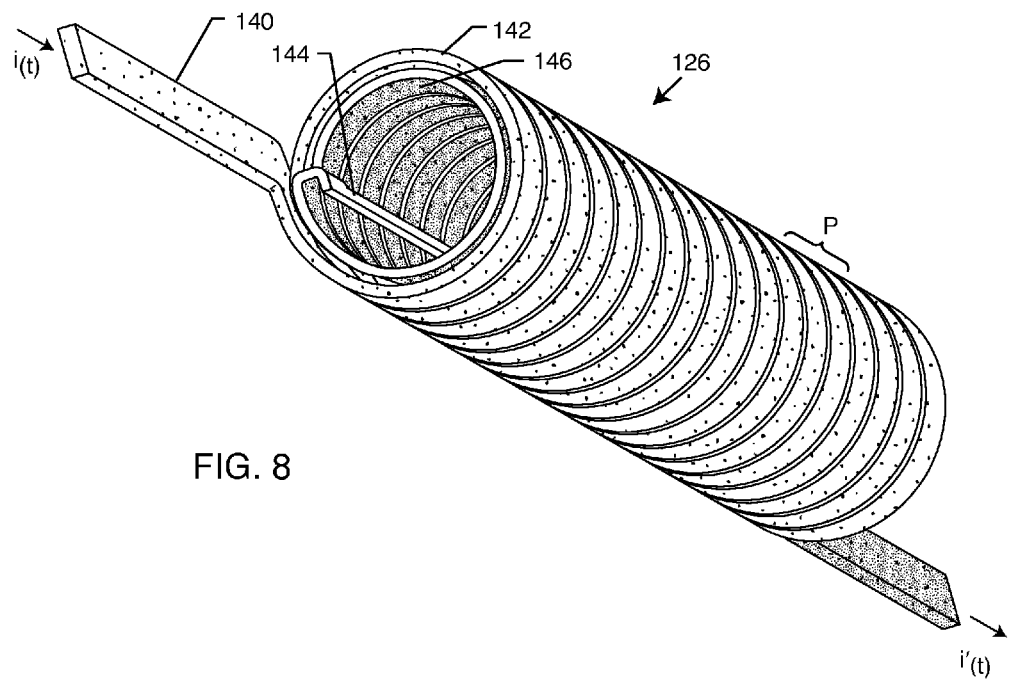
FIG. 8 is an isometric view of a multilayer helical wave filter embodying the present invention.

FIG. 8 is an isometric view of a multilayer helical wave filter 126 of the present invention which is in series with an implanted lead (not shown). Also not shown is an overall insulation covering the multilayer helical wave filter which is contiguous with the implanted lead to provide isolation of the multilayer helical wave filter from body fluids. This insulation is omitted for clarity purposes in many of the drawings, however, it will be understood that this insulation is essential so that the impedance of the multilayer helical wave filter at resonance is not degraded by parallel RF current paths through body tissues. Shown is an elongated rectangular conductor 140 with an MRI RF induced current $i_{(t)}$ shown entering it. The elongated conductor 140 forms a first helically wound inductor segment 142. Then there is a return wire connecting segment 144 (which could be coiled) which is used to wind a second helically wound inductor 146 inside of the first segment. Accordingly, the first helically wound inductor segment 142 and the second helically wound inductor segment 146 are wound in the same longitudinal direction and share a common longitudinal axis where planar surfaces of the first helically wound segment 142 face or abut planar surfaces of the second helically wound inductor segment 146. In general, the elongated conductor has a dielectric insulation which may also be used to insulate the entire multilayer helical wave filter such that RF current through body fluids do not degrade its impedance at resonance. A capacitance is therefore formed between the planar surfaces of the first helically wound inductor segment 142 and the second helically wound inductor segment 146. There is also a capacitance that is formed between adjacent turns. The effect of these inductor segments and capacitances will be to form a helical wave filter 126 in accordance with the present invention. There are a number of advantages to the multilayer helical wave filter construction as illustrated in FIG. 8. First of all, by using biocompatible materials, there is no need for discrete components placed inside of a hermetic seal. One is referred to US 2010/0231237 for a description of how discrete passive capacitors and inductors are placed inside a hermetically sealed housing to form a bandstop filter. This package is both large and very expensive to produce. It will be apparent that the multilayer helical wave filter 126 of the present invention is both volumetrically efficient and relatively much lower in cost.

Figure 9:
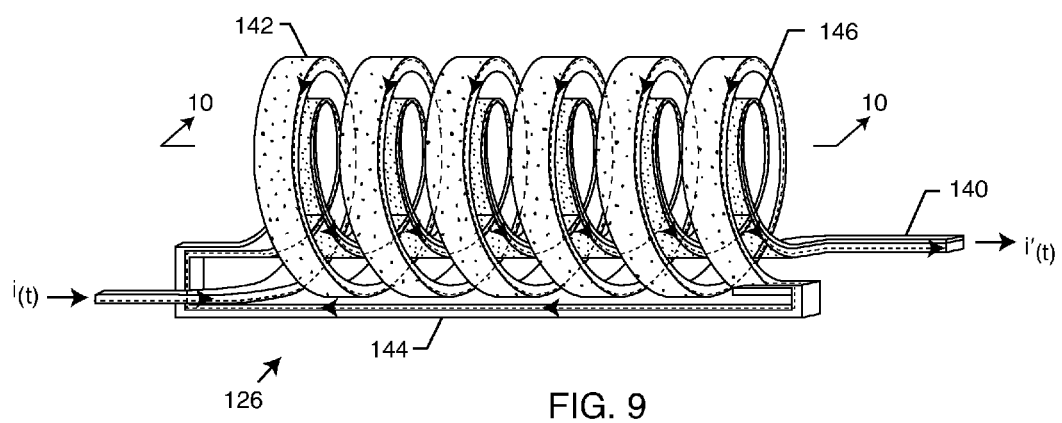
FIG. 9 is a partially schematic view of the structure shown in FIG. 8, wherein the first helically wound segment is much larger in diameter than the second helically wound segment for illustrative purposes.

FIG. 9 is very similar to FIG. 8 except that the first helically wound segment 142 is much larger in diameter than the second helically wound inductor segment 146. This is to better illustrate the principles of the present invention and also indicate the direction of current flow. As one can see, in both the first (outer) helical wound inductor segment 142 and the second (inner) helically wound inductor segment 146, the RF induced current flow from MRI is always in the same direction. Having the current flow be in the same direction of the various inductor segments of the present invention is critically important and a major distinguishing feature over the prior art. Having the RF current flow in the same direction increases the inductance by up to a factor of four times as compared to having a single inductor winding. Current flow in the same direction results in much stronger effective fields as opposed to field reduction in the case of opposite current flows in adjacent turns. The design of the return wire or segment 144, which can be straight, curvilinear or coiled, (and also be either external or internal to the inductor segments) is a key. In the prior art, which teaches parasitic inductance to form simple bandstop filters, the current flow of adjacent coils is generally in opposite directions (reference Bottomley US 2008/0243218 A1). In the present invention, the fields associated with the return wire or segments 144 are negligible in comparison with the fields generated by both the inner and outer multilayer helical inductor segments 142 and 146.

Referring once again to FIG. 8, one could also vary the pitch between adjacent turns of portions of the multilayer helical wound wave filter 126. This would create sections that had a different resonant frequency as compared to other sections. Accordingly, it is a feature of the present invention that the multilayer helical wave filter 126 can be resonant at 1, 2 or even "n" number of selected RF frequencies. Similar effects can be achieved by carefully controlling the overlap area between the planar surfaces of the outer inductor segment 142 and the inner inductor segment 146. This would affect the amount of parasitic capacitance and hence the resonant frequency. It is also possible to control this parasitic capacitance by controlling the dielectric thickness or the dielectric type in various sections of the multilayer helical wave filter 126 of the present invention. By controlling the dielectric type, the dielectric constant can be varied anywhere from two to fifty. Most polymer-type dielectric coatings have a dielectric constant that fall between two and four. However, there are certain other types of dielectrics such as tantalum oxide, which would provide significantly higher dielectric constants (closer to 40). Different materials with different dielectric constants can be used in different sections of the multilayer helical wave filter.

In FIG. 8, one can see that the return wire or segment 144 is directed through the inside of both the first helically wound inductor segment 142 and the second helically wound inductor segment 146. FIG. 9 shows an alternate configuration wherein the return wire or segment 144 returns outside of both the first helically wound inductor segment 142 and the second helically wound inductor segment 146. In both FIG. 8 and FIG. 9, this return wire or connecting segment 144 is a straight elongated conductor. As will be shown in subsequent drawings, it will also be possible to coil this conductor 144 to increase mechanical flexibility of the filtered region. It is advised that the number of coils in this return path be limited to the minimum number of turns needed. This is to ensure that the eddy currents created by this return path (reverse currents) will be minimal and should not greatly impact the overall inductance of the first and second helical wound segments. Typically, the coiled return path is disposed at an angle to the first and second helically wound segments. This is to reduce the effect of eddy currents due to reverse currents in the return path [ideally close to 90 degrees is better but it could be anywhere greater than 0 degrees except (n*pi) n being 0, 1, 2, etc.]. This coiled return path is also useful in increasing or controlling the phase shift between the RF induced currents in the first helically wound inductor segment 142 relative to the currents in the second helically wound inductor segment 146.

Figure 10:
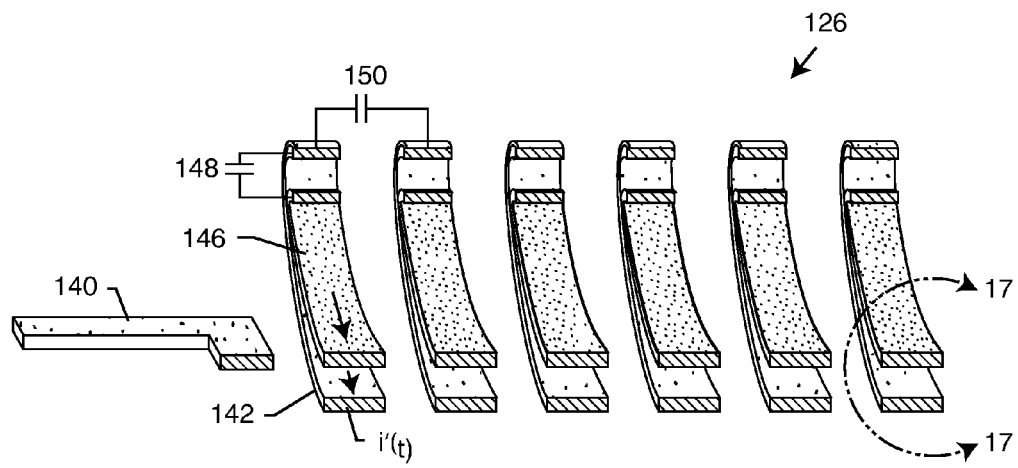
FIG. 10 is a sectional view taken generally along the line 10-10 from FIG. 9.

FIG. 10 is taken along section 10-10 from FIG. 9 and shows the elongated conductor 140 that forms the first helically wound inductor segment 142 and the second helically wound inductor segment 146 in cross-section. A capacitance 148 is formed between each of the coplanar surfaces between the first helically wound inductor 142 and the second helically wound inductor 146. In addition, there is a parasitic capacitance 150 that is formed between adjacent turns of both the first helically wound inductor 142 and the second helically wound inductor segments 146. The first helically wound inductor 142 and the second helically wound inductor 146 along with capacitance 148 and 150 form a multilayer helical wave filter in accordance with the present invention. By carefully adjusting the inductance and capacitance values, one can design the filter to resonate and provide a very high impedance at one or more selected MRI RF frequencies.

Figure 11:
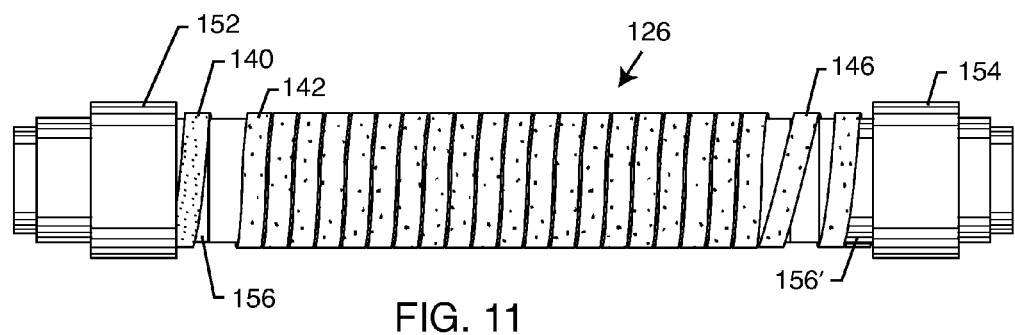
FIG. 11 is an elevational view of the multilayer helical wave filter of FIGS. 8 and 9 with end caps for convenient mechanical and electrical connection into an implantable lead.

FIG. 11 illustrates the multilayer helical wave filter previously illustrated in FIGS. 8 and 9 with end caps 152 and 154 for convenient mechanical and electrical connection in series into one or more conductors of an implantable lead of an AIMD. For example, an implantable lead 114 may be comprised of material MP35N. The lead conductor would be easily laser welded to mandrel end cap 156 of 152. The multilayer helical wave filter of the present invention is disposed between these two end caps. End cap 154 is shown connected to a distal electrode in contact with body tissues. The multilayer helical wave filter 126 of the present invention can be disposed anywhere along the length of an implanted lead. However, in a particularly preferred embodiment, it is disposed at or near the distal electrode. An electrode assembly (not shown) may be electrically and mechanically connected to end cap 154.

Figure 12:
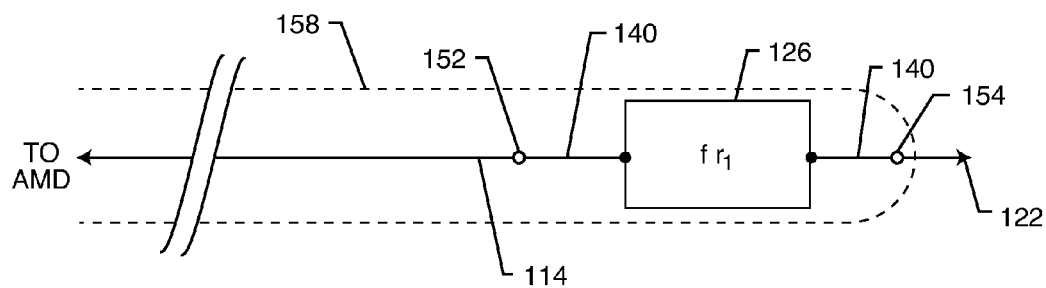
FIG. 12 is an electrical schematic diagram of the multilayer helical wave filter of FIG. 11.

FIG. 12 is a schematic diagram showing the multilayer helical wave filter 126 disposed between the two end caps 152 and 154. The end caps are shown attached in the implantable lead 114 with one end directed to the AMD and the other end directed to electrode 122. Multiple discrete multilayer helical wave filters may be installed in series anywhere along the length of the implanted lead as well. An overall electrical insulation 158 is integral to the lead 114 and also surrounds both end caps 152 and 154 in the entire multilayer helical wave filter 126. This insulation is very important to prevent RF electrical leakage through body fluids in parallel with the multilayer helical wave filter 126. Such RF leakage currents can significantly degrade the impedance of the multilayer helical wave filter at its one or more resonant frequencies. The amount of RF current leakage can be so severe that the multilayer helical wave filter becomes ineffective in preventing a distal electrode from overheating during an MRI scan.

Figure 13:
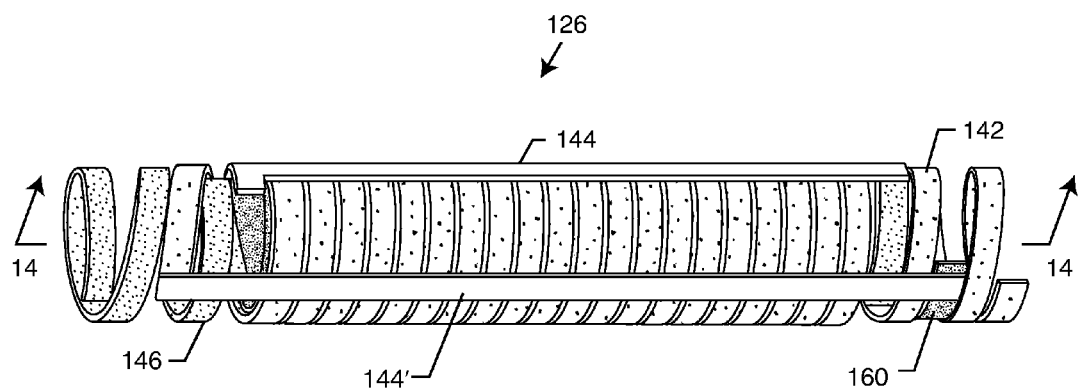
FIG. 13 is shows a structure similar to FIGS. 8-10, except that the multilayer helically wound wave filter includes a third helically wound inductor segment.

FIG. 13 is very similar to FIGS. 8, 9 and 10 except that it additionally has a third helically wound inductor segment 160. In this case, there are two return connecting segments 144 and 144'. All three of the helically wound inductor segments 142, 146 and 160 have facing planar surfaces in which capacitances 148 are formed. In addition, there are parasitic capacitances 150 between the turns of each one of the first, second and third helically wound inductor segments. The structure of FIG. 13 is useful to form multiple resonances to provide a high impedance and therefore a high degree of attenuation to various MRI RF pulsed frequencies. For example, typical 1.5 Tesla scanners operate at an RF pulsed frequency of approximately 64 MHz. 3.0 Tesla scanners are becoming more common and operate at 128 MHz RF pulsed frequency. By having a multilayer helical wave filter 126 that provides a resonance at both these frequencies, the implanted lead system can provide a high degree of immunity to overheating from both the 1.5 and 3-Tesla systems. Accordingly, the multilayer helical wave filter can be designed to be resonant at a first, second or even "n" selected RF frequencies.

Figure 14:
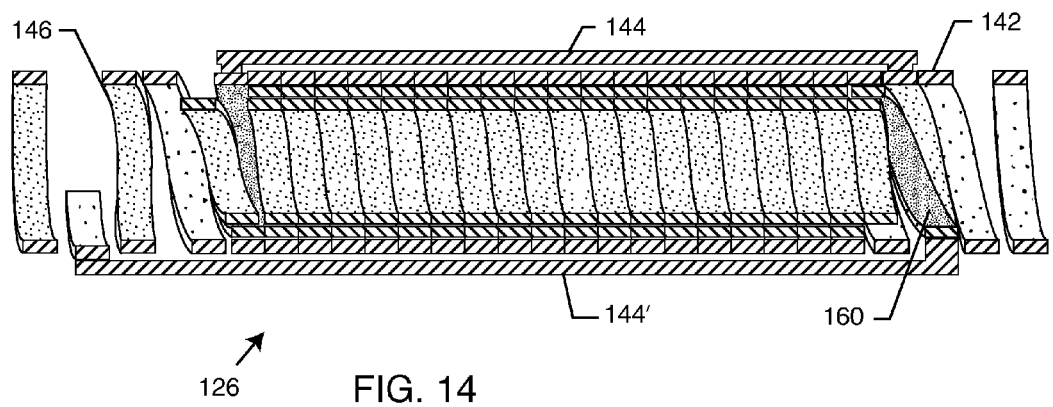
FIG. 14 is a sectional view taken generally along the line 14-14 from FIG. 13.

FIG. 14 is a sectional view taken from section 14-14 from FIG. 13. The three helically wound inductor segments 142, 146 and 160 are clearly shown. One could use the same dielectric material to coat all three helically wound segments or use different dielectric materials. For example, one could use one dielectric material between the first and second inductor segments and a second dielectric material between the second and third helically wound segments. This would create a different parasitic capacitance and thereby a different resonant frequency. The result is a multilayer helical wave filter 126 which could be designed to be resonant at a number of selected MRI RF pulsed frequencies. In general, the resonant frequency of each segment is approximated by the equation:

$$f_r = \frac{1}{2\pi\sqrt{LC}}$$

Where $f_r$ is the resonant frequency, L is the inductance, in Henries, of the inductor component, and C is the capacitance, in Farads, of the capacitor component. In this equation, there are three variables: $f_r$, L, and C. The resonant frequency, $f_r$, is a function of the MRI system of interest. As previously discussed, a 1.5 T MRI system utilizes an RF system operating at approximately 64 MHz, a 3.0 T system utilizes a 128 MHz RF, and so on. By determining the MRI system of interest, only L and C remain. By first selecting one of these two variable parameters, a filter designer needs only to solve for the remaining variable. Note, for a more accurate prediction of resonant frequency $f_r$, the PSPICE circuit of FIG. 23 should be used.

Figure 15:
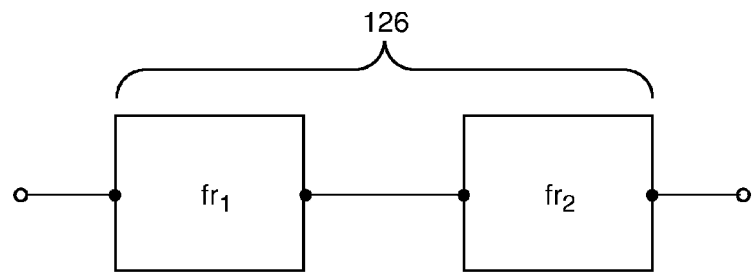
FIG. 15 is an electrical schematic diagram of the multilayer helical wave filter of FIGS. 13 and 14.

FIG. 15 is the schematic diagram of the multilayer helical wave filter of FIGS. 13 and 14 illustrating that the wave filter has multiple resonances at $f_{r1}$ and $f_{r2}$. For example, the multilayer helical wave filter 126 can be designed to be resonant at both 64 MHz (1.5-Tesla MRI) and 128 MHz (3-Tesla MRI). Accordingly, this would provide a very high impedance in the implanted lead during patient exposure to either one of these commonly available MRI scanners.

Figure 16:
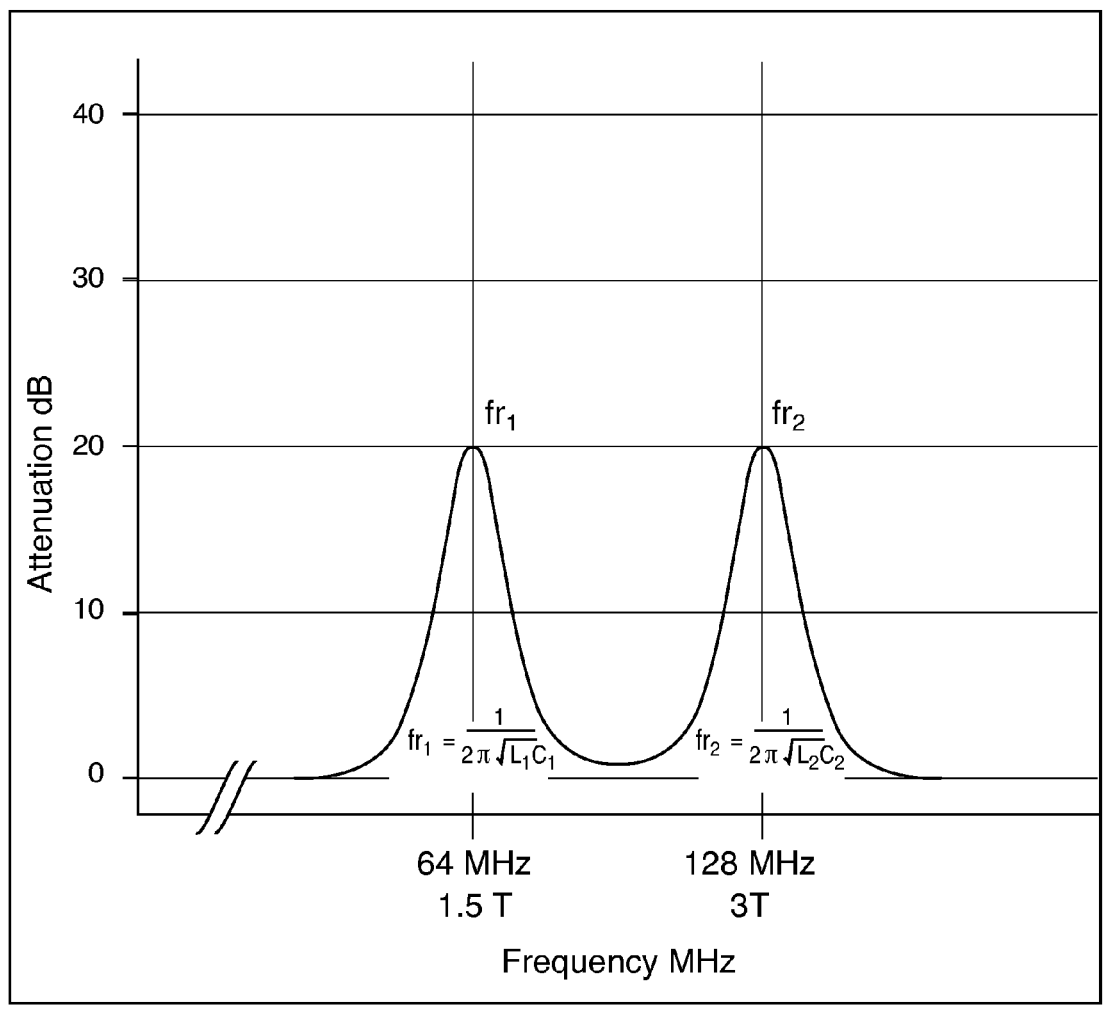
FIG. 16 is a graph of attenuation of the multilayer helical wave filter of FIGS. 13 and 14 versus frequency.

FIG. 16 is a graph of attenuation of the multilayer helical wave filter 126 of FIGS. 13 and 14 versus frequency in MHz. As one can see, there is a resonant peak at both $fr_1$ and $fr_2$ corresponding to 64 MHz and 128 MHz. In both cases, the impedance of the multilayer helical wave filter 126 is quite high which results in an attenuation value exceeding 10-dB. In general, the attenuation would be measured on a Spectrum Analyzer in a balanced 50-ohm system.

Figure 17:
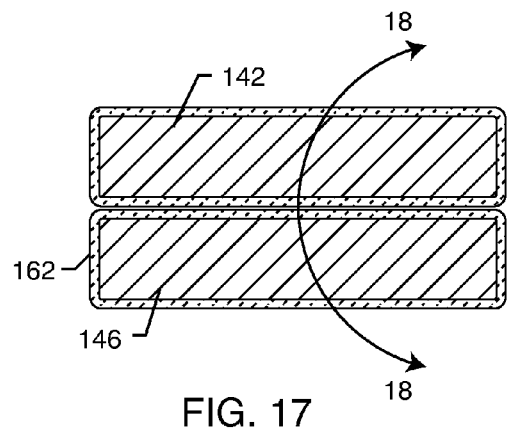
FIG. 17 is an enlarged sectional view taken of the area indicated by line 17-17 from FIG. 10.

FIG. 17 is taken generally along section 17-17 from FIG. 10. Shown is the end view of the elongated conductor that forms the first helically wound inductor segment 142 and the second helically wound inductor segment 146. One can see that in the preferred embodiment, the outer or first helically wound inductor segment 142 is wound very tightly to the second helically wound inductor segment 146. Preferably, there is little to no air gap in between. In addition, there is a dielectric or insulative coating 162 on the elongated conductor(s). This dielectric coating 162 is very important for two reasons: (1) it prevents adjacent turns from shorting and also prevents the first helically wound inductor segment 142 from shorting to the second helically wound inductor segment 146; and (2) the dielectric coating material has a much higher dielectric constant than air, thereby allowing one to increase or tune the capacitances 148 and 150.

Figure 18:
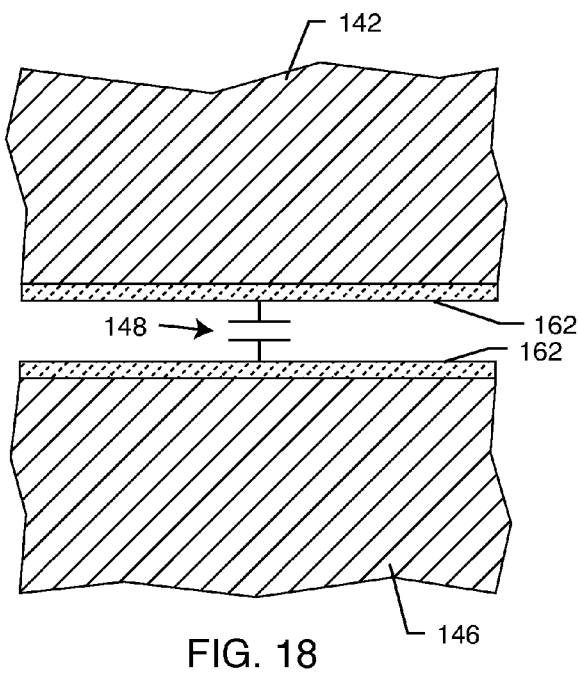
FIG. 18 is a sectional view taken generally along line 18-18 from FIG. 17, illustrating capacitance between adjacent helically wound segments.

FIG. 18 is taken generally along section 18-18 from FIG. 17. The capacitance 148 is shown. As previously described, the first helically wound inductor 142 would be wound tightly to the second helically wound inductor 146. However, in FIG. 18, they are shown separated for convenience so one can show the schematic symbol for the capacitor 148. The amount of parasitic capacitance 148 is determined by the overlap area of the outer helix segment and the inner helix segment. One can increase the amount of capacitance by increasing the width of the elongated conductors 142 and 146. The capacitance value is also related to the dielectric constant of the insulating material 162 and also the dielectric thickness of the insulting material 162. Reducing the dielectric thickness increases the capacitance value significantly. These relationships are expressed ideally by the following equation:

$$C = \frac{n\kappa A}{t},$$

where n is the number of overlapping capacitance areas, k is the dielectric constant of the insulating material, A is the effective capacitance area and t is the thickness between opposing plates. For the overlapping faces of the inner and outer segments of a multilayer helical wave filter, the effective capacitance area is relatively large since it includes the entire overlap area. This gives the designer many degrees of freedom in selecting the primary parasitic capacitance value 148.

Figure 19:
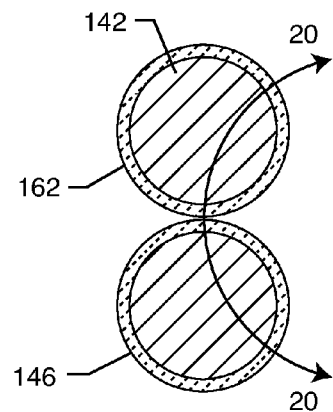
FIG. 19 is a view similar to FIG. 17, wherein the adjacent helically wound segments are round rather than rectangular.
Figure 20:
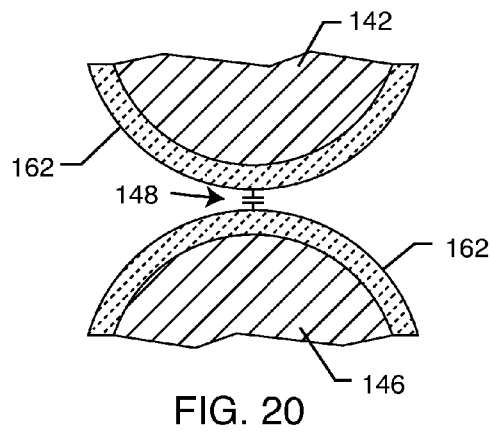
FIG. 20 is a sectional view taken generally along line 20-20 and similar to FIG. 18, illustrating capacitance between adjacent wires.

FIG. 19 is substantially the same as FIG. 17, except that the conductor is no longer rectangular or square in cross-section. The conductor shown in FIG. 19 would be a conventional round wire which would be highly undesirable in the present invention. As shown in FIG. 20, the effective capacitance (ECA) overlap area would be very small. Not only would the resulting capacitance be very small, but it would also be highly variable. As one can see, any slight variations in winding or winding alignment would cause the capacitance value of 148 to vary dramatically. Accordingly, it is a feature of the present invention that the elongated conductor 140 that forms the multilayer helical wave filter 126 be of either rectangular or square wire, preferably coated in a dielectric film 154 or the like. The size and shape of the elongated conductor that forms the helically wound segments is important. In general, a square or rectangular cross-section is preferred. By controlling the geometry and/or width of the elongated conductor that overlaps between the adjacent first helical segment and the second helical segment, one can control the parasitic capacitance that is formed. In other words, the designer can control the resonant frequency by controlling both the inductance and the amount of parasitic capacitance that is formed. Importantly, the designer can also control the Q and resulting 3-dB bandwidth at resonance of the multilayer helical wave filter. The primary factor in controlling the Q is to control the resistance of the wire that forms the first helical segment and the second helical segment. The resistivity of the wire is one of its primary material properties. One can choose from various materials to form the elongated conductor and the first and second helical segments. The resistance is also determined by the overall length of the elongated conductor of the first and second helical segments and also inversely related to its cross-sectional area (width times height). One also controls the parasitic capacitance by proper selection of the type of dielectric coating, the dielectric thickness and/or the distance between the inner and outer segments. This can be used to control second, third of even n resonant frequencies as well. A primary determining factor of the parasitic capacitance is the effective capacitance area which is determined by the amount of planar surface overlap between the first helically wound segment and the second helically wound segment. The first, second and third inductor segments can all be of the same cross-sectional shape and area elongated conductors and of the same number of turns. However, each segment could also have a different cross-sectional area of conductor and even a different number of turns. This affords the designer many degrees of freedom in controlling the inductance, resonant frequency and the Q of each resonant section.

There are several ways to apply the dielectric coating 154. One way would be to coat the entire elongated conductor wire 140 before forming the first and second helically wound inductor segments 142 and 146. Another way to do this would be through carefully controlled winding processes where the entire assembly was subsequently dipped or subjected to vacuum deposited dielectric material such as parylene. In another embodiment, a dielectric film could be disposed between the first helically wound inductor segment 142 and the second helically wound inductor segment 146. There are various suitable dielectric insulative materials such as Polyimide, aromatic polyimide, liquid crystal polymer, PTFE, PEEK, ETFE, Parylene, tantalum oxides, any nano-dielectric coating, PFA, FEP, Polyurethane, polyurethane with self-bonding overcoat, polyamide, polyvinyl acetal, polyvinyl acetal overcoated with polyamide, polyurethane overcoated with polyamide, epoxy, polyester (amide) (imide) overcoated with polyamide, polyester (amide) (imide), silicone-treated glass fiber, polyamide-imide, thermoplastic compounds, polyvinylchloride (PVC), polyolefin class: {LDPE, HDPE, TPO, TPR, polyolefin alloys}, LDPE low density, HDPE high density, polypropylene (PP), thermoplastic fluoropolymers, TEFLON FEP, Tefzel ETFE, Kynar PVDF, TEFLON PFA, Halar ECTFE, PTFE Teflon, PTFE Teflon film, XLPE & XLPVC, silicone rubber, Polyimide Kapton film, Polyester Mylar film, Kaladex PEN film, crosslinked polyalkene, and various other types of polymer or ceramic materials. Different dielectric materials may be used for different sections of the multilayer helical wave filter. This would be to create different capacitance values and different resonance sections.

Figure 21:
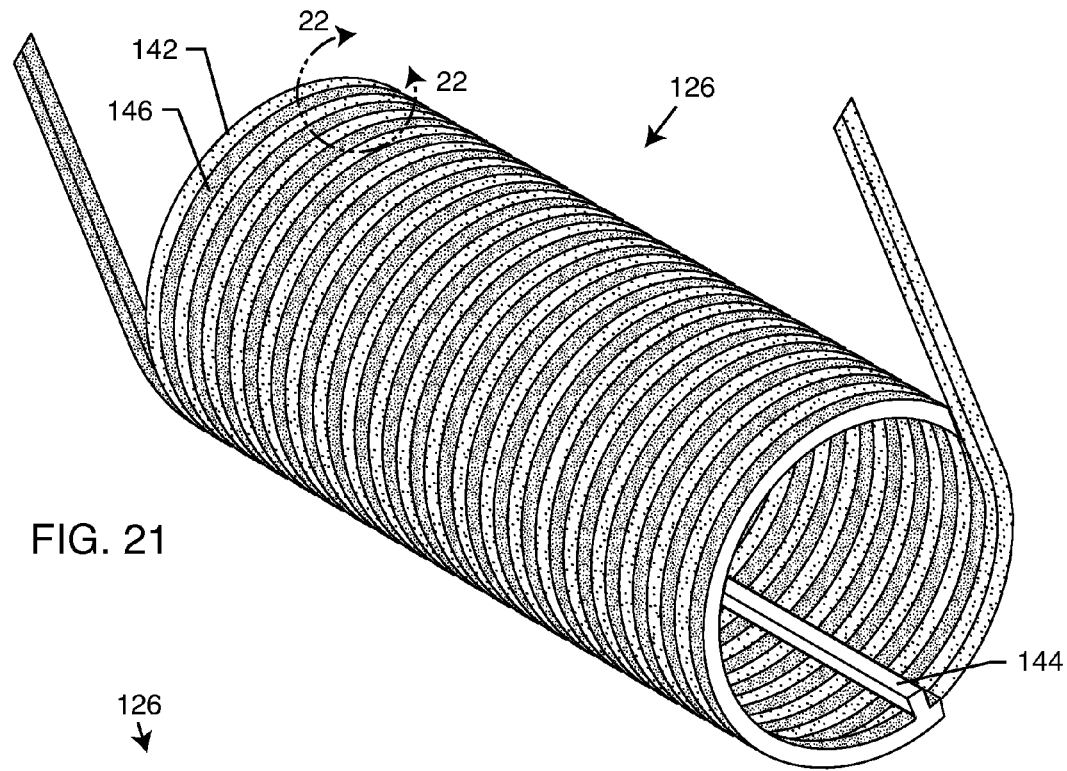
FIG. 21 is similar to FIG. 8, but illustrates an alternative embodiment wherein adjacent inductive segments are aligned side-by-side.

FIG. 21 illustrates an alternative construction of the multilayer helical wave filter 126 of the present invention. Referring back to FIGS. 8 and 9, one can see that the second helically wound inductor segment 146 is wound inside of the first helically wound inductor segment 142 on the same longitudinal axis. In FIG. 21, by way of contrast, one can see that the first helically wound inductor segment 142 and the second helically wound inductor segment 146 are wound adjacent to each other side-by-side along the same longitudinal axis. There is still a return wire 144 in order to make sure that the direction of turns of both the first helically wound inductor 142 and the second helically wound inductor 146 are in the same direction so that the RF currents are in the same direction as described in connection with FIGS. 8 and 9.

Figure 22:
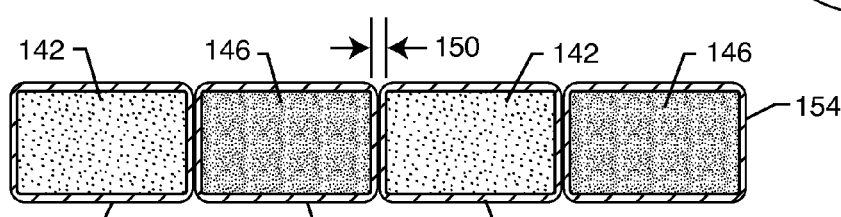
FIG. 22 is an enlarged sectional view taken generally along line 22-22 from FIG. 21.

FIG. 22 is taken generally along section 22-22 from FIG. 21. This shows the elongated conductor 140 of the first helically wound inductor segment 142 alongside the elongated conductor forming the second helically wound inductor segment 146. As can be seen, there is a capacitance 150 that is formed between the coils of the first helically wound inductor 142 and the second helically wound inductor 146 segments.

Figure 23:
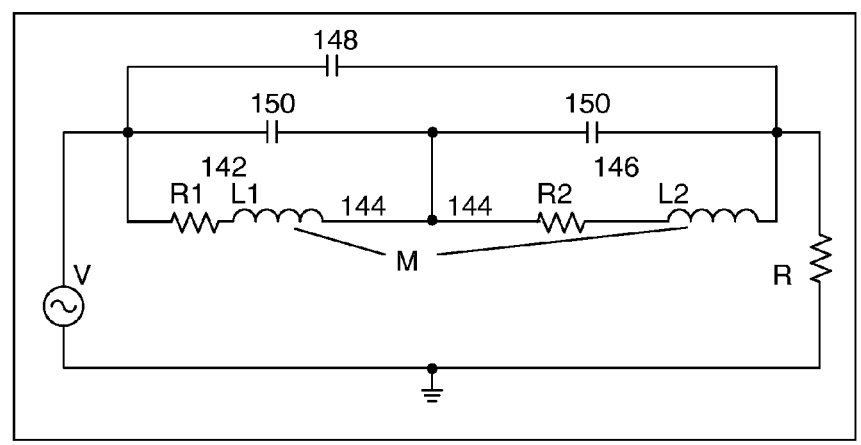
FIG. 23 is a simplified P-Spice electrical schematic diagram of the multilayer helical wave filter shown in FIGS. 8-10.

FIG. 23 is a simplified P-Spice schematic diagram of the multilayer helical wave filter 126 shown in FIGS. 8, 9 and 10. The voltage source shown in FIG. 18 would be the voltage induced in an implanted lead by a medical diagnostic procedure, such as by the RF field of an MRI scanner. The load resistance R is shown for simplification and would actually be a complex impedance based on the impedance of the lead system, body tissues and the input impedance of the active medical device (AMD). Those skilled in the art will understand that the capacitances and inductances and resistances of FIG. 23 would be distributed throughout the length of the multilayer helical wave filter 126. They are shown as lumped elements for simplicity. In FIG. 23, one can see the first helically wound inductor segment 142 consisting of L1 and resistance R1. The second helically wound inductor segment 146 is shown as inductance L2 and resistance R2. The resistance values R1 and R2 are determined by the classical resistance of any conductor wherein the resistance is proportional to the conductivity Rho (times) the length L (divided by) cross-sectional area A. The 3 dB bandwidth of the resonance of the multilayer helical wave filter 126 is determined by its Q at resonance. The Q is defined as the frequency of resonance (divided by) the change in (delta) 3 dB bandwidth $Q=f_r/\Delta f_{3\ dB}$. For a more complete description on this subject, one is referred to U.S. Pat. No. 7,363,090 and US 2011/0144734. As previously described, by controlling the inductance and capacitance of different sections, the multilayer helical wave filter 126 can be designed to have multiple resonances at different frequencies. Interestingly, one could also vary either the conductor 140 cross sectional area, material or length in different sections which would result in a different Q and 3-dB bandwidth at each resonant frequency. As one can see, the novel multilayer helical wave filter 126 affords the designer many opportunities to attenuate the current flow of one or multiple RF frequencies.

Figure 24:
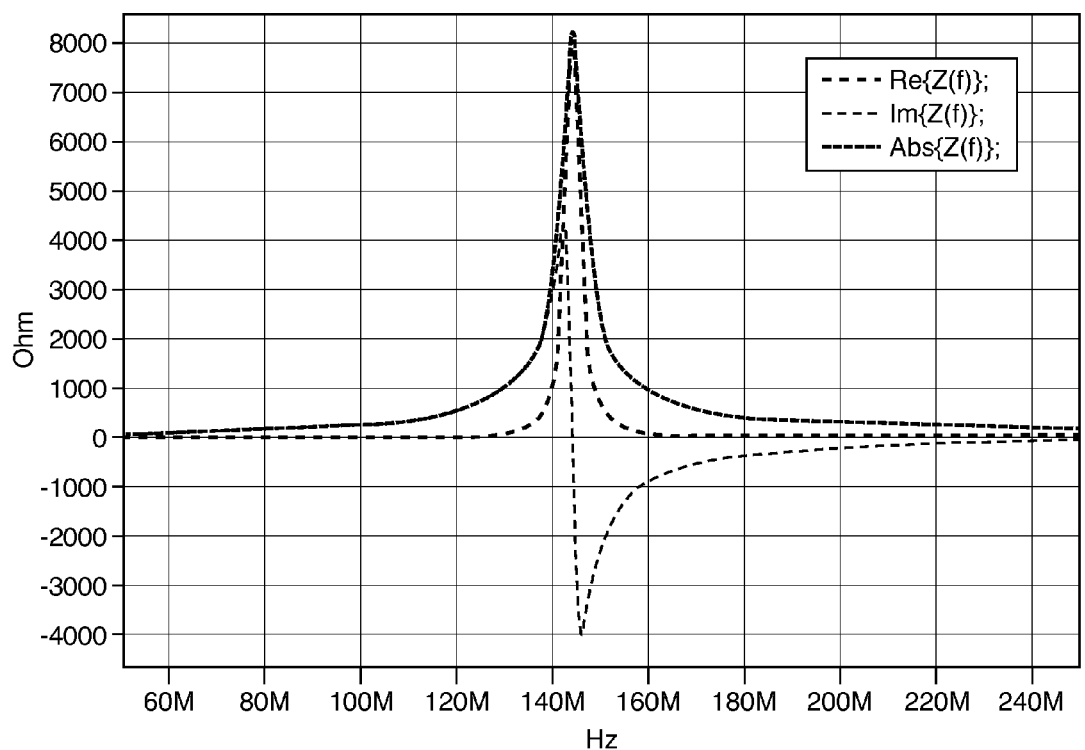
FIG. 24 is a graph illustrating the frequency response of a 20-turn coaxial two-layer helical bandstop filter of the present invention.

FIG. 24 is the frequency response of a 20 turn coaxial 2-layer helical wave filter 126 showing a resonant peak at 144 MHz. The cross-sectional area of the elongated conductor that forms the multilayer helical wave filter segments can vary in width anywhere from 0.0005 inches to 0.025 inches. The height of the rectangular square wire can also vary anywhere from 0.0005 inches to 0.025 inches. If the elongated conductor is round, the diameter can vary anywhere from 0.0010 to 0.025. The multilayer helical wave filter can be particularly designed for cardiac leads, wherein the diameter is typically anywhere from 2 French to 9 French (0.090 inches for 7 French or for neuro leads of 0.052 inches in diameter, which are typically 1 French. In general, the multilayer helical wave filter of the present invention can be built in any size from 1 French and above. Shown are the real part, the imaginary part and the absolute values of the impedance. One can also control the resistance R1 and R2 of the multilayer helical wave filter by proper conductor material selection. Biocompatible materials include MP35N, stainless steel and all of its alloys, tantalum, or drawn filled tubes. Drawn filled tubes can have a core of silver, gold, platinum or the like with an outer coating or tubing of MP35N, stainless steel 316LVN, nitinol or the like. Accordingly, one can control the inductance, the capacitance and the resistance of each segment of the multilayer helical wave filter individually. The resistance will largely determine the Q and the 3-dB bandwidth at each resonance point.

Figure 25:
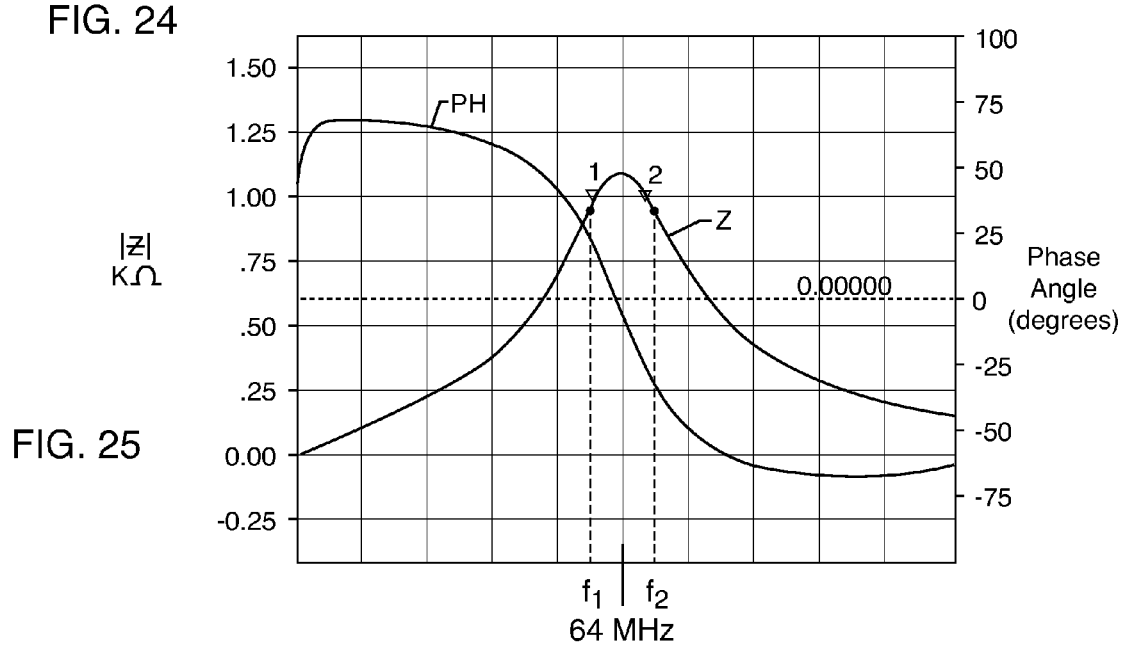
FIG. 25 is a graph showing the frequency response for the multilayer helical wave filter of FIGS. 8-10, which has been modified to show resonance through a frequency range corresponding to the RF pulsed frequency for a 1.5 Tesla MRI scanner.

FIG. 25 shows the helical wave filter 126 of FIG. 8 and FIG. 9 has been modified to show the inductance and the capacitance values 148 and 150 such that the multilayer helical wave filter is resonant at 64 MHz, which corresponds to the RF pulsed frequency for 1.5 Tesla MRI scanners. As can be seen on the left vertical axis, the impedance Z is plotted in kilohms. On the right vertical axis, the phase angle is plotted in degrees. One can see that there is a phase shift from positive to negative that corresponds with the resonant center frequency of 64 MHz. Markers 1 and 2 shown on the impedance curve correspond with frequencies $f_1$ and $f_2$. These are the 3-dB down points. The 3-dB bandwidth is preferably 10 kHz or greater and is the difference in frequency of $f_2-f_1$. The 3-dB bandwidth would be best measured in a Spectrum or Network analyzer in a balanced 50 ohm system measuring attenuation. One can see that the multilayer helical wave filter 126 of the present invention provides over 1000 ohms (1 kilohm) of impedance at the MRI RF pulsed frequency. This provides a dramatic amount of attenuation and current reduction thereby preventing implanted leads and/or their associated electrodes from overheating during an MR scan. Optimal selection of materials and dielectrics can provide up to 5 to 10 kilohms of impedance at resonance. As previously mentioned, in order to provide this high impedance at resonance, it is critical that the multilayer helically bandstop filter be insulated such that RF currents cannot conduct around it through body fluids or tissues thereby degrading the impedance through these parallel paths.

Figure 26:
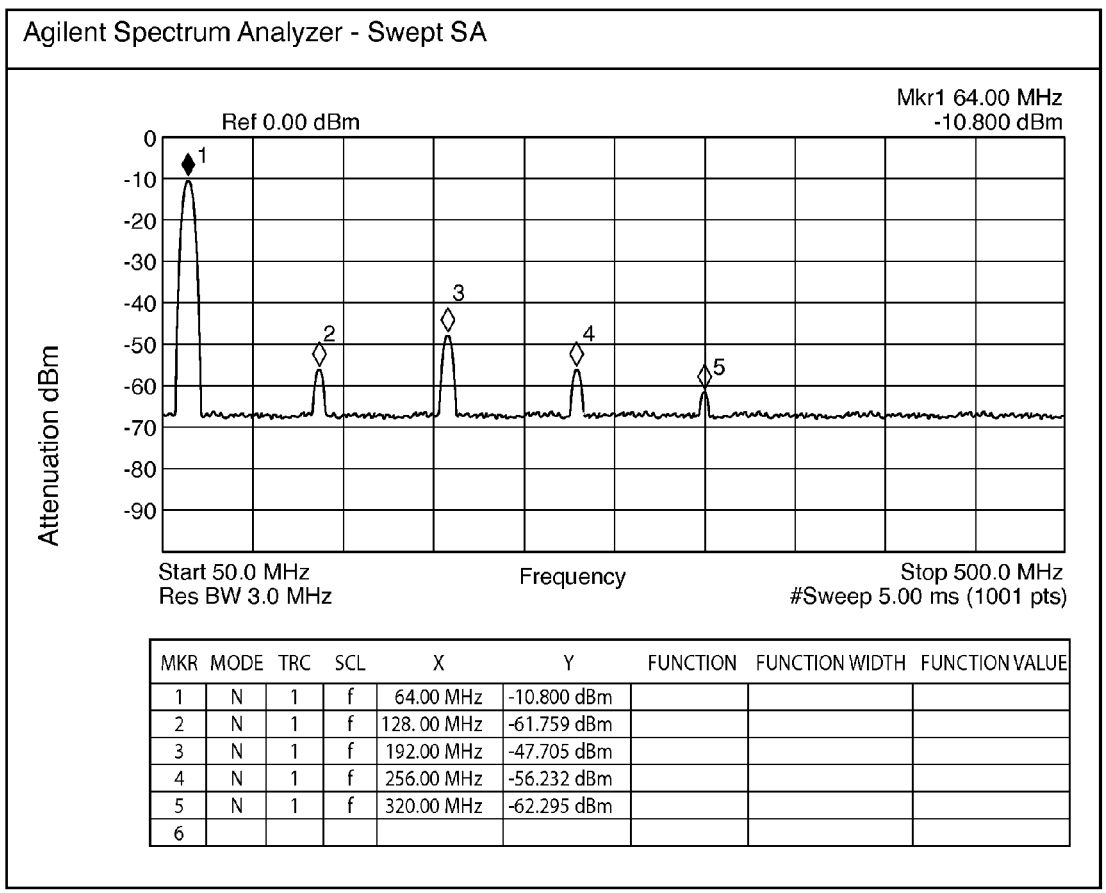
FIG. 26 is a Spectrum Analyzer scan taken from an RF probe located inside a 1.5 Tesla clinical MRI scanner.

FIG. 26 is a Spectrum Analyzer scan taken from an RF probe located inside a 1.5 Tesla clinical MRI scanner. The primary RF pulsed frequency is shown as marker 1 as 64 MHz. The harmonics of the RF pulsed frequency are generally not specified or controlled by manufacturer specifications or industry standards. In other words, these harmonics are largely uncontrolled. The scan shows a harmonic (marker 2) at 128 MHz, a harmonic (marker 3) at 192 MHz, a harmonic (marker 4) at 256 MHz and even a harmonic at 320 MHz (marker 5). The primary RF pulsed frequency (64 MHz) and its harmonics can all contribute to RF currents in a lead and particularly RF currents at a distal electrode to tissue interface. Accordingly, the primary frequency and its harmonics can all contribute to leadwire heating.

The multilayer helical wave filter can be designed to have resonances at the primary MRI RF frequency (64 MHz) and also at some or all of its harmonic frequencies. In general, only harmonics of significant amplitude would require attenuation by the multilayer helical wave filter.

Figure 27:
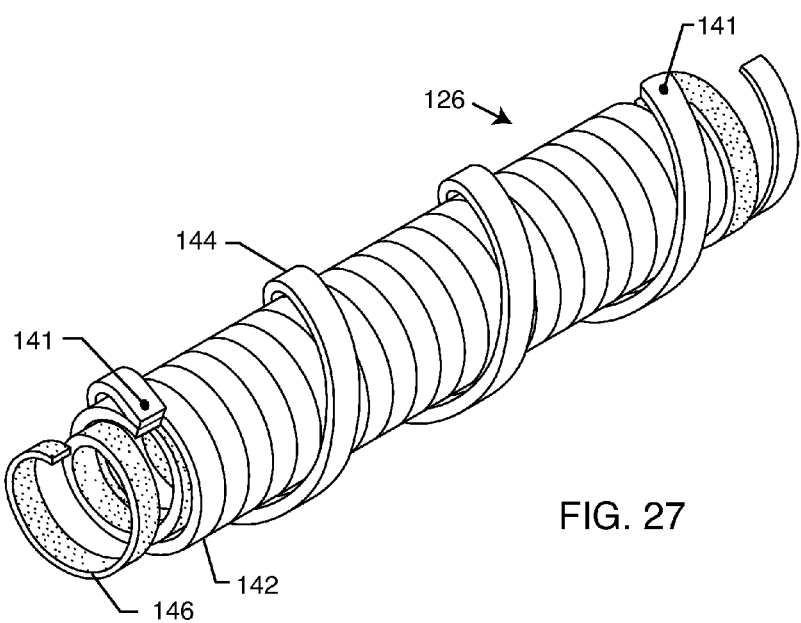
FIG. 27 is an isometric view similar to FIG. 8, except that the connecting segment has been curled around the outside of both the first and second helically wound inductor segments.

FIG. 27 is similar to FIG. 8 except that the connecting segment 144 has been coiled around the outside of both the first helically wound inductor 142 and second helically wound inductor 146 segments. Coiling of the return wire 144 decreases its inductance and increases its capacitance. By changing the inductance of the return wire 144, one controls the phase shift between the RF currents in various segments as previously described. This can be used to introduce a secondary resonance into the multilayer helical wave filter 126 in such a way to provide attenuation at multiple MRI RF pulsed frequencies. For example, attenuation could be provided at both 64 MHz (1.5 Tesla) and 128 MHz (3 Tesla). It will be obvious to one skilled in the art that the multilayer helical wave filter can be designed to have one, two, three or . . . n-resonant frequencies.

Electrical connections 141 are illustrated to show how one interconnects the return layer to various other layers of the present invention. The electrical connection 141, of course, has to be both nontoxic and biocompatible. Suitable electrical connections can be laser welds, gold brazes, other types of brazes, biocompatible thermal-setting conductive adhesives, biocompatible gold-based solders or the like. Importantly, the electrical and mechanical connections 141 could also be done by crimping or other mechanical attachment means.

Figure 28:
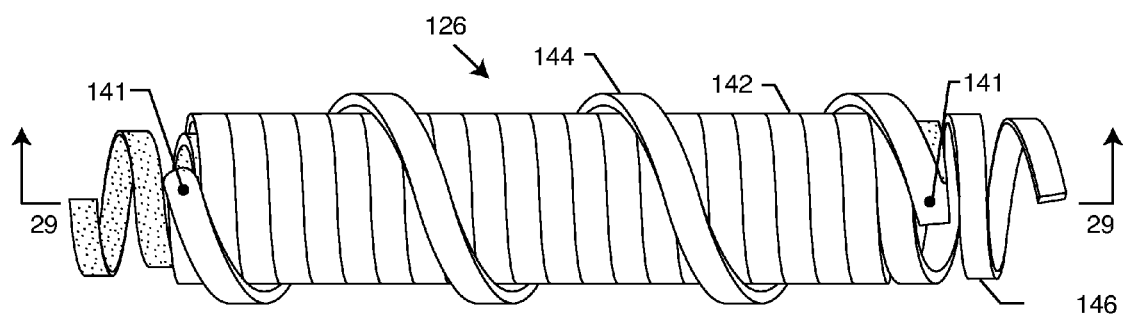
FIG. 28 is side view of the structure shown in FIG. 27.

FIG. 28 is the side view of the multilayer helical wave filter 126 shown in FIG. 27.

Figure 29:
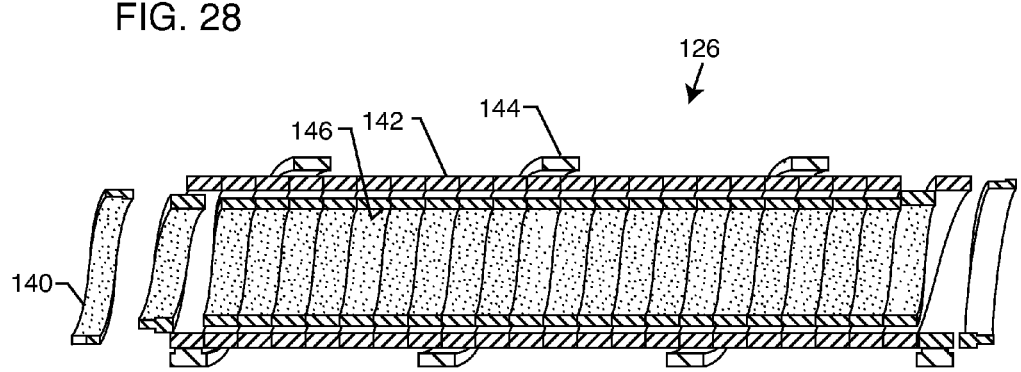
FIG. 29 is a sectional view taken generally along line 29-29 from FIG. 28.

FIG. 29 is a sectional view taken generally along line 29-29 from FIG. 28. Shown is the elongated conductor 140 of the first helical wound segment 142, the second helically wound segment 146 and the connecting segment 144. A coiled return wire 144 could be applied to any of the previously described multilayer helical wave filters 126 such as shown in FIG. 8, 9, 13 or 21.

Figure 30:
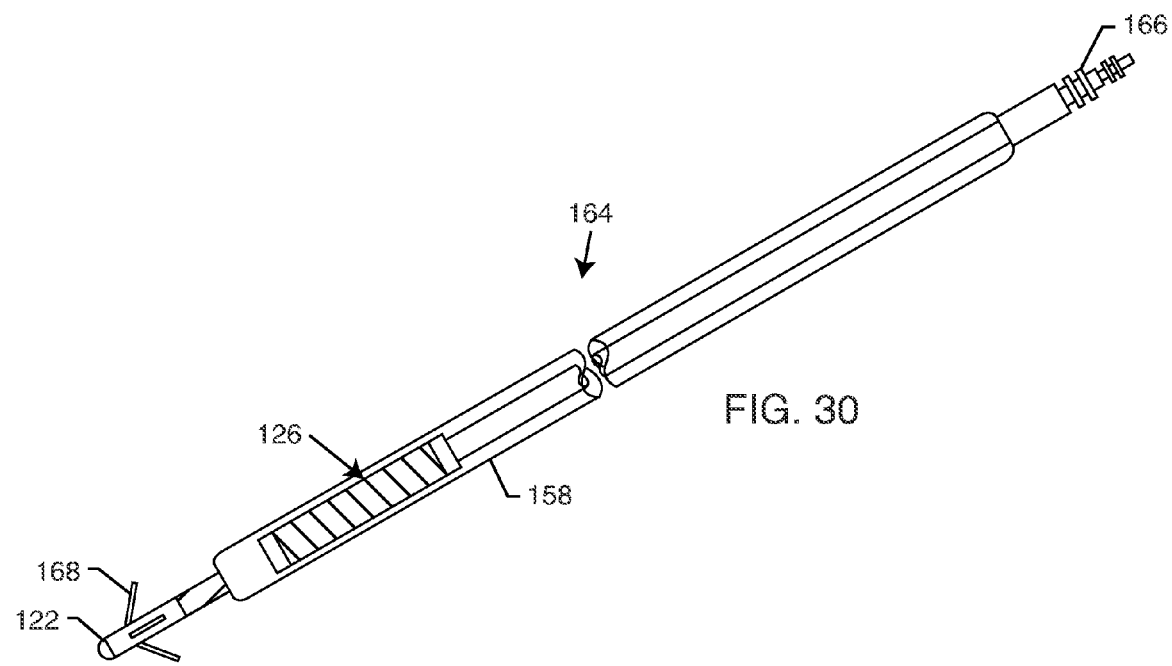
FIG. 30 is an elevational view of a unipolar pacemaker lead having a proximal connector with an embedded multilayer helical wave filter in accordance with the present invention.

FIG. 30 illustrates a unipolar pacemaker lead 164 having a proximal connector 166 such as described by International Standards ISO—IS1, DF1, DF4 or IS4. This proximal connector 166 would be plugged into a cardiac pacemaker, a cardioverter defibrillator or the like (not shown). The distal end of the lead has a tip electrode 122 with tines 168 which are used to grasp trabecular or other tissue within a human heart. Shown is a multilayer helical wave filter 126 of the present invention that is located near or at the distal unipolar electrode 122. Referring once again to FIG. 30, one can see that the lead body has an overall insulation 158 which extends over the multilayer helical wave filter to a point near the distal electrode 122. This insulation is critically important to prevent RF currents from circulating through the body fluids thereby tending to short out or degrade the impedance of the multilayer helical wave filter 126. In a preferred embodiment, the overall insulation 158 still provides that the center of the multilayer helical wave filter can be hollow for convenient guide wire insertion. In addition, the center of the wave filter could incorporate one or more valves such that additional leads or guide wires placed from the proximal side can be routed and sealed. Access from the distal side would be restricted in a similar manner to a hemostasis valve in an introducer. As previously described, when exposed to an MRI high intensity RF environment, the multilayer helical wave filter 126 impedes the undesirable flow of RF currents into body tissues via electrode 122. Referring once again to FIG. 30, one can see that the lead body has an overall insulation 158 which extends over the multilayer helical wave filter to a point near the distal electrode 122. This insulation is critically important to prevent RF currents from circulating through body fluids thereby tending to short out or degrade the impedance of the multilayer helical wave filter 126. Thereby the multilayer helical wave filter 126 prevents overheating of the distal electrode 122 and/or the surrounding body tissues. It has been shown, that overheating of said tissues can cause changes in pacemaker capture threshold or even complete loss of pacing.

Figure 31:
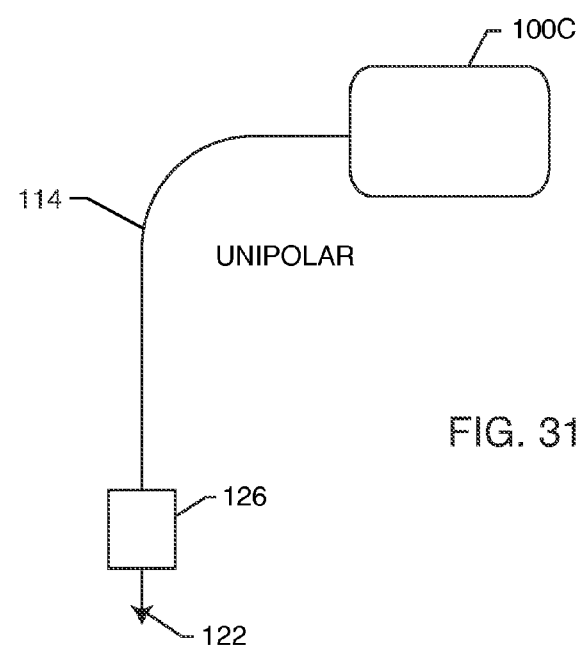
FIG. 31 is a schematic diagram of the unipolar lead of FIG. 30.

FIG. 31 is a schematic diagram of the unipolar lead 164 of FIG. 30 showing the AMD 100C and a multilayer helical wave filter 126 of the present invention installed preferably at or near the distal tip electrode 122.

Figure 32:
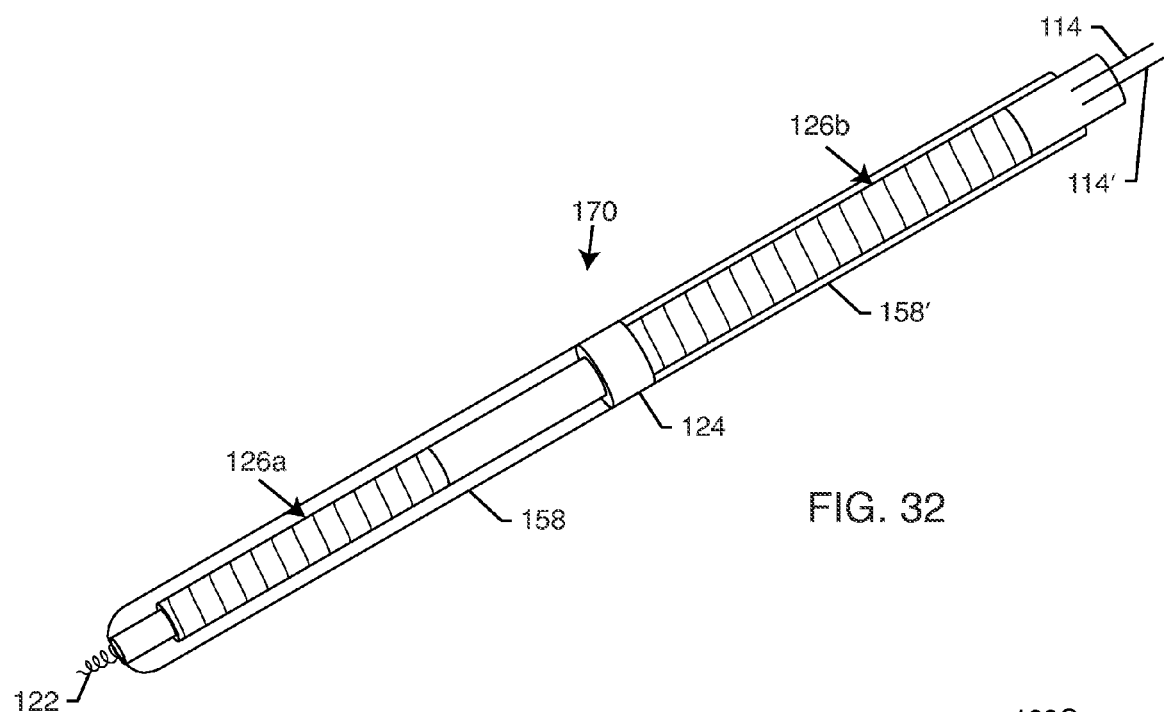
FIG. 32 is a view similar to FIG. 30, except that the multilayer helical wave filter of the present invention is associated with the tip and ring electrodes of an active fixation tip.

FIG. 32 is very similar to FIG. 30 except a bi-polar active fixation electrode 170 is shown at the distal end or tip of the implanted lead. In this case, the screw-in helix tip electrode 122 has been extended, which would typically be screwed into cardiac tissue. A ring electrode 124 forms a bi-polar electrode system wherein pacing and sensing can be conducted between the helix tip electrode 122 and the ring electrode 124. There would be two conductors 114 and 114' in this case that would be routed to and plugged into the active medical device. There is a multilayer helical wave filter 126a in series with the helix electrode 122 and also a multilayer helical electrode 126b in series with the ring electrode 124. In this way, both the distal helix 122 and ring electrodes 124 would both be prevented from overheating in an MRI environment. Insulation 158 prevents RF currents from flowing through body fluids and shorting out multilayer helical wave filter 126a and insulation material 158' insulates multilayer helical wave filter 126b and performs the same function. In addition, the insulating layer 158 also protects the implanted lead, provides flexibility and lubricity and aids in the long-term reliability of the overall lead system.

Figure 33:
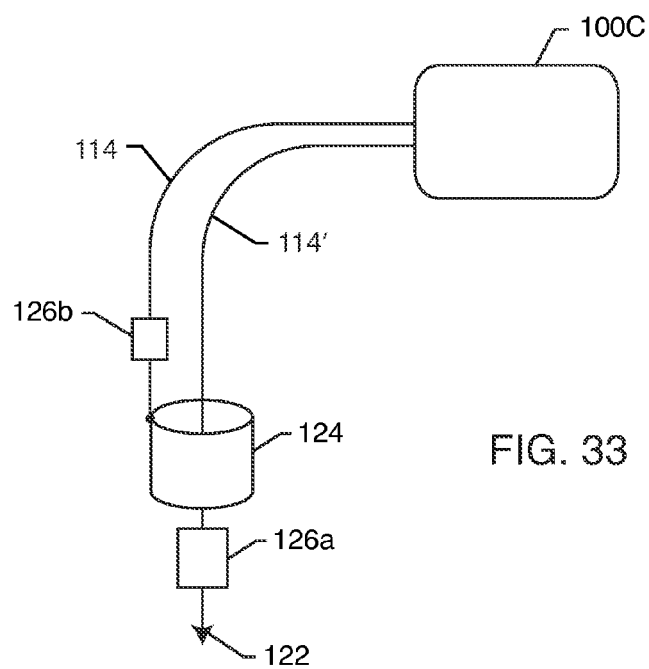
FIG. 33 is an electrical schematic diagram of the bi-polar active fixation electrode illustrated in FIG. 32.

FIG. 33 is the schematic diagram of the bi-polar lead previously illustrated in FIG. 32. One can see the active implantable medical device such as a cardiac pacemaker 100C with implanted lead conductors 114 and 114'. Lead conductor 114 is directed in series with a multilayer helical wave filter of the present invention to ring electrode 124. Lead conductor 114' has multilayer helical wave filter 126a in series with tip electrode 122. As previously described, in preferred embodiments, the multilayer helical wave filter 126a and 126b are very near or at the respective distal electrodes. This prevents RF current induction from MRI fields from coupling around the wave filters and inducing currents in the distal electrodes.

Figure 34:
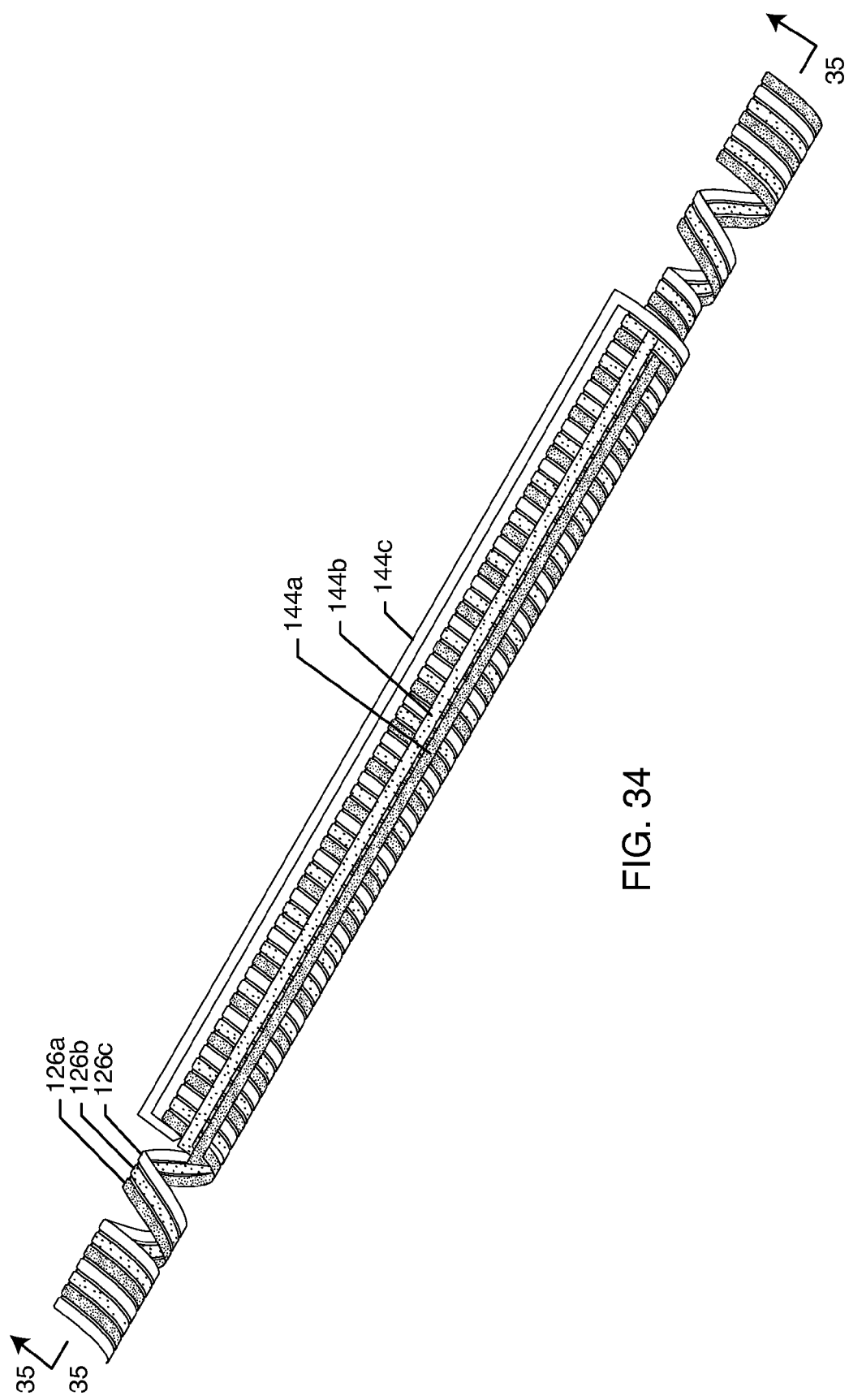
FIG. 34 is an elevational view of the formation of three multilayer helical wave filters wound about a common longitudinal axis.

FIG. 34 illustrates the formation of three multilayer helical wave filters 126a, 126b and 126c of the present invention. As shown in FIG. 36, these could be split out to be placed in series with three different electrodes 122a, 122b and 122c. This arrangement is particularly advantageous for neurostimulator applications where there might be 3, 6, 12, 16, 24 or even "n" electrodes. Accordingly, multilayer helical wave filters 126 can be wound to be in series with any number of such electrodes (n-electrodes). Any number (m) of these "n" multilayer helical wave filters can also be used in a neuro lead wherein the number of electrodes becomes=n×m. In other words, a neuro electrode matrix can be easily formed by the multilayer helical wave filter of the present invention.

FIG. 35 is a sectional view of the three electrode configurations illustrated in FIG. 34. The filter region consists of three multilayer helical wave filters of the present invention.

That, in turn, is connected to the implanted lead. Electrodes 122a, 122b and 122c are typically the ring or pad electrodes of a neural lead.

FIG. 36 is the schematic diagram of the three electrode multilayer helical wave filter of FIG. 35. Shown are three multilayer helical wave filter segments 126a, 126b and 126c shown in series with each of the three ring or paddles electrodes 122a, 122b and 122c. Each of the conductors of the implanted lead 114a, 114b and 114c are shown connected to the active implantable medical device 100C.

Figure 37:
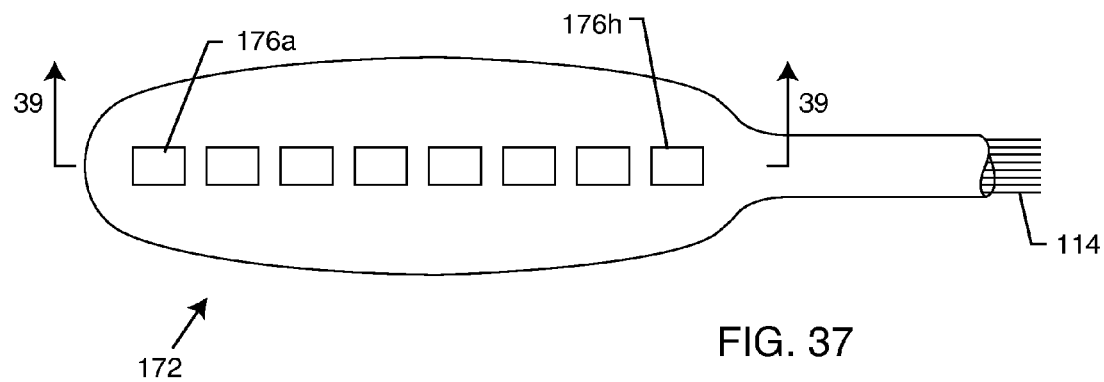
FIG. 37 is an elevational view of an 8-pin paddle electrode.

FIG. 37 illustrates an 8-pin paddle electrode 172 commonly used in spinal cord stimulator applications. The eight paddle electrodes are shown as 176a through 176h.

Figure 38:
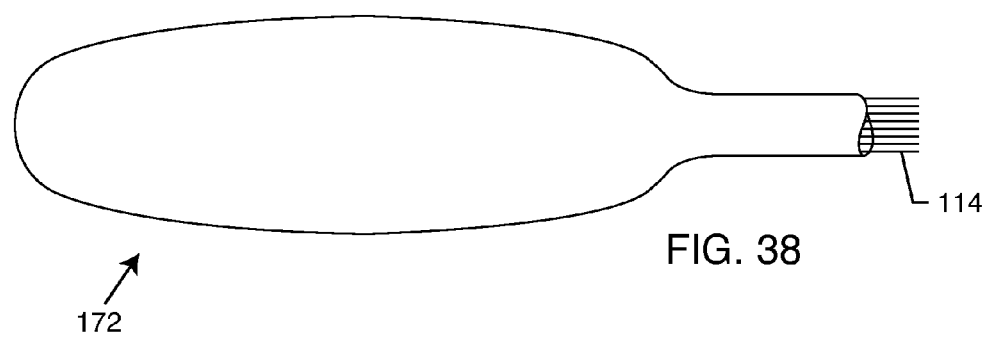
FIG. 38 is an elevational view of the reverse side of the paddle electrode shown in FIG. 37.

FIG. 38 is the reverse side of the paddle electrode 172 of FIG. 37.

Figure 39:
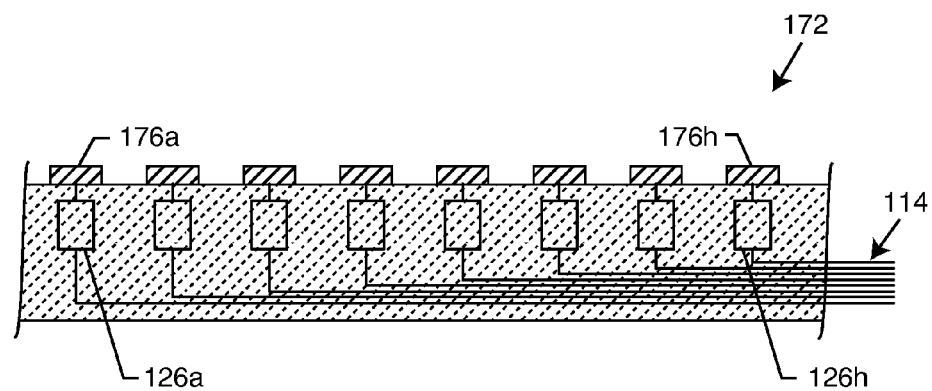
FIG. 39 is an enlarged sectional view taken generally of the area indicated by line 39-39 from FIG. 37.

FIG. 39 is a cross-section taken generally from section 39-39 from FIG. 37. One can see that there is a multilayer helical wave filter 126 in series with each one of the pad electrodes 176. FIG. 39 is just a representative example. As used herein, electrodes shall include any type of electrode in contact with body tissue. This includes, but is not limited to, pacemaker electrodes, endocardial electrodes, epicardial electrodes, defibrillator shocking coils, tip electrodes, ring electrodes, ablation electrodes, deep brain electrodes, nerve cuff electrodes, various types of paddle electrodes, cochlear electrode bundles, Bions, probe and catheter electrodes and the like.

Figure 40:
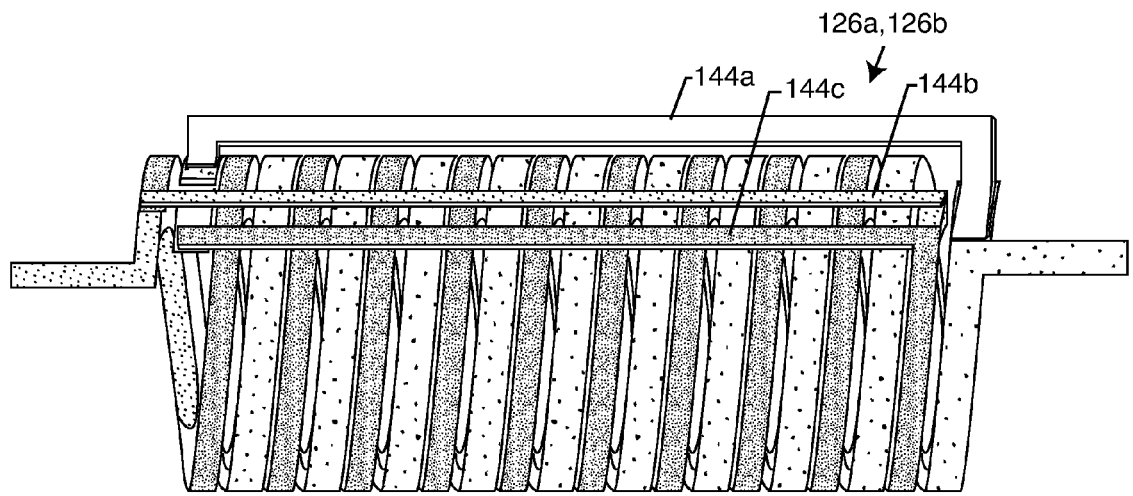
FIG. 40 is an elevational view of another embodiment for a multilayer helical wave filter embodying the present invention, wherein three return conductors are provided to perform two discrete multilayer helical wave filters that are in series with each other.

FIG. 40 is a special multilayer helical wave filter with three return conductors 144a, 144b and 144c which form two discrete multilayer helical wave filters 126a and 126b that are in series with each other. In accordance with the present invention, each one would have a selected RF resonant frequency. In a preferred embodiment, the first resonant frequency $f_{r1}$ would be the RF pulsed frequency of a 1.5-Tesla common MRI scanner at 64 MHz. The second multilayer helical wave filter portion would be resonant $f_{r2}$ at 128 MHz which is the RF pulsed frequency for commonly available 3-Tesla MR scanners. By varying the cross-sectional area of the elongated conductor and also the pitch and number of turns, in addition to the dielectric material and separation between the inner and outer coils, the resonant frequencies $f_{r1}$ and $f_{r2}$ can be precisely tuned.

Figure 41:
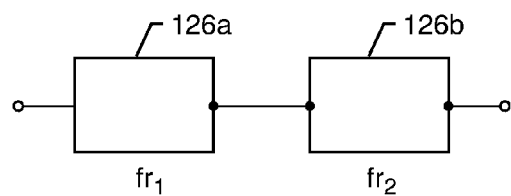
FIG. 41 is a schematic diagram of the multilayer helical wave filter of FIG. 40.

FIG. 41 is a schematic diagram of the multilayer helical wave filter of FIG. 40 showing that it provides (in one package) for two resonances in series which are shown as $f_{r1}$ and $f_{r2}$.

Figure 42:
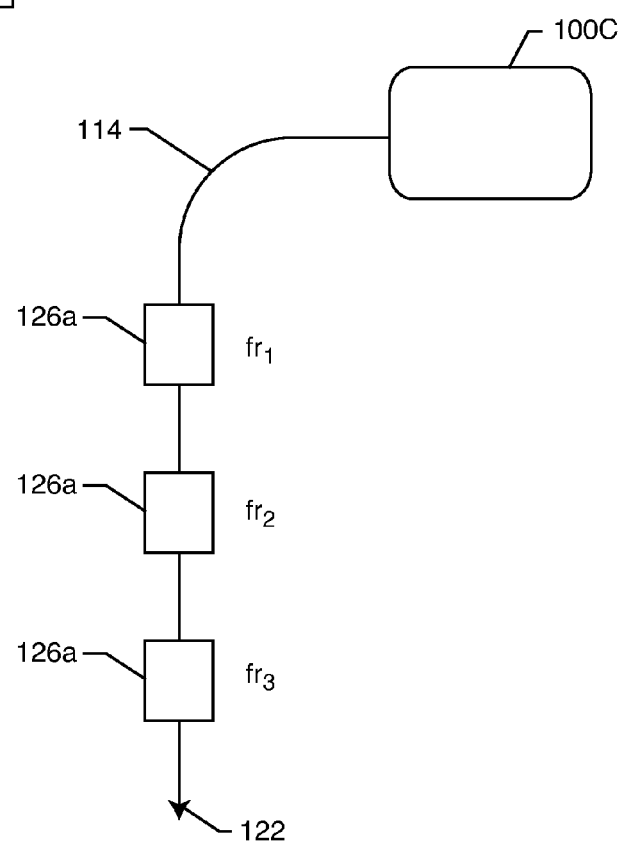
FIG. 42 is a schematic illustration showing that any number of individual multilayer helical wave filters can be placed in series in any conductor of any implanted lead.

FIG. 42 illustrates that any number of individual or separate discrete multilayer helical wave filters 126 can be placed in series in any conductor of any implanted lead in multiple locations along the lead length. For example, referring once again to FIG. 8, three different helical wave filters could be placed in series along the length of an implanted lead as shown. In FIG. 42, there are three different helical wave filters that are resonant at $f_{r1}$, $f_{r2}$ and $f_{r3}$. It will be obvious to those skilled in the art that any number of helical wave filters can be placed in series in an implanted lead. In summary, multiple resonances $fr_1$ and $fr_2$ . . . or $fr_n$ can be created by multiple segments in a single multilayer helical wave filter or multiple resonances can also be achieved by installing a multiplicity of discrete wave filters along the length of the lead as shown in FIG. 42.

Figure 43:
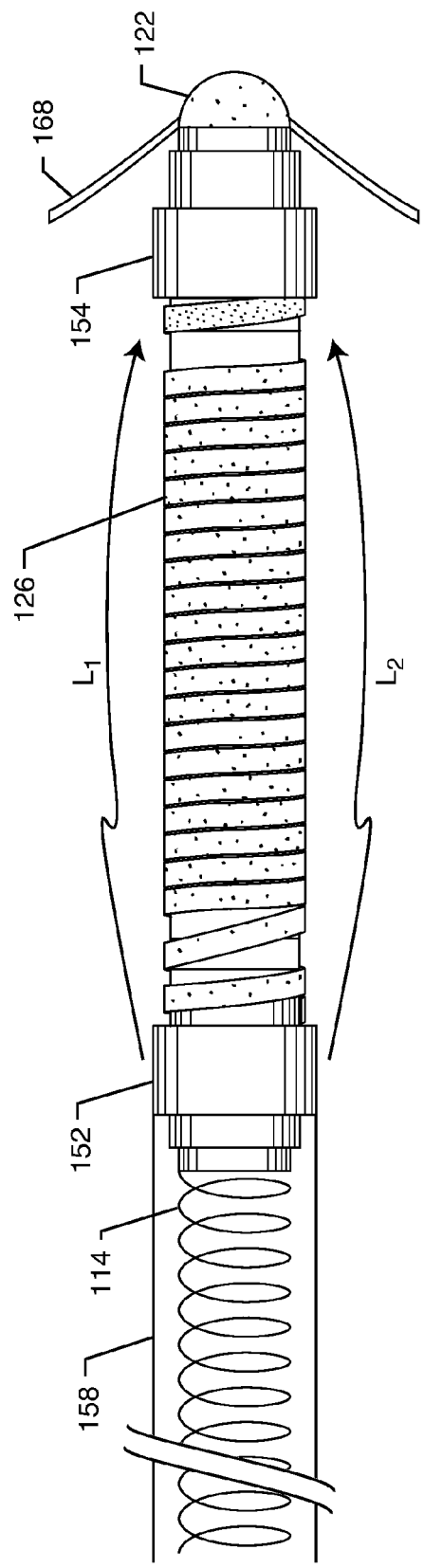
FIG. 43 is an elevational view of the multilayer helical wave filter of FIG. 11 shown in series with a passive fixation electrode and an implanted lead.

FIG. 43 illustrates the multilayer helical wave filter 126 with end caps 152 and 154 that were previously illustrated in FIG. 11. End cap 152 is shown attached to the conductor 114 of an implanted lead 158 which has an overall insulation sheath 158. In this case, by way of example, the multilayer helical wave filter 126 presents 2000 ohms at its primary resonant frequency of 64 MHz. However, in this configuration, since the multilayer helical wave filter is not have overall end to end insulation, there are undesirable RF leakage pads $L_1$ and $L_2$ through body tissue. The 2000 ohms of impedance desirably impedes the flow of MRI induced RF currents into body tissue through the electrode 122. However, if both ends of the multilayer helical wave filter are not isolated from each other, parallel paths result through body fluid (ionic fluid). This parallel path as measured by the inventors can be approximately 80 ohms. Referring back to FIG. 43, if an 80 ohms parallel path existed between the end caps 152 and 154, this would seriously degrade the impedance at resonance. The amount of degradation in impedance can result in RF currents flowing through the distal electrode 122 into body tissues that could result in life-threatening overheating of these adjacent tissues.

Figure 44:
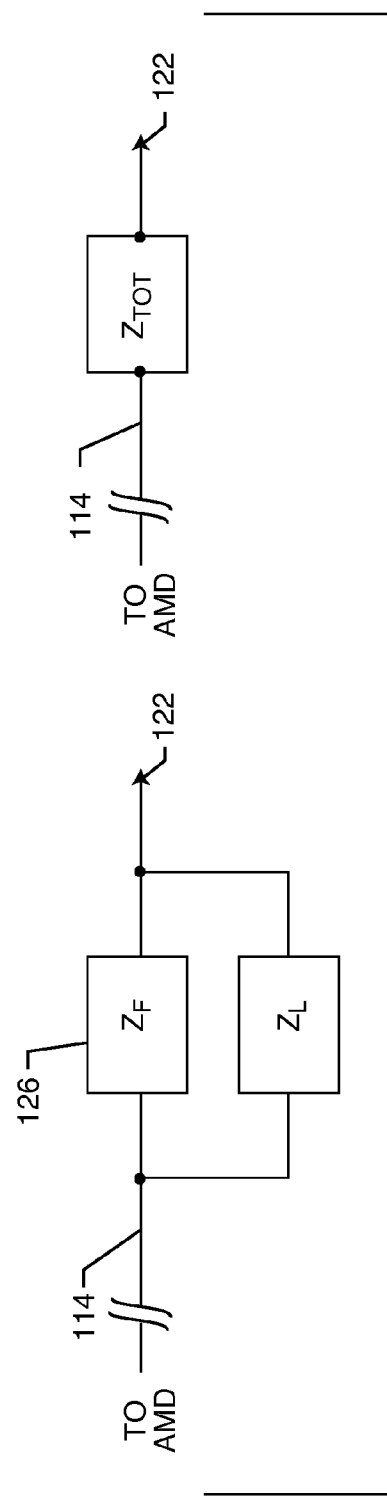
FIG. 44 is a schematic diagram which illustrates undesirable electrical leakage through body fluids in parallel with the multilayer helical wave filter of FIG. 43.

FIG. 44 is the schematic diagram taken from FIG. 43 showing the 2000-ohm impedance $Z_F$ of the multilayer helical wave filter 126. Shown in parallel with the multilayer helical wave filter 126 is the leakage path or 80-ohm impedance of the body tissues $Z_L$. Using the parallel resistance formula, when one has 80 ohms in parallel with 2000 ohms, the result is a combined impedance $Z_{TOT}$ of 76.82 ohms. As one can see, this is a catastrophic reduction of the impedance of the multilayer helical wave filter at resonance. It is a critical feature of the present invention that these body fluid paths be insulated so that they cannot cause leakage in parallel with the multilayer helical wave filter of the present invention.

Figure 45:
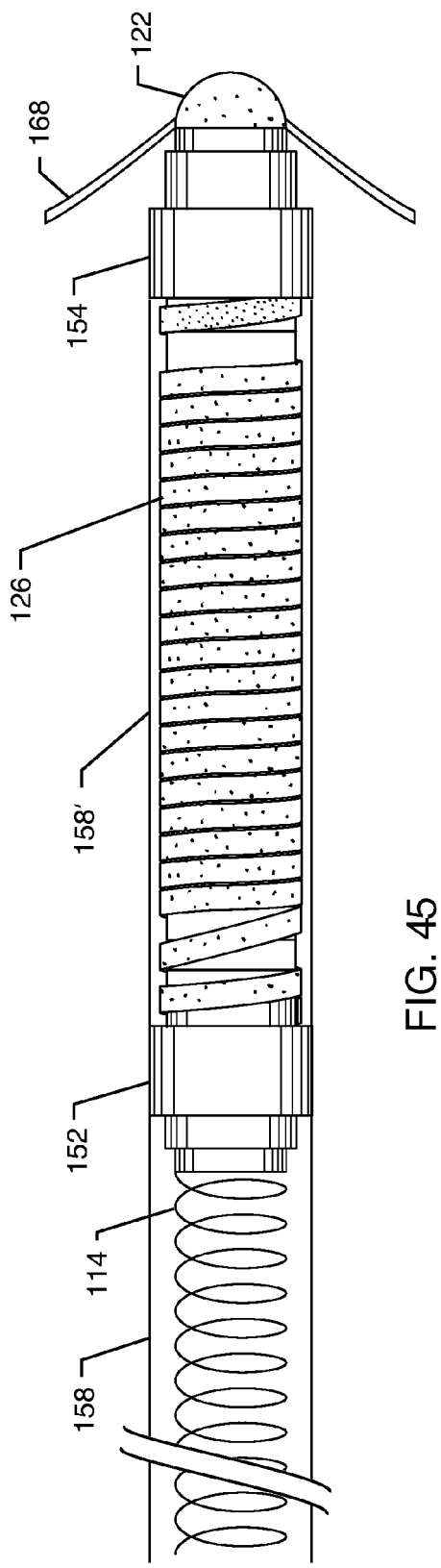
FIG. 45 is an elevational view of the multilayer helical wave filter of FIG. 43 with electrical insulation disposed over the multilayer helical wave filter such that electrical leakage through body fluids is prevented.

FIG. 45 is very similar to FIG. 43 except that the lead insulation 158' has been extended completely over the multilayer helical wave filter 126 of the present invention. Accordingly, the leakage paths through ionic body fluid $L_1$ and $L_2$ have been eliminated. In this case, the multilayer helical wave filter of FIG. 45 would present the full 2000 ohms of impedance at the MRI RF-pulsed frequency.

Figure 46:
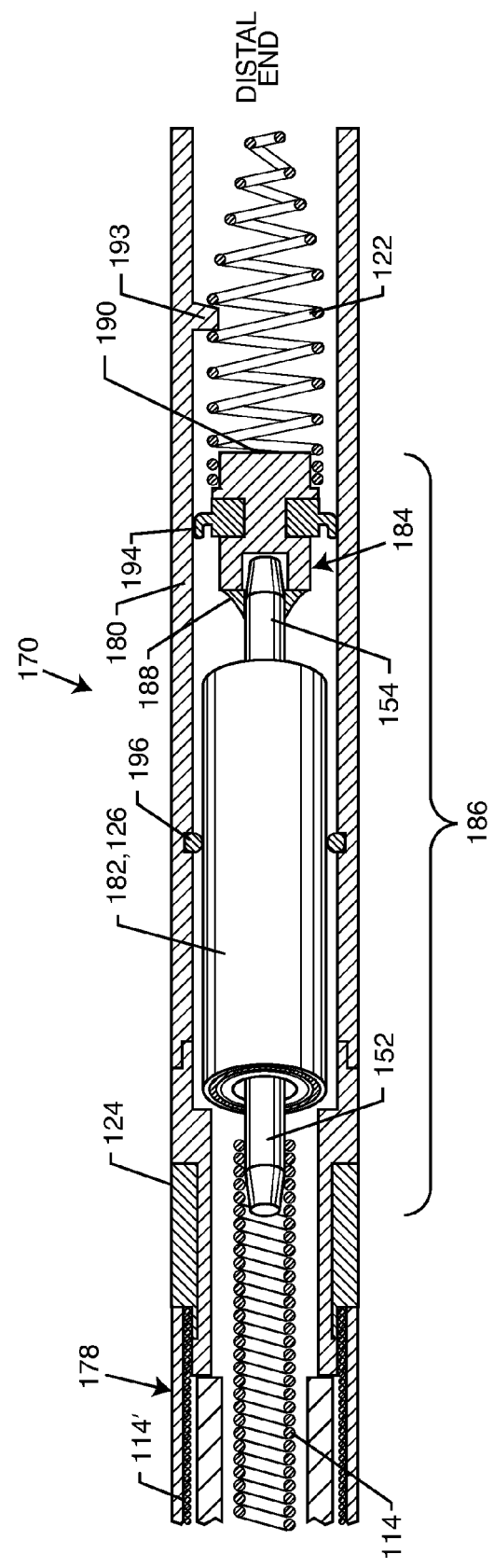
FIG. 46 is a sectional view of an active fixation electrode assembly embodying a multilayer helical wave filter with seals to prevent ingress of body fluids.

FIG. 46 illustrates an active fixation helix tip electrode assembly typically used in cardiac pacemaker applications. Shown is a multilayer helical wave filter 126 of the present invention. In this case, the multilayer helical wave filter is shown in a hermetic subassembly 180. Electrically isolating electric components in a medical electric lead with an active fixation electrode are described in US 2010/0324240 (see FIG. 10) the contents of which are incorporated herein.

FIG. 46 illustrates an exemplary bipolar active fixation electrode 170 which embodies a lead body 178, a coaxial conductor 114' for the ring electrode 124 and coaxial conductor 114 for the tip (active fixation helix) electrode 122, a collar 180, and the translatable casing 182 which houses a multilayer helical wave filter 126 of the present invention. The translatable casing 182 includes a pins 152 and 154. The pin 152 is electrically and mechanically connected to the tip electrode lead wire conductor 114 and the pin 154 is attached to the translatable seal assembly 184 which is also connected to a distal helix electrode 122. The distal helix electrode 122 is also known as an active fixation electrode. The pin 152, the casing 182, the pin 154 and the translatable seal structure 184 all form what is defined herein as a casing subassembly 186. A casing 182 which houses the multilayer helical wave filter 126 can be a hermetic seal as previously described in FIG. 10 or US 2010/0324640 or it can be a rigid or semi-rigid subassembly similar to that previously illustrated in FIG. 11 herein. As previously described, it is very important that body fluids be prevented from encroaching across the two ends 152 and 154 of casing 182 and the multilayer helical wave filter 126. As previously described, these parallel ionic conduction paths can seriously degrade the impedance of the wave filter at resonance.

Referring once again to FIG. 46, there will typically be a laser weld (not shown) electrically and mechanically connecting the tip conductor 114 to pin 152. There is also a laser weld 188 connecting pin 154 to a weld sleeve 190 of the translatable seal assembly 184. The weld sleeve 190 may be attached to the pin 154 in any known technique including laser welding, bonding, crimping, adhering, brazing, other forms of welding, or any other suitable method. The weld sleeve 190 is typically laser welded to the helix electrode 122. During transvenous insertion, the active fixation helix tip electrode 122 is retracted (as shown) so that it will not inadvertently stab or poke into body tissues during lead insertion. When the physician has positioned it in the desirable location (perhaps inside the cardiac right ventricle), then the physician takes a special tool and twists the proximal end of lead body 178 tip conductor 114 which causes the entire conductor 114 and casing subassembly 182 to rotate. As the distal helix electrode 122 rotates, it engages a guide 192 which causes the helix 122 to extend and screw into body tissue. The guide 192 may be formed as part of the collar 180 and engages the tip electrode 122 when the tip conductor 114 is rotated. The rotation causes the helical tip electrode 122 to rotate within the collar 180 and thereby translate in a forward manner. At the same time the tip electrode 122 is advancing relative to the collar 180, it is engaging with body tissue by being screwed directly into the tissue forming an attachment. The tip electrode 122 can be rotated in the opposite direction by the tip conductor 114 and thereby disengaged from the tissue for removal and/or reattachment at a different location. This is a method of active affixation which is well known in the art.

The flexible seal 194 of FIG. 46 slides against the interior of the collar 180 thereby preventing the entrance of ionic body fluids into the inside of the lead body 178. The seal 194 may be bonded, molded, adhered, or formed onto the weld sleeve 190 by any suitable means. The seal 194 can be formed in a multitude of ways appreciated by those skilled in the art, such as multiple wipers, o-rings, thin disks or sheets, and various molded profiles.

There is a secondary optional O-ring seal 196 as shown in FIG. 46. The optional O-ring seal 196 is disposed between the inside diameter of the lead collar 180 and the outside diameter of the translatable housing and multilayer helical wave filter 126. The purpose of seal 194 and the O-ring seal 196 is to ensure that ionic body fluids cannot be disposed across the important electrical path between pins 152 and 154. Ionic body fluids can represent an undesirable parallel path as low as 80 ohms. Over time, due to bulk permeability, body fluids will penetrate into the interior of the lead body 178. However, this is an osmotic type of action. The resulting fluids that would occur over long periods of time inside the lead body 178 would be distilled and free of ionic contaminants (de-ionized). This means that they would be less conductive of high frequency electrical signals from one end to the other of the multilayer helical wave filter 182, 126. The presence of optional O-ring 196 is desirable in that it also presents a high impedance to such a parallel circuit path. The casing 182, 126 may also have a conformal insulative coating (not shown) for further electrically isolating terminals 152 and 154 such that a parallel path through body fluid is further impeded. The insulative coating may be formed from any suitable material, such as a dielectric material, including, but not limited to parylene, ETFE, PTFE, polyamide, polyurethane and silicone. It will be understood that the exemplary embodiment of FIG. 46 may work with or without such coatings. The casing 182 may be a metallic and hermetically container or any biocompatible insulative material. The multilayer helical waver filter of the present invention is hollow on the inside for convenient insertion of additional wires.

From the foregoing it will be appreciated that, the multilayer helical wave or bandstop filters 126 of the present invention resonate at one or more frequencies and thereby provide a very high impedance at a selected resonant frequency(ies) or range of frequencies, and comprises an elongated conductor 140 having at least one planar surface. The elongated conductor includes a first helically wound segment 142 having a first end and a second end forming a first inductor component, a return wire or return coil 144, and a second helically wound segment 146 having a first end and a second end forming a second inductor component. The first and second helically wound segments share a common longitudinal axis and are wound in the same direction wherein induced currents also flow in the same direction. The return wire or return coil 144 extends substantially to the length of the first and second helically wound inductor segments to connect the second end of the first helically wound segment to the first end of the second helically wound segment.

The planar surface or surfaces of the first inductor faces the planar surface or surfaces of the second inductor and are coated with a dielectric insulative layer. Parasitic capacitance is formed between the planar surfaces of both the inner and outer inductors and adjacent coils. The combination of the inductors and the parasitic capacitances form a multi-helical wave filter, which in preferred embodiments act as a bandstop filter. By providing a very high impedance at MRI pulsed frequencies, the multilayer helical wave filter of the present invention prevents the leadwire and/or its distal electrodes that are in contact with body tissue from overheating.

Figure 47:
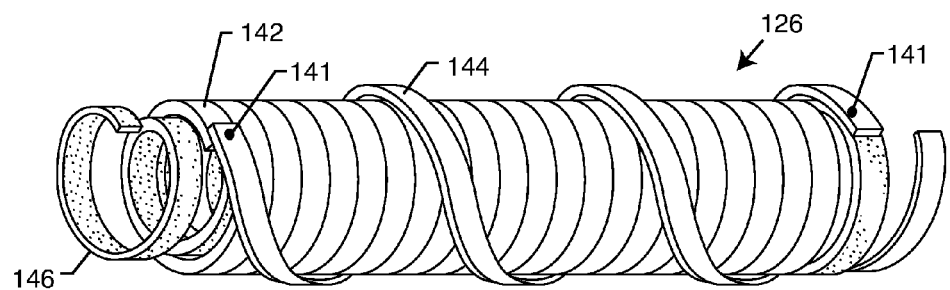
FIG. 47 is a multihelical wave filter similar to FIG. 27, now with the return coil wound in a similar rotational direction.

FIG. 47 is a multihelical wave filter 126 which is very similar to the multihelical wave filter previously illustrated in FIG. 27. In FIG. 47, the coiled return wire 144 is wound in the opposite direction. Winding the return coil in the opposite direction changes the overlapping magnetic fields and also the parasitic capacitance. FIG. 47 is a more efficient structure in that it will yield a higher impedance at resonance as compared to the structure illustrated in FIG. 27. In FIG. 47, there is an inner coil 146 that is wound inside of the outer coil 142. By the nature of the novel return wire 144 of the present invention, induced RF currents flow in the same direction thereby maximizing the impedance at resonance of the bandstop filter.

Figure 48:
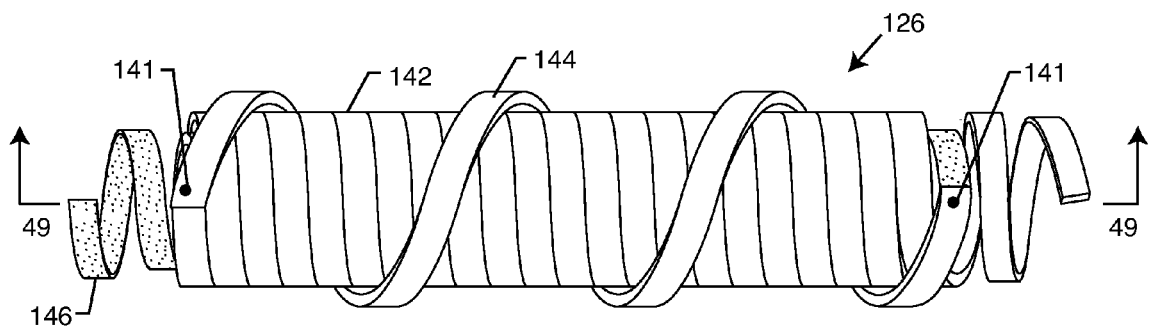
FIG. 48 is a multihelical wave filter similar to FIG. 28, now with the return coil wound in a similar rotational direction.

FIG. 48 is very similar to FIG. 28 except that again, the coiled return wire 144 is wound in the opposite direction. The same comments apply here as previously in FIG. 47. In FIG. 48, the inner coil 146 and the outer coil 142 are wound in opposite directions as compared to FIG. 47. In addition, the return wire 144 is also wound in the opposite direction. In other words, as long as one is consistent, the coils can all be wound as shown in FIG. 47 or in the reverse configuration as shown in FIG. 48.

Figure 49:
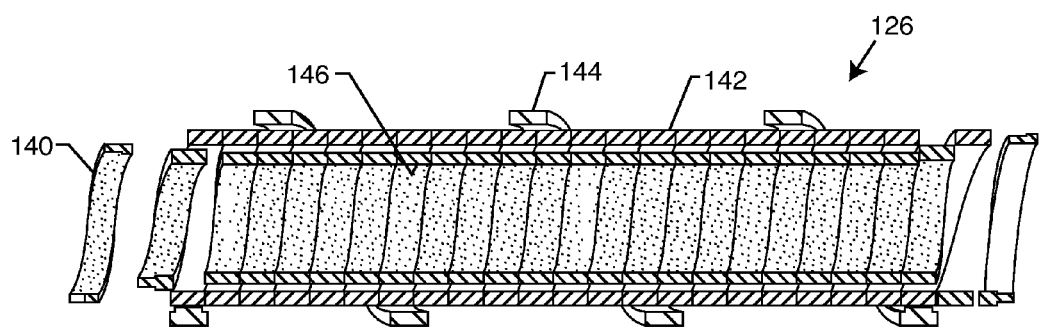
FIG. 49 is a sectional view taken from section 49-49 of FIG. 48.

FIG. 49 is a sectional view taken from section 49-49 from FIG. 48 illustrating a first helically wound segment 146, a second helically wound segment 142 and the return wire segment 144. Referring once again to FIGS. 47 and 48, in comparison to FIGS. 27 and 28, there is an ease of manufacturing advantage to the structures as illustrated FIGS. 47 and 48. This is a rectangular conductor as shown or a round or other shape (not shown) can be used in a continuous winding wherein, the inner coil is formed in one direction and then the return coil is formed in the other direction. Then the outer coil is formed as illustrated. In this way, the coil is wrapped back and forth, again to facilitate ease of construction. At resonance, there is a considerable frequency shift between the structure as illustrated in FIG. 47 and that of FIG. 27. The reason for this is that the parasitic capacitance and the overlapping inductive fields change the values in the equivalent circuit. The graph of the resonant frequency is shown typically in FIG. 24. By way of example, a prototype wound in accordance with FIG. 27 has a resonant frequency of approximately 152 MHz. Using approximately the same inner and outer coils and the same pitch for the return coil, the resonant frequency of the structure illustrated in FIG. 47 shifted to just below 116 MHz. Referring to FIG. 23, one can see capacitor 148, which represents the parasitic capacitance of the return wires as it overlaps the inner windings. In FIG. 47, this value of capacitance is significantly different as compared to winding the return wire in the opposite direction, as shown in FIG. 27.

Figure 50:
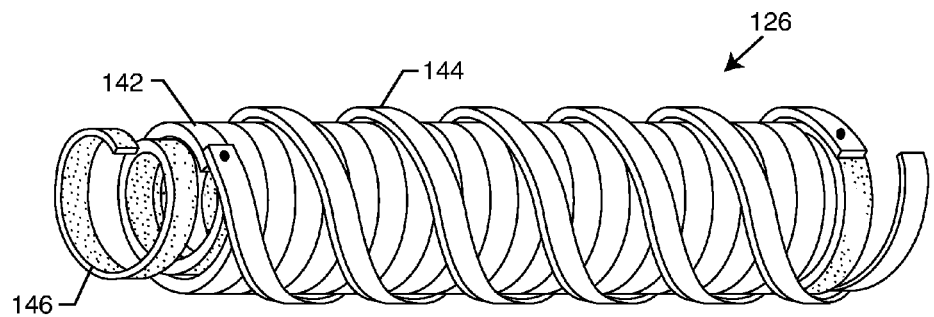
FIG. 50 is similar to FIG. 47, now showing the return coil more closely spaced.

FIG. 50 illustrates the same structure as previously described in FIG. 47 except that the return wire coils 144 are more closely spaced and there are more of them. In the present invention, the coil spacing of the return wire 144 can vary anywhere from widely spaced, to tightly aligned such that the return wire coils would be wound adjacent similar to those shown in outer coil 142.

Figure 51:
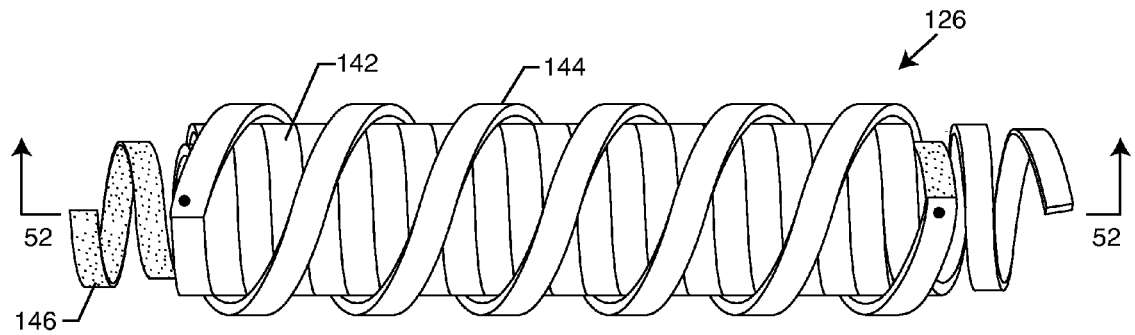
FIG. 51 is similar to FIG. 48, now showing the return coil more closely spaced.

FIG. 51 is very similar to FIG. 48 illustrating the same principle wherein, the number of return wire coils 144 per inch can be increased.

Figure 52:
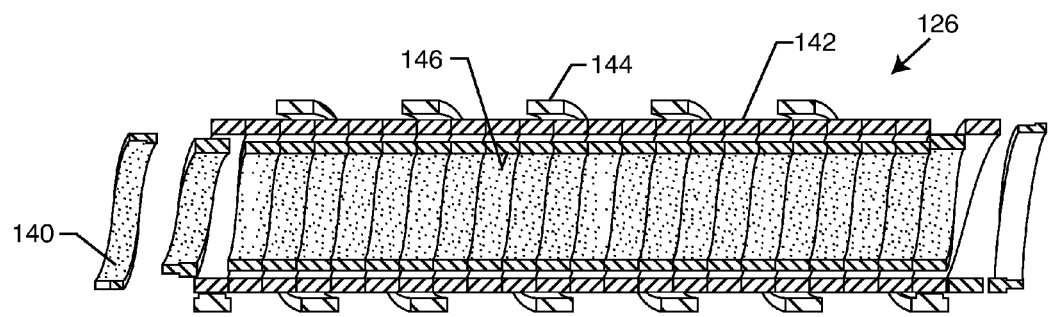
FIG. 52 is a sectional view taken from section 52-52 of FIG. 51.

FIG. 52 is a sectional view taken from section 52-52 from FIG. 51. In FIG. 52, one can see that the return coils 144 are more closely spaced as compared to return wire coils 144 previously illustrated in FIG. 49.

Figure 53:
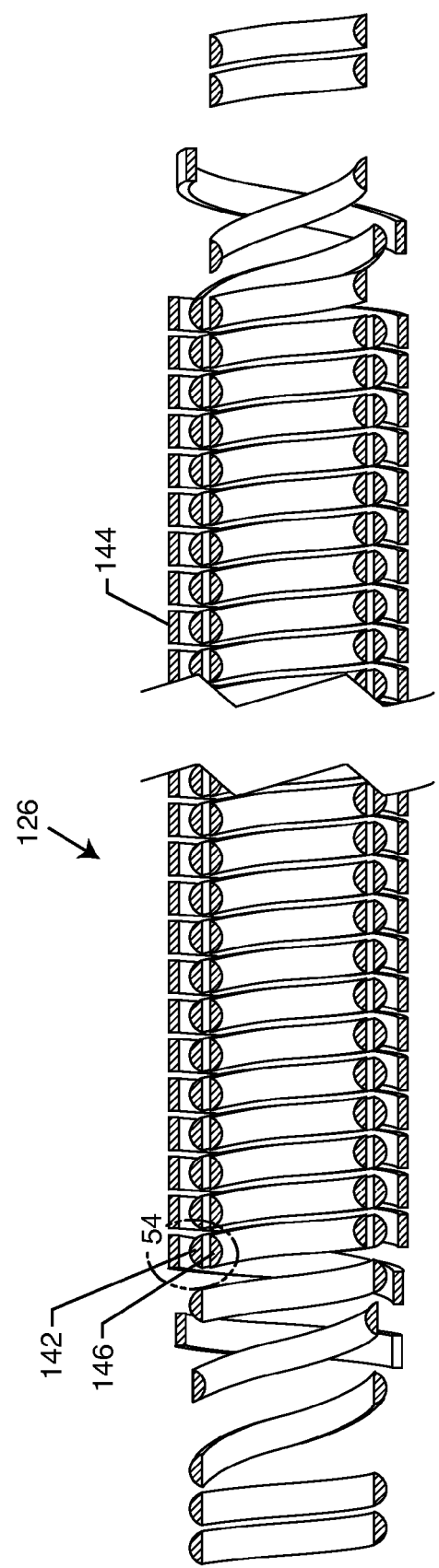
FIG. 53 is a sectional view similar to FIG. 52, now showing a D-shaped wire.
Figure 54:
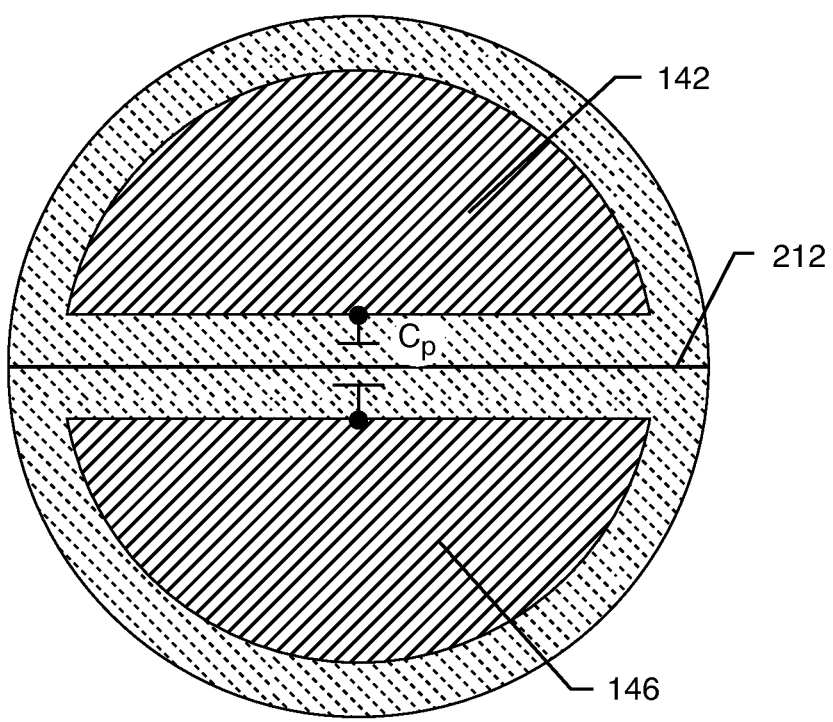
FIG. 54 is an enlarged view of the structure of FIG. 53 taken along lines 54-54.

FIG. 53 is very similar to FIG. 52 except that the return wire coil 144 is shown very closely spaced. In other words, there are a much greater number of return wire coils as compared to FIG. 52 or 49. Importantly, the inner coil 146 and the outer coil 142 are of a D-shaped wire such that the wire forms a semi-circle. These wires are, of course, insulated (not shown) so that a dielectric layer is formed between them. This allows for a relatively high parasitic capacitance $C_P$ to form between these two layers which is best illustrated in the blown up view shown in FIG. 54 taken from section 54-54 from FIG. 53. Referring once again to FIG. 54, one can see that there is a flat surface 212 between conductors 142 and 146. This makes for a highly controllable effective capacitance area (ECA) and maximizes the parasitic capacitances as opposed to say two round wires.

Figure 55:
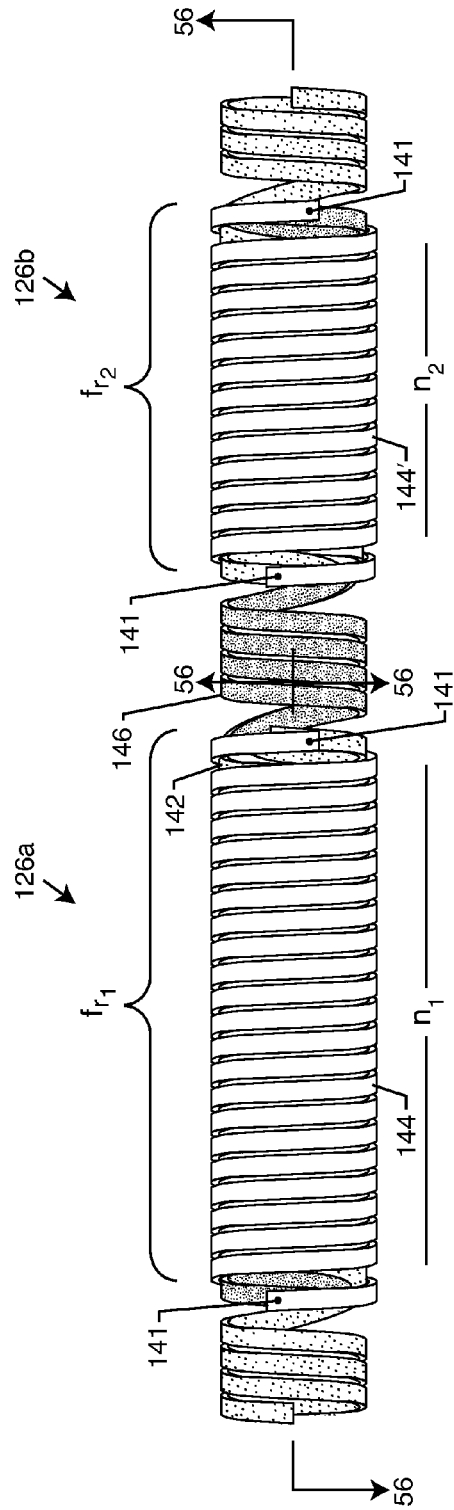
FIG. 55 is a multi-section and multilayer helical bandstop with a continuous inner coil.

FIG. 55 illustrates a multi-section and multilayer helical bandstop filter which has a continuous inner coil 146. There is also an outer coil 142 which is discontinuous and unique to the two sections fr1 and fr2. Referring once again to FIG. 55, one can see that in the fr1 section, there is a much higher turn count n1 compared to the relatively lower turn count n2 of the fr2 section. Referring once again to FIG. 55 and FIG. 56, one can see that there are two different return coil segments 144 and 144', which yields two discrete bandstop filters with a common inner core 146. The schematic diagram in FIG. 57 illustrates two simplified bandstop filters consisting of an inductor L in parallel with a capacitor C. In section fr1, there is a different inductance of capacitance L1 and a different value of total parasitic capacitance C1 as compared to the resonant section fr2, which has a different value of equivalent value L2 and a different value of parasitic capacitance C2. Again, the schematic diagram in FIG. 57 is simplified and does not show all of the individual parasitic capacitances between adjacent layers and between adjacent turns.

Figure 56:
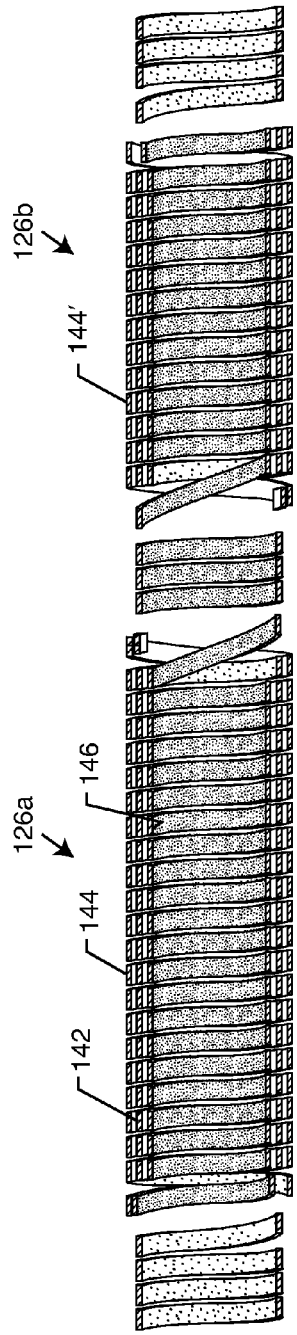
FIG. 56 is a sectional view of the structure of FIG. 55 taken along lines 56-56.
Figure 57:
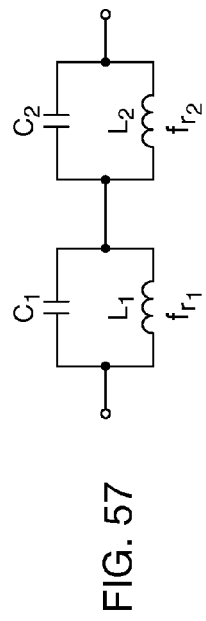
FIG. 57 is an electrical schematic diagram of the structure of FIGS. 55 and 56.

FIGS. 58 and 59 are very similar to FIGS. 55 and 56 except that there is an inner coil 146 and 146', which is discontinuous and then a continuous outer coil 142, which is continuous throughout and two different return segments 144 and 144'. In other words, in FIGS. 58 and 59 where 142 is continuous whereas, in FIGS. 55 and 56 where 146 is continuous. Manufacturing of multilayer helical inductors for human implant applications is a challenging one because of the need for complete biocompatibility. This means that all of the material must be nontoxic and long term compatible with body fluid. In addition, they must not erode over time such that electrical connections would be degraded.

Figure 60:
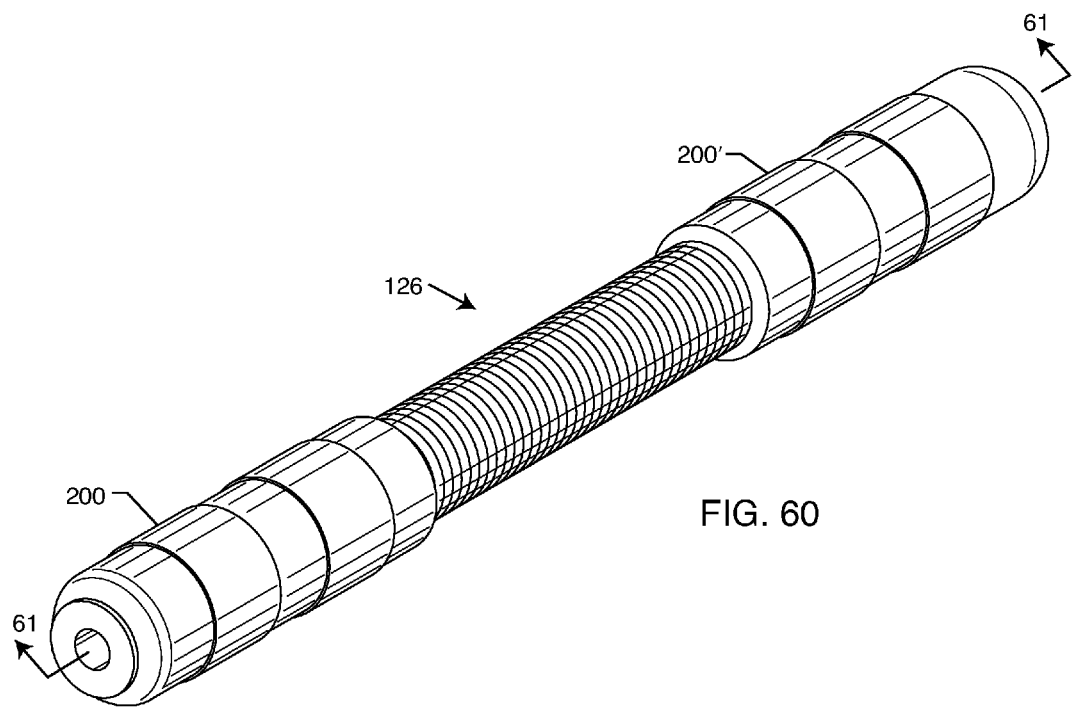
FIG. 60 is a perspective view of an embodiment of a multilayer helical bandstop filter with crimp structures.

FIG. 60 illustrates an embodiment of the present invention that is applicable to any of the previous drawings of multihelical bandstop filters. In this case, there are two end caps structures 200 and 200' which facilitate easy connection to an implantable lead conductor.

Figure 61:
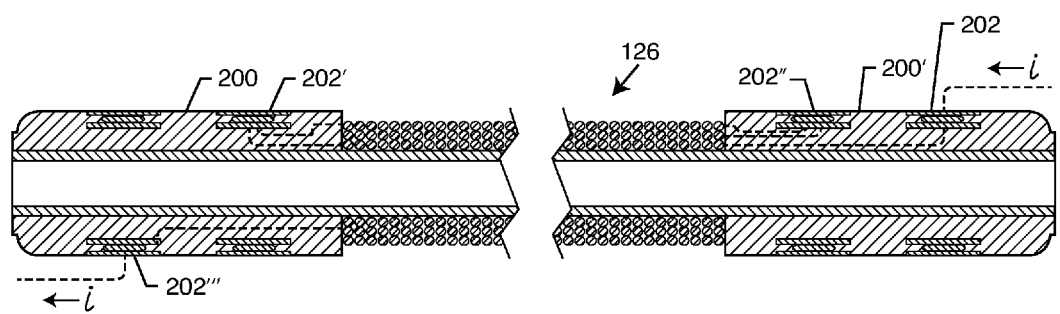
FIG. 61 is a sectional view of the structure of FIG. 60 taken along lines 61-61.

FIG. 61 is a sectional view taken from section 61-61 from FIG. 60 showing the interior structure of the multihelical bandstop filter 126 and the end cap structures 200 and 200'. One can see that there are crimp areas 202, 202', 202" and 202'''. These crimp structures make all of the required electrical connections for any of the multilayer helical bandstop filters of the present invention. An advantage to crimping is that a very solid mechanical and electrical connection is made without the need for laser welding or the like. One of the problems associated with laser welding is that it tends to burn the electrical insulation or dielectric material which coats all of the wires of the present invention. By stripping away this electrical insulation and then crimping it between two biocompatible metal structures, such as platinum, one makes a highly reliable biocompatible nontoxic stable electrical connection. The three layers of coiled wire that form that bandstop filter 126, in this case, incorporate round wire. In accordance with the present invention, this round wire would have to be insulated such that adjacent turns don't short out to each other. Importantly, the insulation between coil layers and turns also creates a parasitic capacitance which yields resonant bandstop filter performance. In one embodiment (not shown), the wires could be cored. It is well known in the prior art that defibrillator leads have a solid silver center surrounded by an MP35N biocompatible outer coating. The presence of the silver greatly increases the conductivity of the wire. However, if one were to laser weld to this type of cored wire, the silver core would be exposed, which would not be considered completely biocompatible. Accordingly, the crimping type connections shown in FIG. 1 are particularly advantageous such that, the integrity of the core of the wire is preserved and the core would not be exposed to body fluids. Referring once again to FIG. 61, one can see that round wires have been used to create the bandstop filter portion 126. It will be obvious to those skilled in the art that any of the previously described wire, such as rectangular or D-shaped and the like could also be used.

Figure 62:
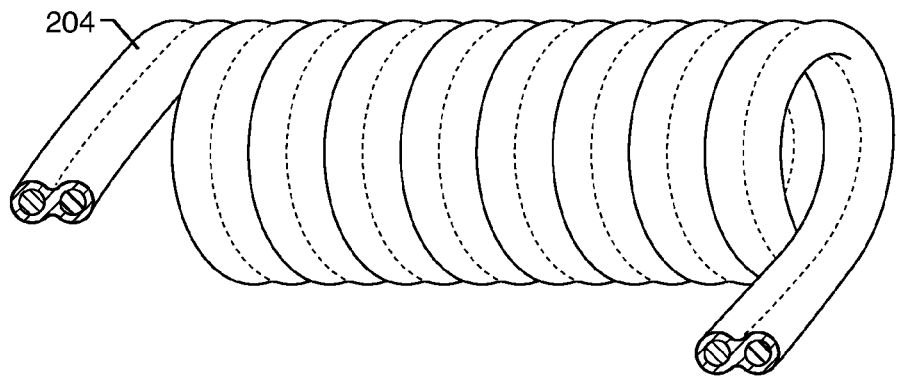
FIG. 62 is a first step of a manufacturing process of an embodiment of a multilayer helical bandstop filter using a double insulated wound wire.

FIG. 62 illustrates another method of efficiently manufacturing a multilayer helical inductor of the present invention. In this case, one uses a double insulated wound wire 204 similar to speaker wires typically found in a stereo store.

Figure 63:
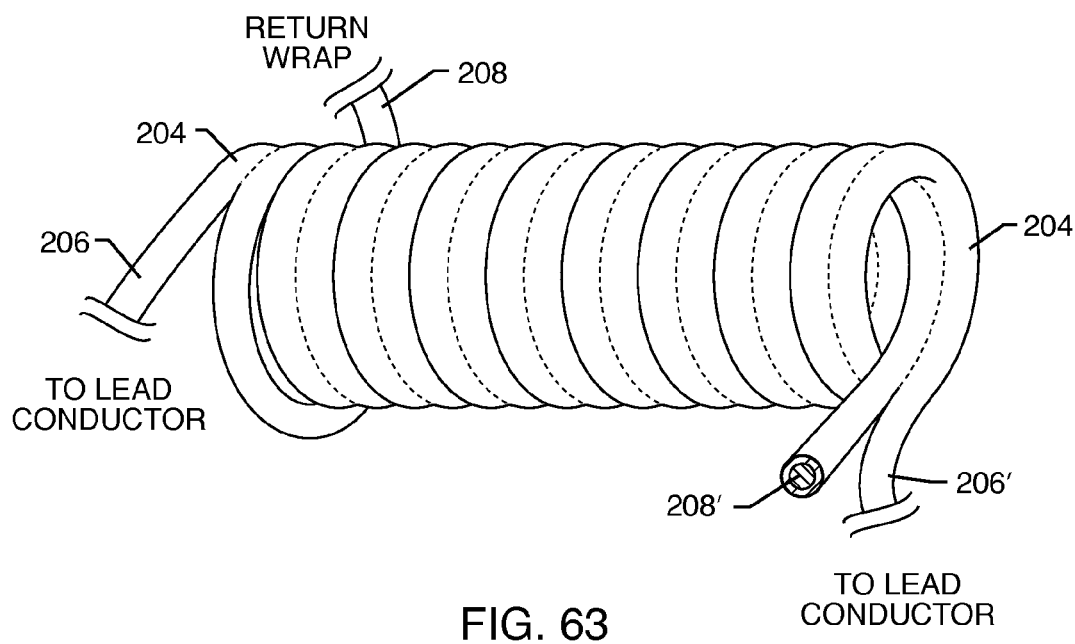
FIG. 63 is a second step of the manufacturing process of the structure of FIG. 62.
Figure 64:
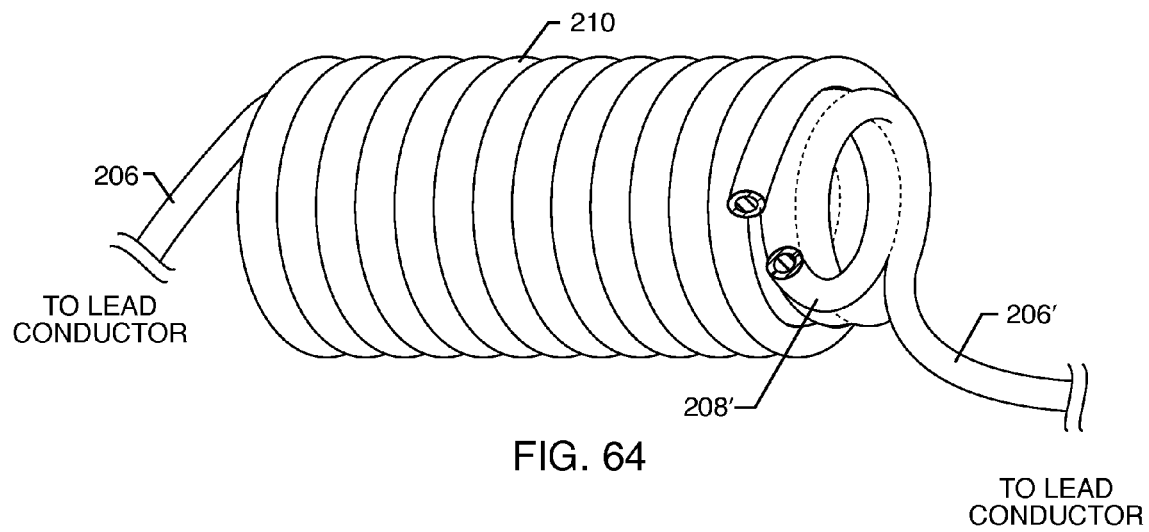
FIG. 64 is a third step of the manufacturing process of the structure of FIG. 62.
Figure 65:
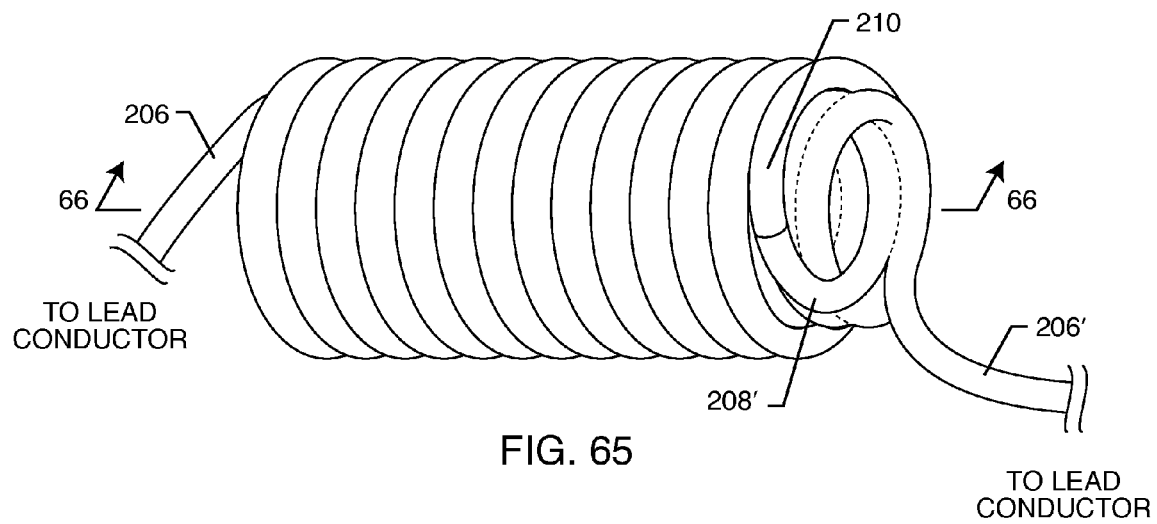
FIG. 65 is a fourth step of the manufacturing process of the structure of FIG. 62.

In FIG. 63, one can see where the doubled wire 204 has been split into a portion that will be connected and aligned with the lead conductor and after it's split and separated, its other half 208 will be routed to a return route or a return segment. A similar thing happens on the other end of the coil wherein, the doubled wire 204 is split into a portion 206' that will go inline or in series with the lead conductor and another portion 208'. A return wire (not shown) would be either routed straight or coiled in either direction between ends 208 and 208'. Referring back again to FIG. 62, the first step is to route the double wire on a mandrel. In FIG. 63, the second step is to separate the ends of each wire. Then in FIG. 64, a return wrap or coil 210 is wound outside of both the inner wires 204. This return wire 210 acts as a single wire. On the left side, the return wire 210 would be electrically connected to return wrap 208 (not shown) and on the right hand side (as illustrated in FIG. 65), the return wrap 210 would be electrically connected to the split end of the dual wire 208'. This completes the structure, in that, we now have a multilayer helical coil of the present invention formed from a dual cable-type wire. The advantage of this structure is significantly less complicated assembly and also a reduced assembly cost.

Figure 66:
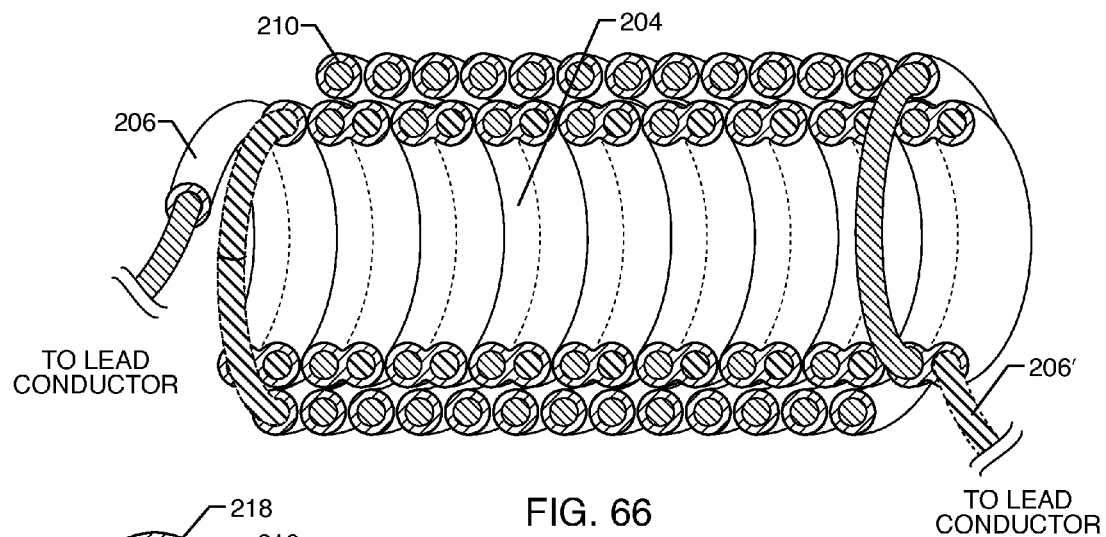
FIG. 66 is a sectional view of the structure of FIG. 65 taken along lines 66-66.
Figure 67:
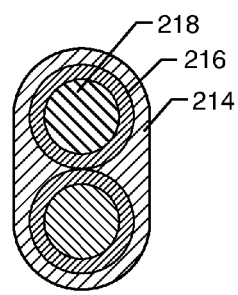
FIG. 67 is an embodiment of a double wire.
Figure 68:
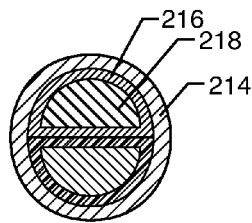
FIG. 68 is another embodiment of a double wire.
Figure 69:
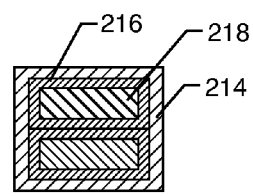
FIG. 69 is another embodiment of a double wire.
Figure 70:
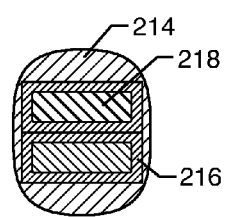
FIG. 70 is another embodiment of a double wire.
Figure 71:
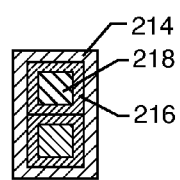
FIG. 71 is another embodiment of a double wire.
Figure 72:
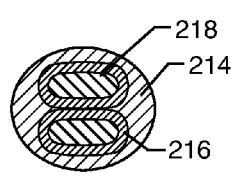
FIG. 72 is another embodiment of a double wire.

FIG. 66 is a sectional view taken from section 66-66 from FIG. 65 showing the double inner wire 204 and the single return wire wrap 210.

FIGS. 67 through 72 show alternative wire shapes along with their associated electrical insulation 214. As one can see, round wires, D-shaped wires, rectangular wires, square wires or even oval or electrical wires could be used in the present invention. Referring back to FIGS. 67 through 72, one can see there are two layers of insulation 214 and 216. In this case, all of the different wire shapes are individually insulated and then there is an over mold or insulation 214 to provide addition insulation, but more importantly, to hold them mechanically and structurally together into the shapes as illustrated.

Figure 73:
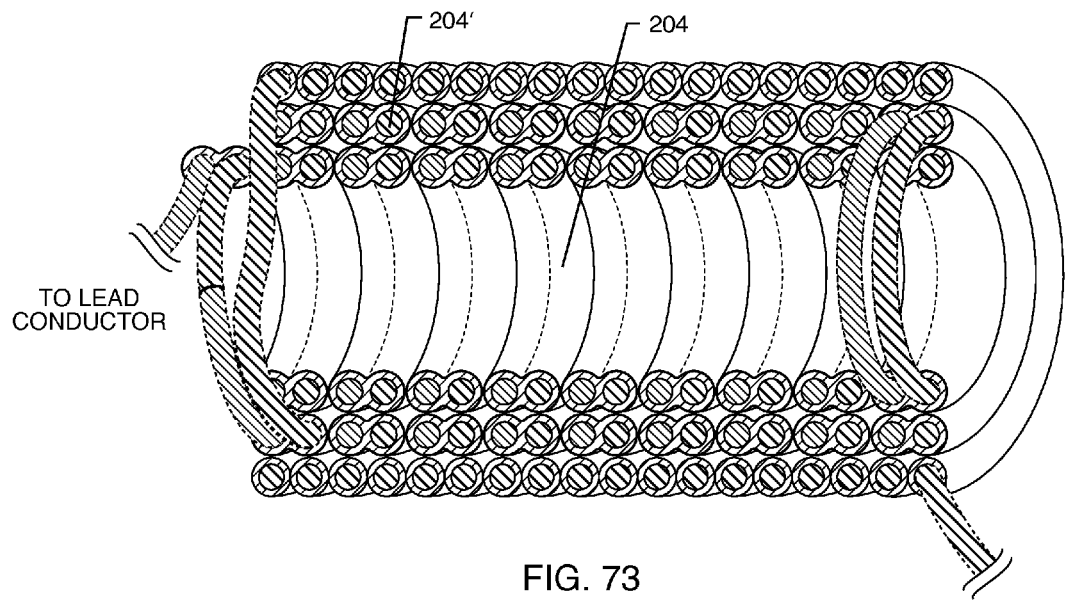
FIG. 73 is a sectional view of another embodiment of a multilayer helical bandstop filter using a double insulated wound wire.
Figure 74:
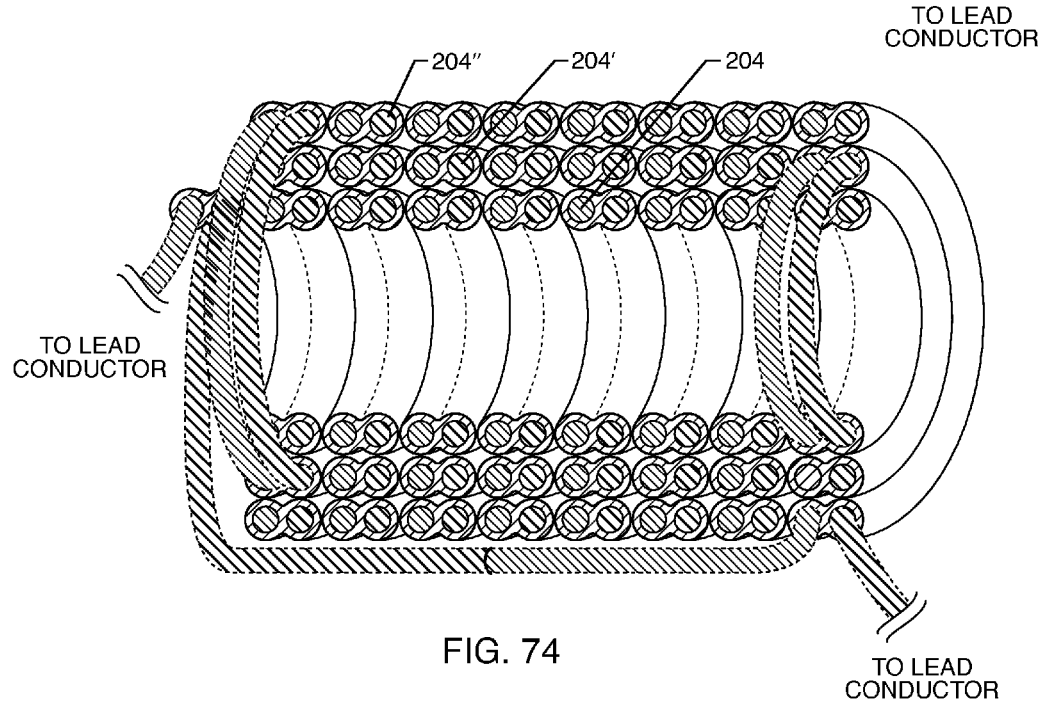
FIG. 74 is a sectional view of another embodiment of a multilayer helical bandstop filter using a double insulated wound wire.

FIGS. 73 and 74 are similar to FIG. 66 except that additional layers of double wires are used. In FIG. 73, there are two layers of doubled wires 204 and 204'. In FIG. 74, there are three layers 204, 204' and 204".

Figure 75:
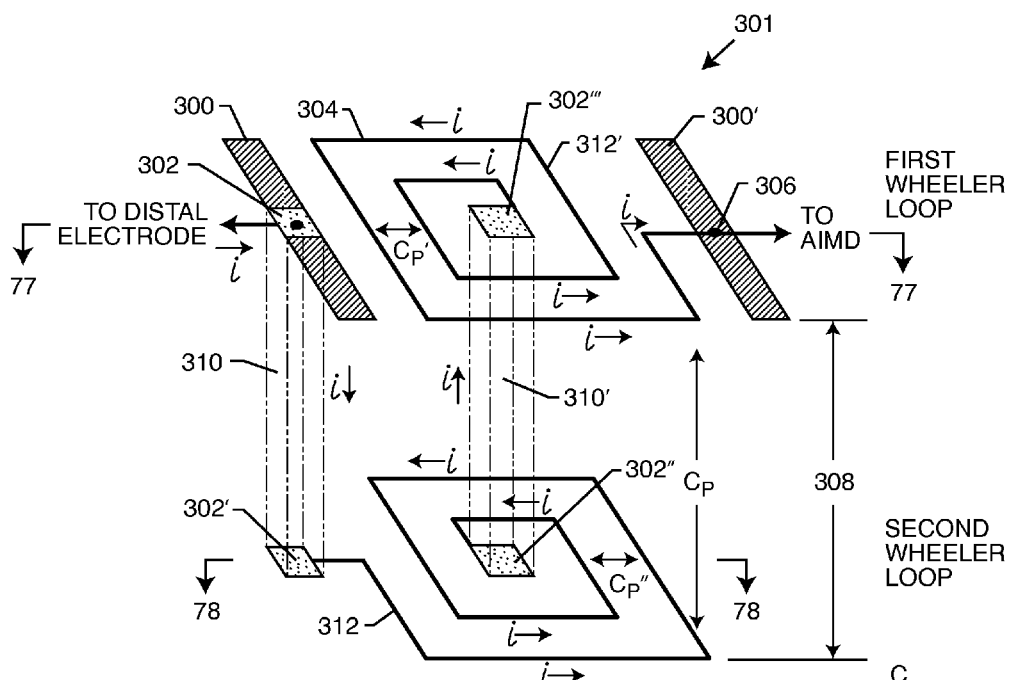
FIG. 75 is a simplified dual layer Wheeler spiral with similar flowing induced RF currents between layers.
Figure 76:
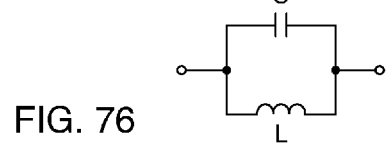
FIG. 76 is an electrical schematic of the structure of FIG. 75.

FIG. 75 illustrates a dual layer square Wheeler spiral multihelical inductor bandstop filter of the present invention. There is a contact or circuit trace pad 300, which is electrically conductive and is connectable to an implanted lead which has a distal electrode in contact with biological cells. The implantable lead, when exposed to an MRI environment, can pick up high amplitude RF pulse signals, which are routed as a circuit current i. One can see the circuit current entering the contact pad 300 and then being directed down through via hole connection 302 through the via hole conductive fill material 310 to the layer below at contact pad 302'. Contact pad 302' is routed to a circuit trace 312, which forms a second square Wheeler spiral inductor in stacked relationship with the first Wheeler spiral terminating at contact pad 302". It will be obvious to those skilled in the art that the Wheeler spiral could be round, oval, rectangular, irregular or the like. Contact pad 302" is also connected to a via hole with via hole conductive fill material 310, which makes contact to the upper via hole pad area 302'''. Contact pad 302''' is also connected to a circuit trace 312' as shown. The RF currents are routed upwards from contact pad 302" to contact pad 302''' and then the currents are routed along the circuit trace 312' where they exit the Wheeler spiral and terminate at contact pad 300'. Contact pad 300' has an electrical connection 306 where the circuit trace 312 is terminated. There are additional contacts between contact pad 300' and to the AIMD electronic circuit board, which may contain therapeutic delivery circuits and/or biological sensing circuits. These circuits and interconnections are not shown. Referring once again to FIG. 75, it is an essential feature of the present invention that the induced RF currents in the upper circuit trace layer 312' are in the same direction as the RF circuit currents induced in the lower circuit trace 312. In this case, all of these currents are shown counter-clockwise. Those skilled in the art will realize that these circuit currents are alternating at the frequency of the MRI RF-pulsed frequency. For example, for a 1.5 Tesla MR scanner, the RF pulsed frequency is 64 MHz. That means that these induced currents would switch directions 64 million times per second. For sake of clarity, they are shown in one direction which would be representative of only one portion of the RF-pulsed current sinusoid. In accordance with the present invention, there is a parasitic capacitance $C_P$ formed between the adjacent layers of the Wheeler spiral inductors. There is also turn-to-turn parasitic capacitance CP' formed between the circuit traces 312' of the upper layer and there is also a parasitic capacitance CP" formed in the circuit traces 312 of the lower layer. When one does extensive modeling of the structure as illustrated in FIG. 75, one can reduce it down to a simplified schematic, as shown in FIG. 76 wherein, all of the parasitic capacitance form a single lump capacitor element C and the inductances formed by the upper and lower layer, in the inductive field overlaps (mutual inductance) form a lump inductance L, as shown in FIG. 76. As one can see in FIG. 76, when one has a capacitor in parallel with an inductor, one has a bandstop filter, which can be designed to be resonant at an MRI RF-pulsed frequency. When a bandstop filter is resonant, it provides a very high impedance at the resonant frequency, thereby preventing the flow of RF currents. In a preferred embodiment, the structure as illustrated in FIG. 75 would be a bandstop filter placed at, near or within a distal electrode. By presenting a high impedance at RF frequencies, one would prevent dangerous RF currents from entering into adjacent body tissues, thereby causing direct damage or overheating of adjacent structures.

Figure 77:
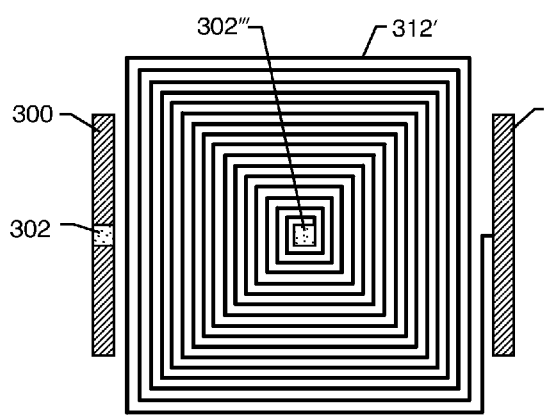
FIG. 77 is a top down view of the structure of FIG. 75 along lines 77-77.

FIG. 77 is a top down view of the upper layer taken along section 77-77 from FIG. 75. One can see the two contact pads 300 and 300' as well as the Wheeler spiral circuit trace 312'. Also the via hole connection pads 302 and 302''' are shown.

Figure 78:
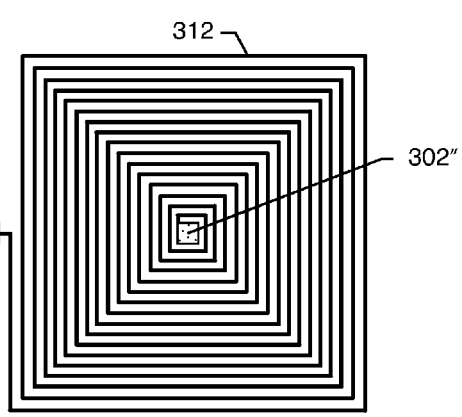
FIG. 78 is a top down view of the structure of FIG. 75 along lines 78-78.

FIG. 78 is a top down view of the lower layer taken generally along section 78-78 from FIG. 75. In this case, one can see the circuit trace 312 and contact pads 302' and 302". As previously mentioned, this is a square Wheeler spiral. It is also possible as a round Wheeler spiral or any other shape. It is apparent that FIGS. 77 and 78 show an increased number of turns as compared to FIG. 75.

Figure 79:
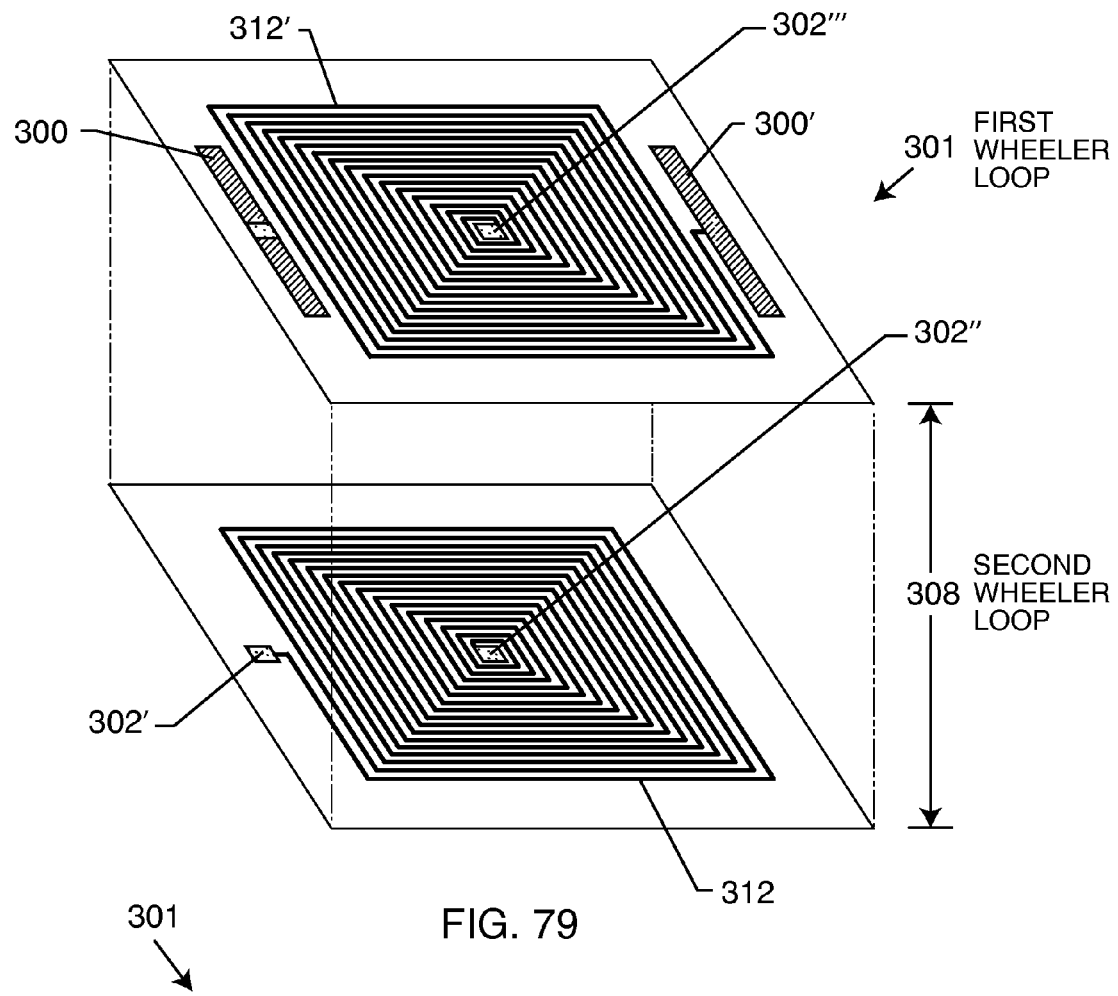
FIG. 79 is an expanded isometric view of the structure of FIGS. 77 and 78.

FIG. 79 is an isometric view of the multilayer Wheeler spiral helical bandstop filter taken from FIGS. 75, 77 and 78. One can see that there is a thickness between the two layers separated by an insulative layer 308. Referring back to FIG. 75, one can see the thickness 308. In this case, it is exploded so one can see all the internal circuitry. In FIG. 79, the thickness between adjacent layers 308 is also greatly exploded so one can see the Wheeler spiral shapes of the upper and lower sections.

Figure 80:
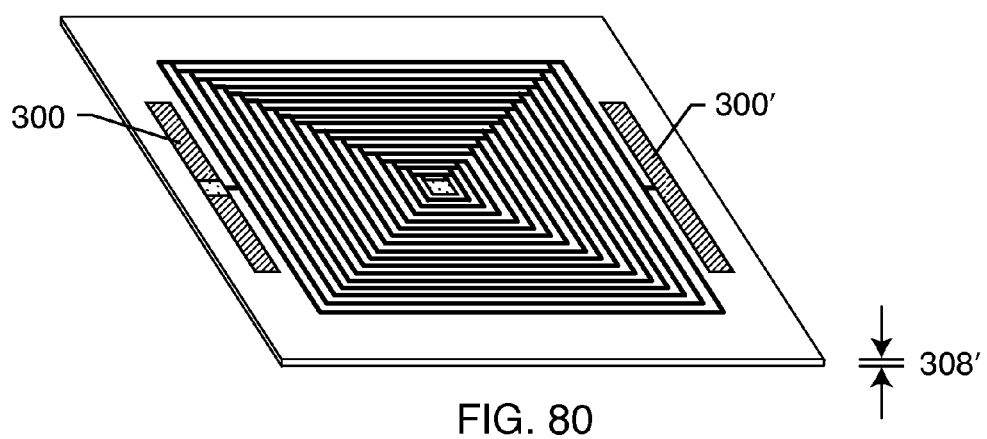
FIG. 80 is an assembled isometric view of the structure of FIG. 79.

FIG. 80 is more realistic of the actual dielectric thickness 308' wherein, the Wheeler spirals have been deposited on the very thin dielectric layers which are laminated into a single structure. In FIG. 80, one can see the contact pads 300 at 300' and that the Wheeler spiral circuit trace structures are actually an overlay of circuit traces 312 and 312'. In a preferred embodiment, the circuit traces 312 and the contact pads 302 and the electrical interconnections would all be of suitable biocompatible materials. In addition, the insulative or dielectric layer 308' separating them would also be of suitable biocompatible materials. This would allow one to construct bandstop filters for use in the electrodes of various types of active implantable medical devices, such as neurostimulator arrays and the like. Examples of biocompatible circuit traces 312 would include biocompatible metals, such as MP35N, gold, platinum and the like.

Figure 81:
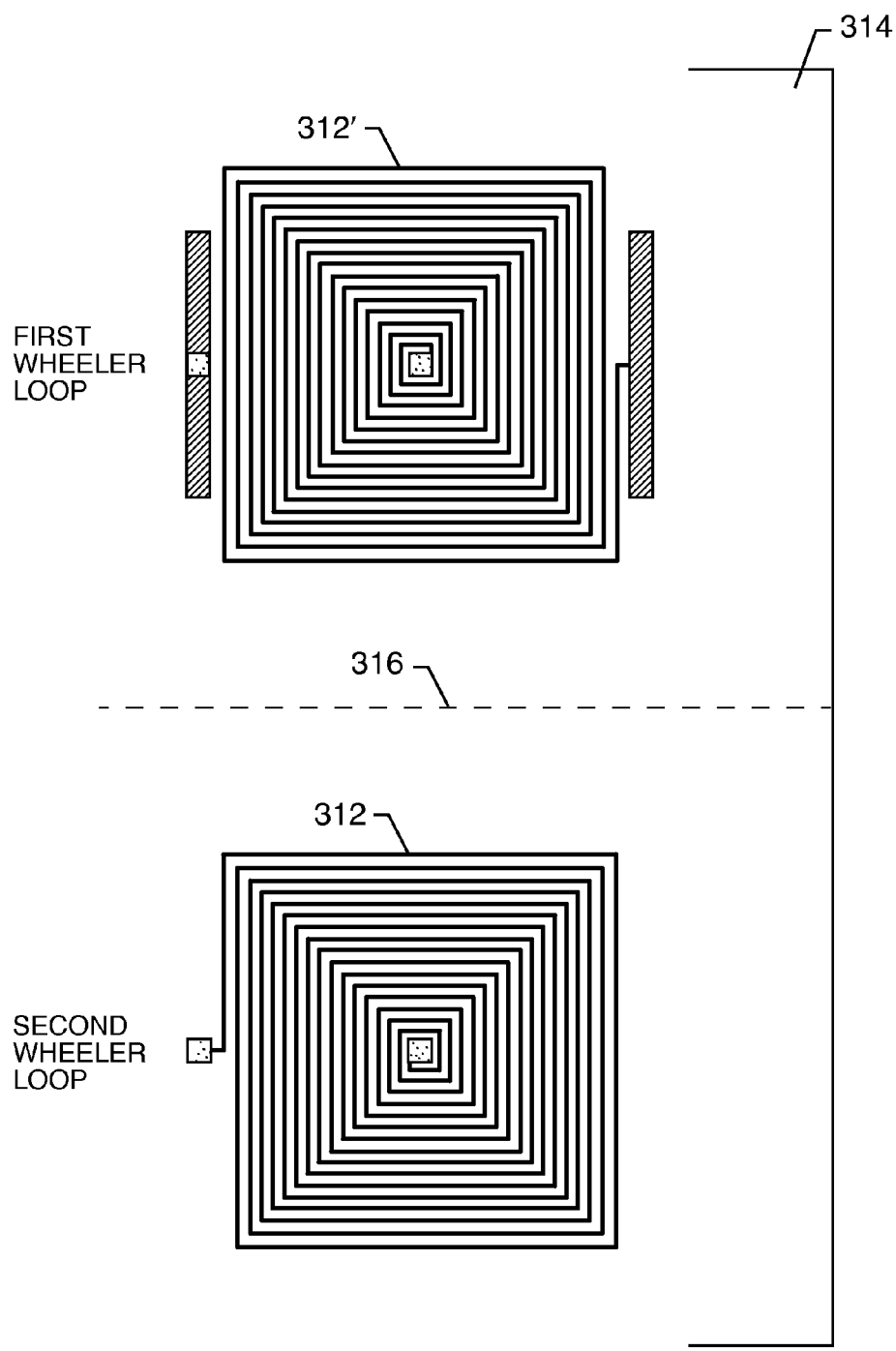
FIG. 81 is a manufacturing embodiment of the structures of FIGS. 77 and 78.
Figure 82:
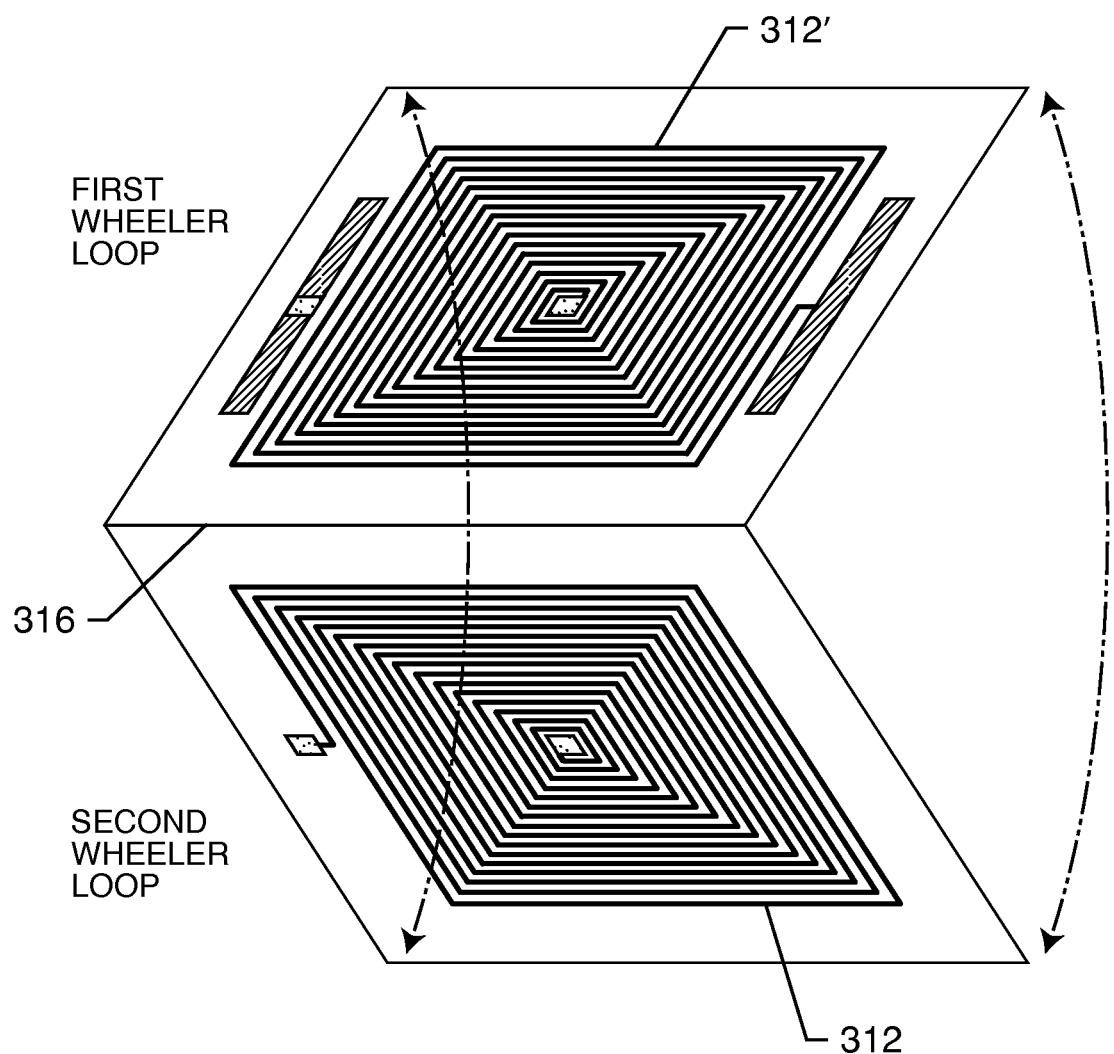
FIG. 82 is the next step of the manufacturing embodiment of FIG. 81.

FIG. 81 illustrates a method of manufacturing where the upper and lower layers of the Wheeler spiral multihelical wave filter 301 of FIG. 79. In this case, the upper and lower layers, including circuit traces 312' and 312 are all screened on a single dielectric or polymer carrier or film 314. Typically, this would be a thin sheet of a biocompatible polymer. There is also a fold line 316. By folding this thin dielectric thin-film or dielectric material, one can then align the upper and lower layers of the multihelical Wheeler spiral wave filter 301 along the fold line 316, as illustrated in FIG. 82. Once the fold is completed, the upper circuit trace 312' is pressed flat down against the lower circuit trace 312 such that the circuit trace is carefully overlayed with each other to form maximum parasitic and mutual capacitance between the upper and lower layer. After folding, laminating and filling the via holes 310 and 310', FIG. 82 becomes the multihelical Wheeler spiral structure 301 previously described in FIG. 80.

Figure 83:
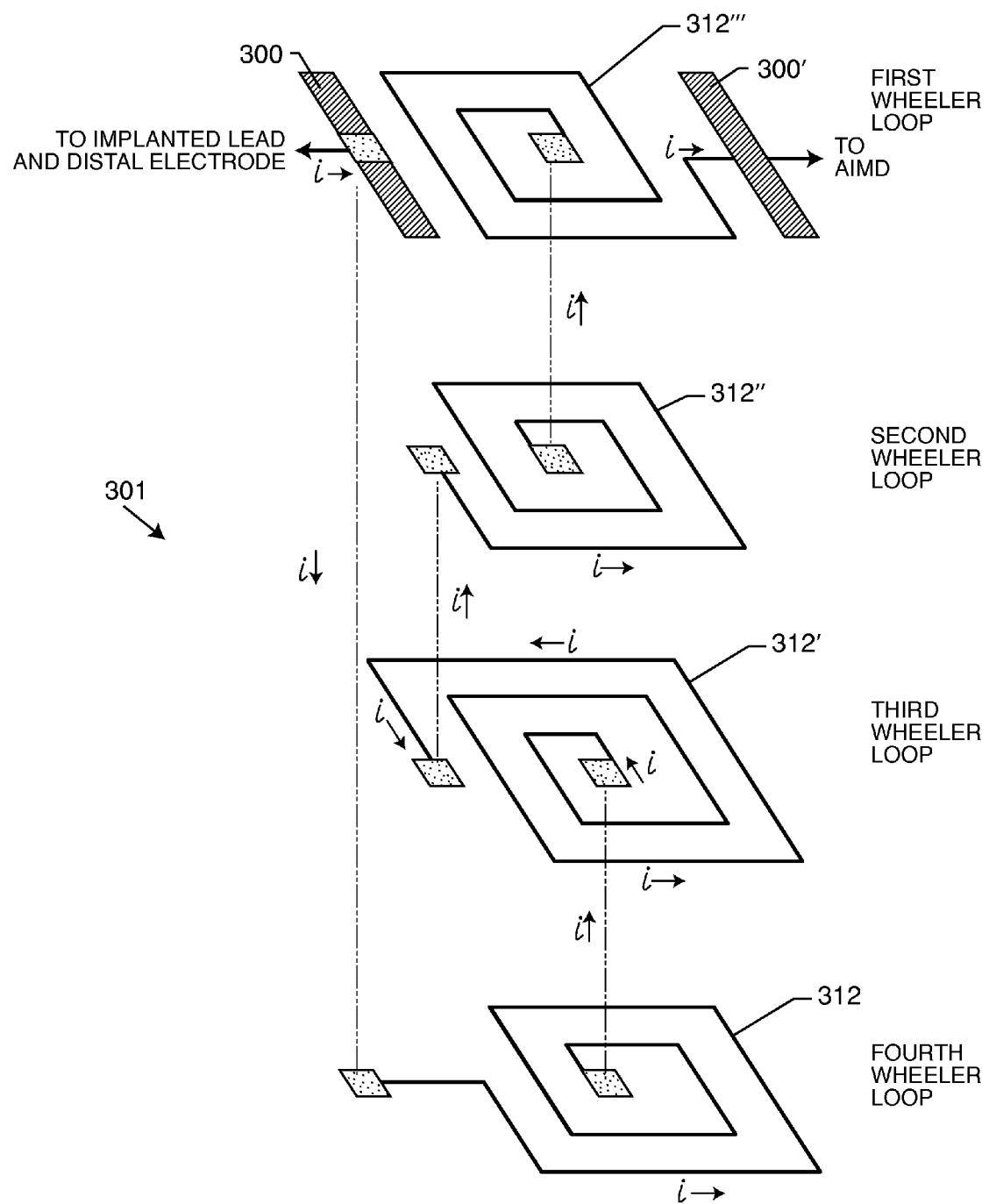
FIG. 83 is a simplified four layer Wheeler spiral with similar flowing induced RF currents between layers.
Figure 83A:
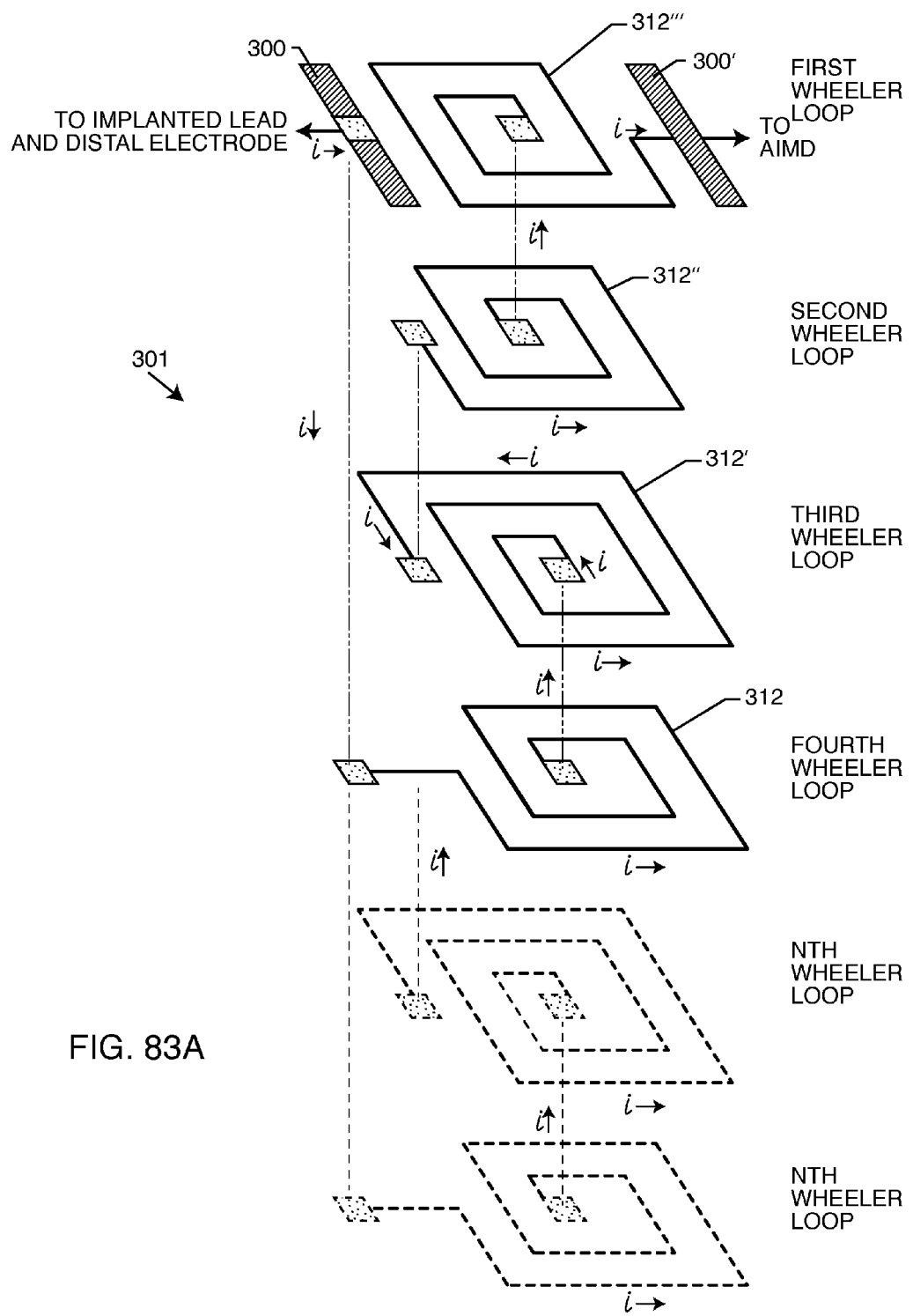
FIG. 83A is similar to FIG. 83 now showing "n" number of layers.

FIG. 83 is very similar to FIG. 75 except in this case, there are four layers (312, 312', 312'', 312''') of novel Wheeler spirals that have been constructed such that the RF-induced currents are always in the same direction in each layer. As previously described, this leads for optimal magnetic coupling and optimal parasitic capacitance such to maximize the impedance of the bandstop filter at resonance. It will be obvious to those skilled in the art that any number of layers, including "n" number of layers, could be used for the novel Wheeler spiral bandstop filters 301 of the present invention as shown in FIG. 83A.

Figure 84A:
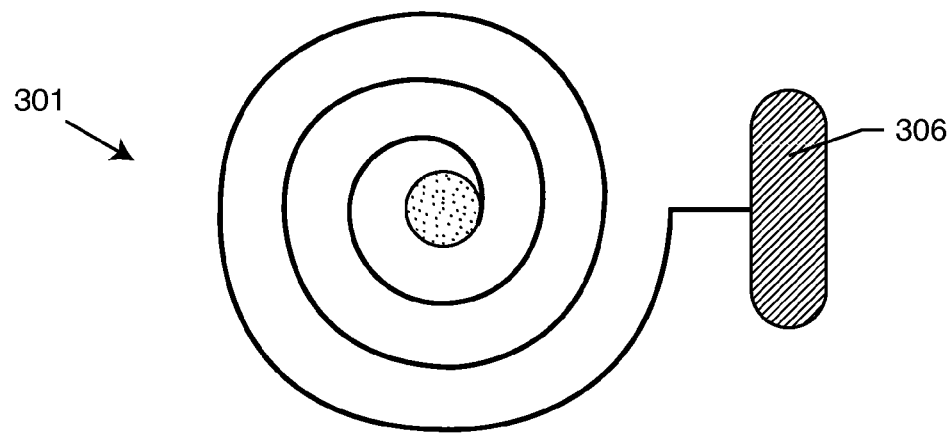
FIG. 84A is an embodiment of a circuit trace for a Wheeler spiral.
Figure 84B:
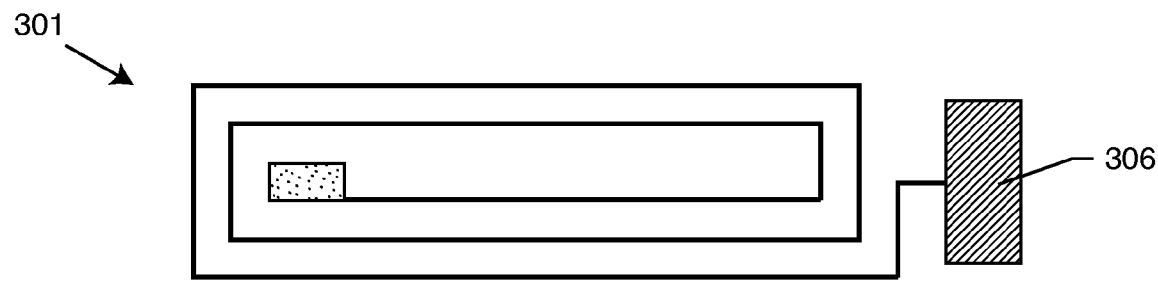
FIG. 84B is another embodiment of a circuit trace for a Wheeler spiral.
Figure 84C:
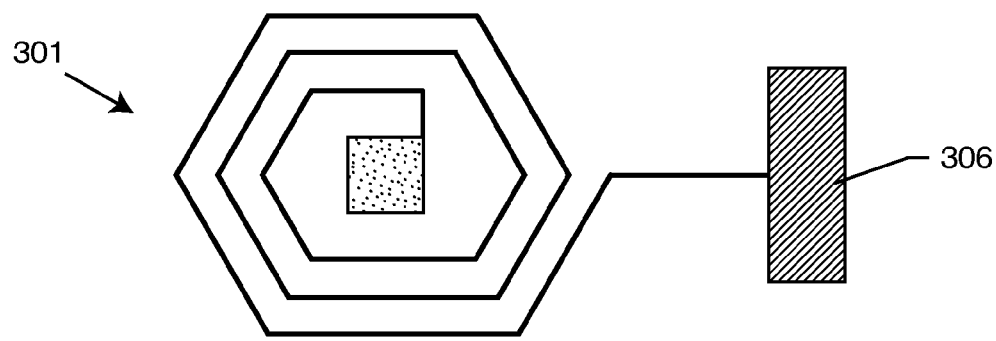
FIG. 84C is another embodiment of a circuit trace for a Wheeler spiral.

FIGS. 84A through 84C represent alternate versions of the top layer of the Wheeler spiral bandstop filters 301 of the present invention illustrating a circular shape as shown in FIG. 84A, a rectangular shape as shown in FIG. 84B, or even a hexagon as shown in FIG. 84C. Again, just the upper layer of what would be a multilayer Wheeler spiral bandstop filter is illustrated in FIGS. 84A through 84C. It would be obvious to those skilled in the art that any number of layers of the same shapes could be laid up as previously described in FIG. 75 or in FIG. 83.

Figure 85:
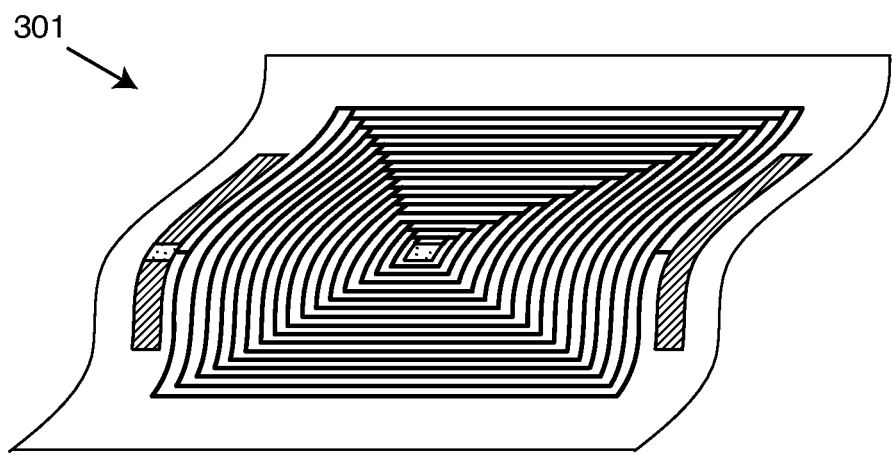
FIG. 85 is a view similar to the structure of FIG. 80, now showing a flexible substrate.
Figure 86:
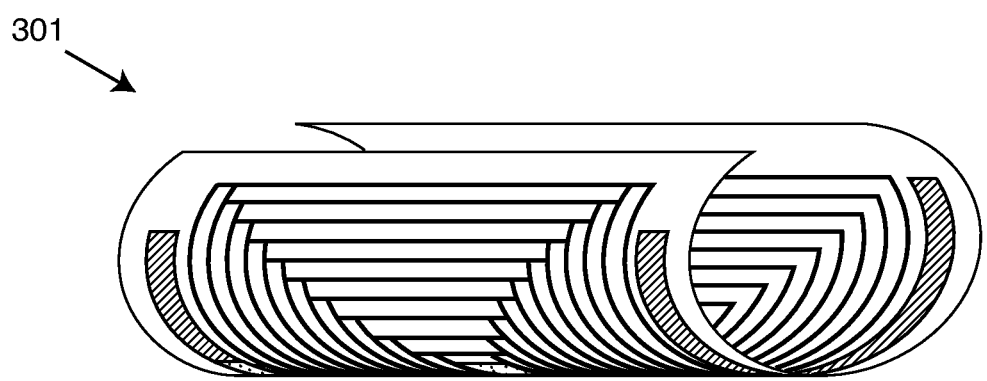
FIG. 86 is a view similar to the structure of FIG. 80, now showing the flexible substrate formed into a roll.

When deposited on film, FIG. 85 illustrates the extreme flexibility of the multilayer Wheeler spiral bandstop filter 301 of the present invention. These thin films are highly flexible and can even be rolled into a cylindrical shape as shown in FIG. 86. For insertion into a transvenous lead, a cylindrical shape is a much better form factor for venous insertion, or even tunneling, as opposed to a flat square or rectangular shape. Also, the Wheeler spiral bandstop filter could be rolled around a mandrel or core of the lead such to facilitate the passage of the guide wire to facilitate transvenous insertion and steering. The Wheeler spiral bandstop filter may be constructed from a tape-based flexible base as the tape can have its own attachment or other material material suitable for forming these structures. Another manufacturing option would be to create the Wheeler spiral bandstop filter by spin coating onto a flexible substrate. Wheeler spiral bandstop filter patterns may also be created using conventional sputter or evaporation techniques, and from patterning such as using photoresist, etching and then photoresist removal processes. Examples of biocompatible dielectric materials or thin films include nonconductive polyimide, silicone and the like.

The examples of the dielectric substrate having bioinert/biocompatible polymers include polydimethylsoloxanes (PDMS), polyethyleneterephthalate (PET), teflons, teflons doped with dielectrics or other, polytetrafluoroethylene (PTFE), ethylenetetrafluoroethylene (ETFE), parylenes, polyether block amide (PEBAX), polyetheretherketone (PEEK), polystyrenes, polysulfones, polypropylenes, polycarbonates, polyvinyl chloride (PVC), polyxylylene polymers, polyamides, polyimides, nylon, epoxies, and other such suitable polymers, elastomers and gels, including combinations thereof.

The examples of the dielectric substrate having configurable materials include photosensitive polymers and copolymers, elastomers and gels, such as but not limited to photosensitive or photopatternable polymers, microstructured dielectric rubbers, biocompatible dielectric particles (micron, submicron, nano and ultranano) embedded in flexible, stretchable, conformal biocompatible substrates such as but not limited to silicones, urethanes, PDMS, PET, and composites of combinations thereof either as a unique, single material structure or configurable into layered structures wherein the layers may be made with and without filler materials, all of the above including combinations thereof.

The examples of the dielectric substrate having carbon materials include pyrolitic and vitreous carbons, composites using nano and ultranano carbons, fiber, chopped fiber, ground chopped fiber, submicron fibers, whiskers and the like, nanocrystalline (NCD) and ultrananocrystalline diamond (UNCD), intrinsic diamond, doped diamond, hybrid biocompatible oxide/NCD layered combinations, hybrid biocompatible oxide/UNCD layered combinations, including combinations thereof.

The examples of the dielectric substrate having other materials include talcs, minerals (such as calcium carbonate, titanium dioxide, aluminum dioxide, sapphire, mica, silica), vapor deposited, e-beam deposited oxide, and atomic layer deposited films such as tantalum oxide ($Ta_2O_5$), anodized tantalum, aluminum oxide ($Al_2O_3$), titanium oxide ($TiO_2$), anodized titanium, tantalum nitride (TaN), titanium nitride (TiN), silicon nitride (SiN), barium titanate ($BaTiO_3$), silicon oxide ($SiO_2$), hafnium oxide ($HfO_2$) and the like, including combinations thereof.

Figure 87:
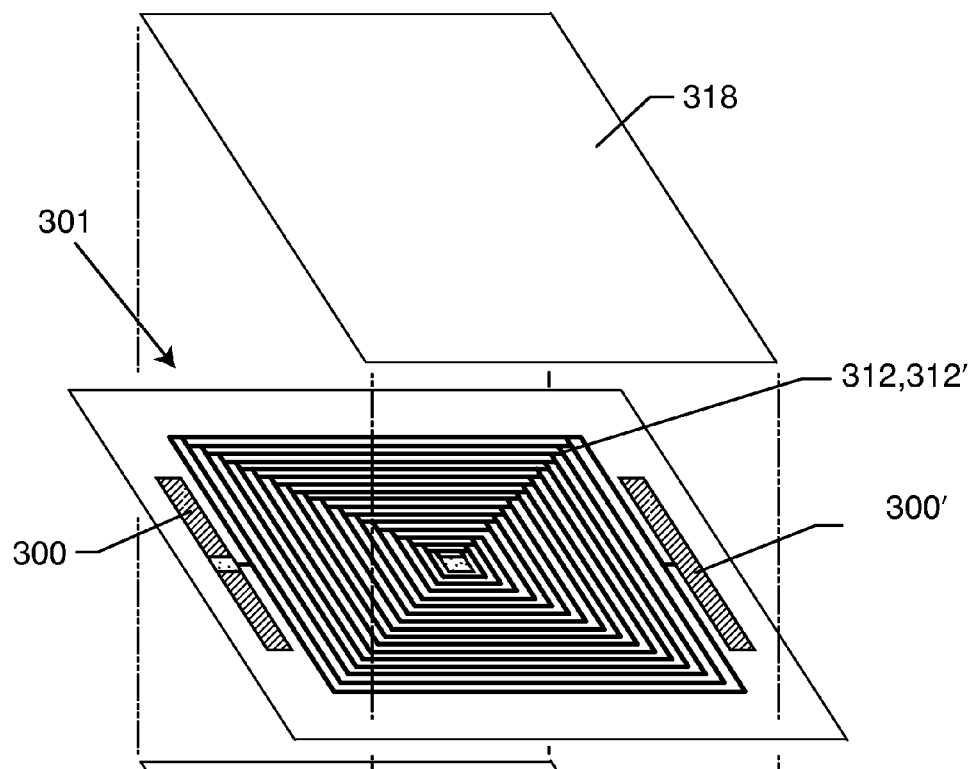
FIG. 87 is a view similar to the structure of FIG. 80, now showing a protective or insulative covering.

FIG. 87 represents the Wheeler spiral wave filter 301 from FIG. 80 wherein, an upper insulating sheet 318 and a lower insulating sheet 318' have been placed over the top and bottom. This is desirable in that it provides electrical insulation and mechanical protection to the circuit trace layers 312 and 312'. The contact pads 300 and 300' are exposed to facilitate suitable electrical connection. Alternatively, even after electrical connections have been made to the contact pads 300, the insulation material 318, 318' could be added and then could at that time, after the electrical connections are formed be also overlaid over the contact pads 300 and 300' (not shown).

Figure 88:
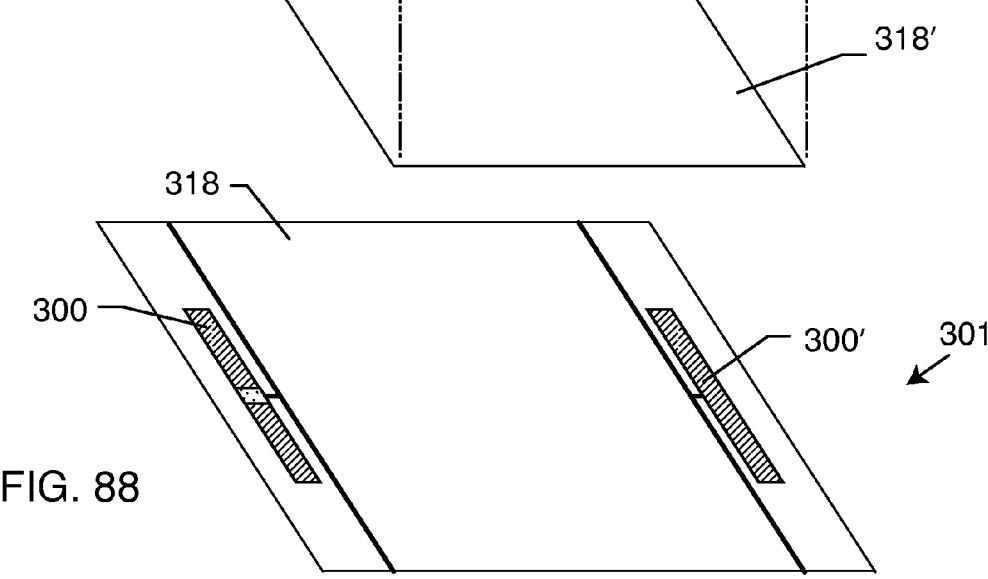
FIG. 88 is an assembled view of the structure of FIG. 87.
Figure 89:
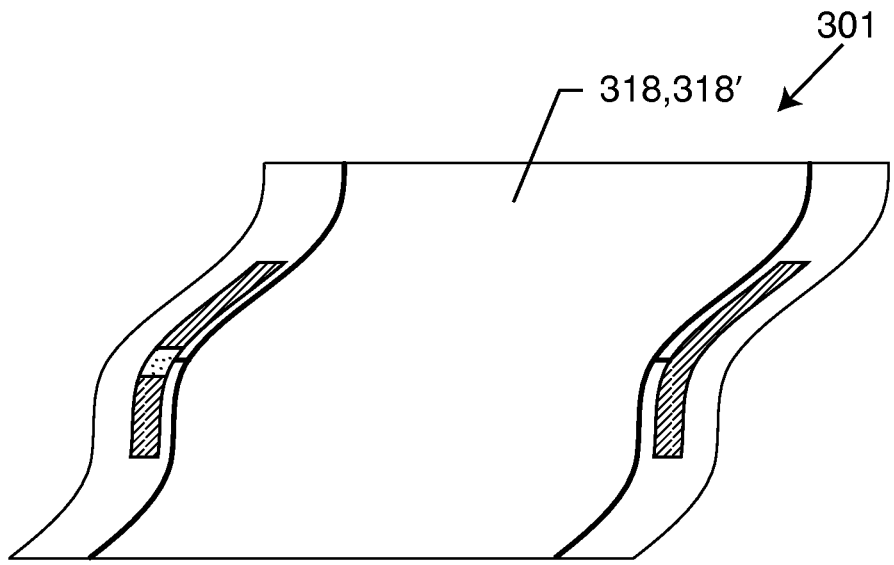
FIG. 89 is a view similar to the structure of FIG. 88, now showing a flexible substrate.
Figure 90:
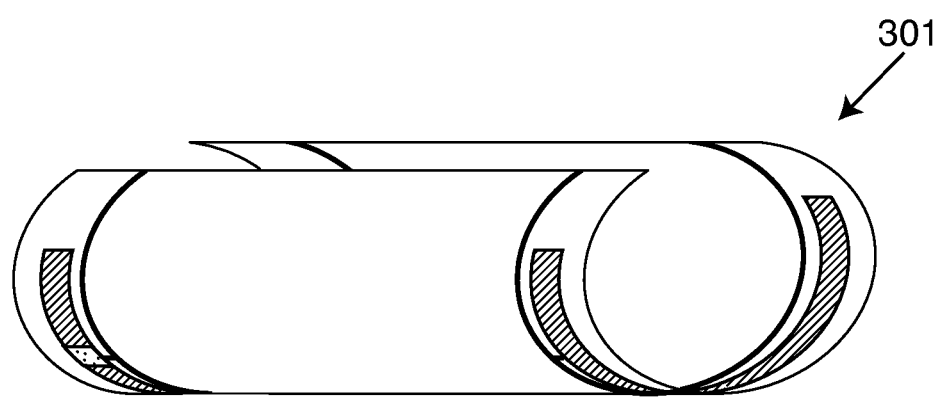
FIG. 90 is a view similar to the structure of FIG. 88, now showing the flexible substrate formed into a roll.

FIG. 89 and FIG. 90 illustrate that the insulative structure of FIG. 88 with insulation layers 318, 318' can still all be formed of flexible materials such that they can be bent or rolled up as shown in FIG. 90.

Figure 91:
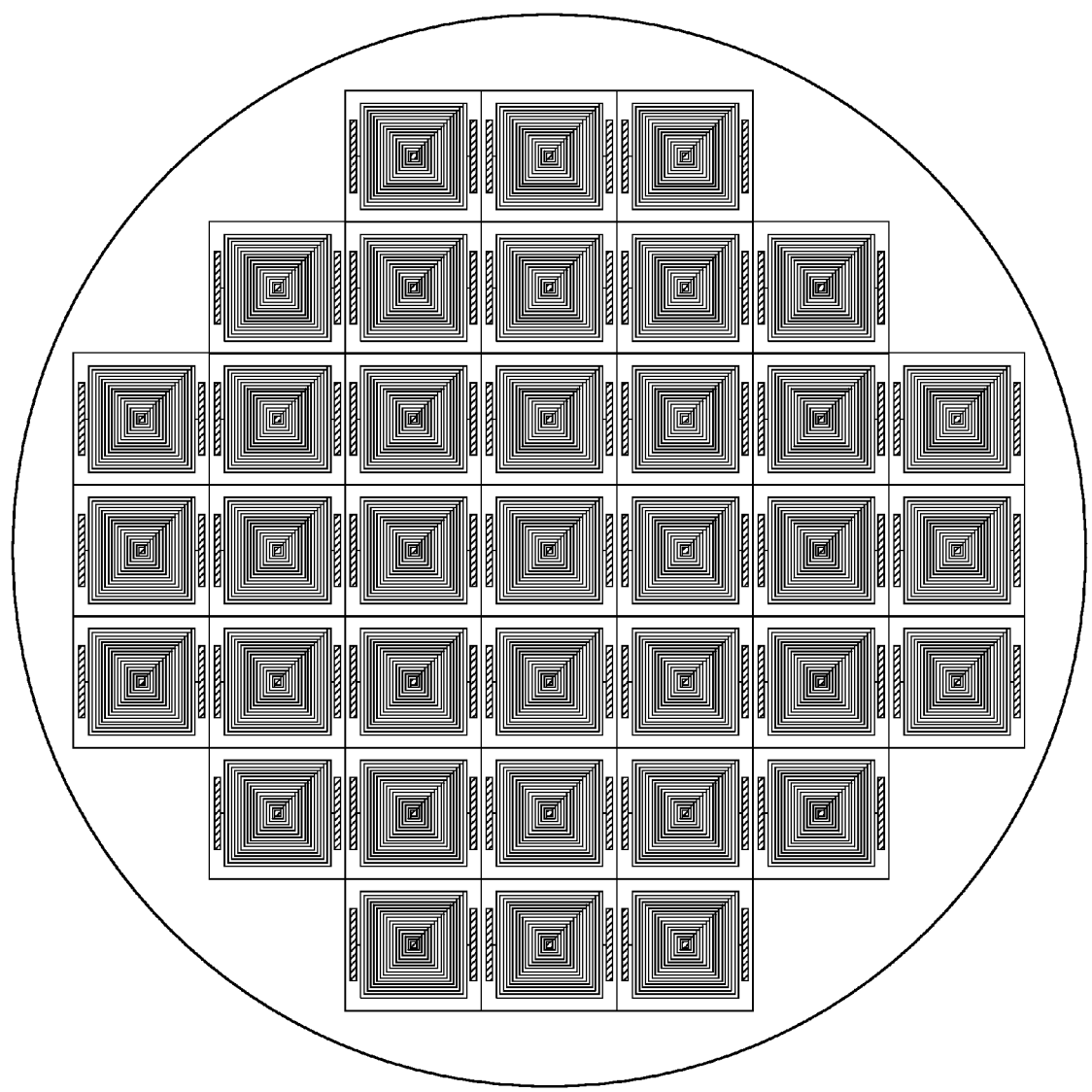
FIG. 91 top view of a high volume manufacturing wafer with multiple bandstop filters of the structure of FIG. 80.

FIG. 91 is a top view of a high volume manufacturing wafer indicating that many bandstop filter layers can be silk-screened, sputtered or electrically deposited as a thin-film at one time. After construction, they can be diced out of the carrier or the bar in a high volume, highly efficient operation.

Although several embodiments of the invention have been described in detail for purposes of illustration, various modifications of each may be made without departing from the spirit and scope of the invention. Accordingly, the invention is not to be limited, except as by the appended claims.

What is claimed is:

1. An implantable lead, comprising:
   a) at least one implantable lead conductor extending from a proximal conductor end to a distal conductor portion having a distal conductor end, wherein the proximal conductor end is configured to be electrically connectable to electronic circuits of an implantable medical device;
   b) at least one electrode electrically connected to the distal conductor portion or the distal conductor end, wherein the electrode is configured to be placed in contact with biological cells inside a body;
   c) a dielectric substrate;
   d) at least a first spiral inductor spaced from a second spiral inductor and supported on the dielectric substrate, wherein the first spiral inductor spirals in either a clockwise or counter-clockwise direction from a first electrical point to a first contact pad and wherein the second spiral inductor spirals from a second contact pad to a second electrical point and in a counter-clockwise or clockwise direction that is opposite to that of the first spiral inductor,
   e) wherein the dielectric substrate is characterized as having been folded along an intermediate fold line located between and spaced from both of the first and second spiral inductors so that the first and second spiral inductors are in a capacitive relationship residing one above the other with the dielectric substrate disposed therebetween;
   f) a conductive material extending through the dielectric substrate to electrically connect the first and second contact pads so that the first and second spiral inductors are only electrically connected to each other at the respective first and second contact pads,
   g) wherein the first and second electrical points of the respective first and second spiral inductors are electrically connected to the lead conductor intermediate the proximal conductor end and the electrode, and
   h) wherein a first multi-turn loop current of the first spiral inductor is in the same direction as a second multi-turn loop current of the second spiral inductor.

2. The implantable lead of claim 1, wherein a bandstop filter inductance is formed by the first and second spiral inductors and wherein a bandstop filter capacitance comprising parasitic capacitance is formed between adjacent turns of the respective first and second spiral inductors and between the first and second spiral inductors.

3. The implantable lead of claim 2, wherein the bandstop filter inductance and bandstop filter capacitance comprise an equivalent circuit bandstop filter.

4. The implantable lead of claim 3, wherein the equivalent circuit bandstop filter is configured to attenuate an MRI RF pulsed frequency at or near an RF resonant center frequency.

5. The implantable lead of claim 4, wherein the RF resonant center frequency is at or near 64 MHz or 128 MHz.

6. The implantable lead of claim 1, wherein the first and second spiral inductors comprise conductive circuit traces comprising the lead conductor, the conductive circuit traces having a cross-section perpendicular to their length that is selected from the group consisting of circular, rectangular, square, oval, pentagon, hexagon or irregular shaped.

7. The implantable lead of claim 1, wherein the dielectric substrate and the first and second spiral inductors are flexible.

8. The implantable lead of claim 7, wherein the dielectric substrate is formable into a roll.

9. The implantable lead of claim 1, including an insulative covering over the first and second spiral inductors.

10. The implantable lead of claim 1, further comprising a third spiral inductor spiraling from a third inner connection point inside the spiral to a third outer connection point, wherein the second and third spiral inductors are in a stacked relationship with a second dielectric there between, and wherein one of the third inner and outer connection points of the third spiral inductor is electrically connected to the second connection point of the second spiral inductor with the other of the third inner and the outer connection points not connected to the second spiral inductor being electrically connected to the lead conductor between the proximal conductor end and the electrode, wherein respective multi-turn loop currents of the first, second and third spiral inductors are in the same direction.

11. The implantable lead of claim 10, further comprising a fourth spiral inductor spiraling from a fourth inner connection point to a fourth outer connection point, wherein the third and fourth spiral inductors are in a stacked relationship with a third dielectric there between, and wherein the other of the third inner and outer connection points not connected to the second spiral inductor is electrically connected to one of the fourth inner and outer connection points of the fourth spiral inductor with the other of the fourth inner and outer connection points not connected to the third spiral inductor being electrically connected to the lead conductor between the proximal conductor end and the electrode, and wherein respective multi-turn loop currents of the first, second, third and fourth spiral inductors are in the same direction.

12. The implantable lead of claim 1, wherein an n number of spiral inductors that are substantially similar in pattern to the first and second spiral inductors are electrically connected one to the next with the first and $n^{th}$ spiral inductors being electrically connected to the lead conductor between the proximal conductor end and the electrode.

13. The implantable lead of claim 1, wherein the first spiral inductor attenuates a first MRI RF pulsed frequency at or near a first RF resonant center frequency or range of frequencies.

14. The implantable lead of claim 13, wherein the second spiral inductor attenuates a second MRI RF pulsed frequency at or near a second RF resonant center frequency or range of frequencies.

15. The implantable lead of claim 14, wherein the first and second RF resonant center frequencies are substantially different frequencies.

16. The implantable lead of claim 15, wherein the first RF resonant frequency comprises 64 MHz and the second RF resonant center frequency comprises 128 MHz.

17. The implantable lead of claim 1, wherein the dielectric substrate comprises a tape-based flexible substrate.

18. The implantable lead of claim 1, wherein the first and second spiral inductors are characterized as having been deposited on the dielectric substrate by at least one of the group consisting of a spin coating, a conventional sputter process, an evaporation technique, a photoresist process, an etching process, a photoresist removal process, a silk-screening process, and an electrically deposited process.

19. The implantable lead of claim 1, wherein the dielectric substrate is of a biocompatible material selected from the group consisting of bioinert or biocompatible polymers including polydimethylsoloxanes (PDMS), polyethyleneterephthalate (PET), teflons, teflons doped with dielectrics, polytetrafluoroethylene (PTFE), ethylenetetrafluoroethylene (ETFE), parylenes, polyether block amide (PEBAX), polyetheretherketone (PEEK), polystyrenes, polysulfones, polypropylenes, polycarbonates, polyvinyl chloride (PVC), polyxylylene polymers, polyamides, polyimides, nylon, epoxies, elastomers, and gels.

20. The implantable lead of claim 1, wherein the dielectric substrate is of a photosensitive material selected from the group consisting of photosensitive polymers and co-polymers, photosensitive or photopatternable polymers, microstructured dielectric rubbers or biocompatible dielectric particles embedded in flexible, stretchable, conformal biocompatible substrates including silicones, urethanes, PDMS or PET, where the biocompatible dielectric particles comprise micron, submicron, nano, and ultranano biocompatible dielectric particles.

21. The implantable lead of claim 1, wherein the dielectric substrate is of a carbonaceous material selected from the group consisting of pyrolitic and vitreous carbons, composites using nano and ultranano carbons, fibers, chopped fibers, ground chopped fibers, submicron fibers, whiskers, nanocrystalline (NCD) and ultrananocrystalline diamond (UNCD), intrinsic diamond, doped diamond, hybrid biocompatible oxide/NCD layered combinations, and hybrid biocompatible oxide/UNCD layered combinations.

22. The implantable lead of claim 1, wherein the dielectric substrate is of a material selected from the group consisting of talcs, calcium carbonate, titanium dioxide, aluminum dioxide, sapphire, mica, silica, vapor deposited, e-beam deposited oxide, atomic layer deposited films including tantalum oxide ($Ta_2O_5$), anodized tantalum, aluminum oxide ($Al_2O_3$), titanium oxide ($TiO_2$), anodized titanium, tantalum nitride (TaN), titanium nitride (TiN), silicon nitride (SiN), barium titanate ($BaTiO_3$), silicon oxide ($SiO_2$), and hafnium oxide ($HfO_2$).

23. The implantable lead of claim 1 wherein the first and second spiral inductors reside on the same side of the dielectric substrate prior to the substrate characterized as having been folded.

24. The implantable lead of claim 1 wherein the first and second spiral inductors supported on the folded dielectric substrate are provided in a cylindrical shape.

25. The implantable lead of claim 1 wherein the first and second spiral inductors are substantially similar in pattern.

26. The implantable lead of claim 1 wherein, along with a capacitive series resistance ($R_C$) and an inductor series resistance ($R_L$), the first and second spiral inductors have sufficient parasitic capacitance between their adjacent respective spiral turns and between each other so that at low frequencies of about 10 Hz to about 1 kHz an inductive reactance and the inductor series resistance ($R_L$) permit passage of biological signals from the electrode to the proximal conductor end while a capacitive reactance and the capacitive series resistance ($R_C$) substantially act as an open circuit to the same biological signals that the inductive reactance and the inductor series resistance ($R_L$) permit to pass, and
wherein the capacitive series resistance ($R_C$) and the inductor series resistance ($R_L$) provide a filter Q having a 3-dB bandwidth that is at least 100 kHz.

27. The implantable lead of claim 1 wherein at least one of the first and second spiral inductors is planar.

28. An implantable lead, comprising:
a) at least one implantable lead conductor extending from a proximal conductor end to a distal conductor portion having a distal conductor end, wherein the proximal conductor end is configured to be electrically connectable to electronic circuits of an implantable medical device;
b) at least one electrode electrically connected to the distal conductor portion or the distal conductor end, wherein the electrode is configured to be placed in contact with biological cells inside a body;
c) a dielectric substrate;
d) at least a first spiral inductor spaced from a second spiral inductor and supported on the dielectric substrate, wherein the first spiral inductor spirals in either a clockwise or counter-clockwise direction from a first electrical point to a first contact pad and wherein the second spiral inductor spirals from a second contact pad to a second electrical point and in a counter-clockwise or clockwise direction that is opposite to that of the first spiral inductor,
e) wherein the dielectric substrate is characterized as having been folded along an intermediate fold line located between and spaced from both of the first and second spiral inductors so that the first and second spiral inductors are in a capacitive relationship residing one above the other with the dielectric substrate disposed therebetween;
f) a conductive material extending through the dielectric substrate to electrically connect the first and second contact pads so that the first and second spiral inductors are only electrically connected to each other at the respective first and second contact pads, and
g) a mandrel comprising an intermediate mandrel body extending from a proximal mandrel end to a distal mandrel end, wherein the proximal and distal mandrel ends are electrically conductive, and wherein the dielectric substrate is supported on the mandrel with the first and second electrical points being electrically connected to respective one of the proximal and distal electrically conductive mandrel ends,
h) wherein the first and second electrically conductive mandrel ends are electrically connected to the lead conductor intermediate the proximal conductor end and the electrode, and
i) wherein a first multi-turn loop current of the first spiral inductor is in the same direction as a second multi-turn loop current of the second spiral inductor.

29. The implantable lead of claim 28 wherein the mandrel has a central lumen extending from the proximal mandrel end to the distal mandrel end.

30. An implantable lead, comprising:
a) at least one implantable lead conductor extending from a proximal conductor end to a distal conductor portion having a distal conductor end, wherein the proximal conductor end is configured to be electrically connectable to electronic circuits of an implantable medical device;
b) at least one electrode electrically connected to the distal conductor portion or the distal conductor end, wherein the electrode is configured to be placed in contact with biological cells inside a body;
c) a dielectric substrate;
d) at least a first spiral inductor spaced from a second spiral inductor and supported on the dielectric substrate, wherein the first spiral inductor spirals in either a clockwise or counter-clockwise direction from a first electrical point to a first contact pad and wherein the second spiral inductor spirals from a second contact pad to a second electrical point and in a counter-clockwise or clockwise direction that is opposite to that of the first spiral inductor, e) wherein the dielectric substrate is characterized as having been folded along an intermediate fold line located between and spaced from both of the first and second spiral inductors so that the first and second spiral inductors are adjacent to each other with the dielectric substrate disposed therebetween; and f) a second dielectric substrate located between the first and second spiral inductors so that the first and second spiral inductors are in a capacitive relationship residing one above the other;

g) a conductive material extending through the second dielectric substrate to electrically connect the first and second contact pads so that the first and second spiral inductors are only electrically connected to each other at the respective first and second contact pads, h) wherein the first and second electrical points of the respective first and second spiral inductors are electrically connected to the lead conductor intermediate the proximal conductor end and the electrode, and i) wherein a first multi-turn loop current of the first spiral inductor is in the same direction as a second multi-turn loop current of the second spiral inductor.

31. An implantable lead, comprising:

a) at least one implantable lead conductor extending from a proximal conductor end to a distal conductor portion having a distal conductor end, wherein the proximal conductor end is configured to be electrically connectable to electronic circuits of an implantable medical device;

b) at least one electrode electrically connected to the distal conductor portion or the distal conductor end, wherein the electrode is configured to be placed in contact with biological cells inside a body;

c) a dielectric substrate;

d) at least a first spiral inductor spaced from a second spiral inductor and supported on the dielectric substrate, wherein the first spiral inductor spirals inwardly in either a clockwise or counter-clockwise direction from a first electrical point adjacent to an edge of the dielectric substrate to a first contact pad centrally located inside the first spiral inductor and wherein the second spiral inductor spirals outwardly in a counter-clockwise or clockwise direction that is opposite to that of the first spiral inductor from a second centrally located contact pad to a second electrical point adjacent to an edge of the dielectric substrate, e) wherein the dielectric substrate is characterized as having been folded along an intermediate fold line located between and spaced from both of the first and second spiral inductors so that the first and second spiral inductors are in a capacitive relationship residing one above the other with the dielectric substrate disposed therebetween, f) a conductive material extending through the dielectric substrate to electrically connect the first and second contact pads so that the first and second spiral inductors are only electrically connected to each other at the respective first and second contact pads, g) wherein the first and second electrical points of the respective first and second spiral inductors are electrically connected to the lead conductor intermediate the proximal conductor end and the electrode, and h) wherein a first multi-turn loop current of the first spiral inductor is in the same direction as a second multi-turn loop current of the second spiral inductor.

* * * * *